United States Patent
Bilic et al.

(10) Patent No.: US 10,561,653 B2
(45) Date of Patent: Feb. 18, 2020

(54) 5-BROMO-2,6-DI-(1H-PYRAZOL-1-YL)PYRIMIDIN-4-AMINE FOR USE IN THE TREATMENT OF CANCER

(71) Applicants: NOVARTIS AG, Basel (CH); PALOBIOFARMA, S.L., Mataro Barcelona (ES)

(72) Inventors: Sanela Bilic, Urbandale, IA (US); Juan Alberto Camacho Gomez, Barcelona (ES); John Scott Cameron, Belmont, MA (US); Julio Cesar Castro-Palomino Laria, Barcelona (ES); Danny Roland Howard, Jr., Washington, NJ (US)

(73) Assignees: Novartis AG, Basel (CH); Palobiofarma, S.L., Mataro Barcelona (ES)

( * ) Notice: Subject to any disclaimer, the term of this patent is extended or adjusted under 35 U.S.C. 154(b) by 59 days.

(21) Appl. No.: 15/751,140

(22) PCT Filed: Aug. 10, 2016

(86) PCT No.: PCT/IB2016/054834
§ 371 (c)(1),
(2) Date: Feb. 7, 2018

(87) PCT Pub. No.: WO2017/025918
PCT Pub. Date: Feb. 16, 2017

(65) Prior Publication Data
US 2018/0228802 A1    Aug. 16, 2018

Related U.S. Application Data

(60) Provisional application No. 62/335,984, filed on May 13, 2016.

(30) Foreign Application Priority Data

Aug. 11, 2015   (EP) ..................................... 15382425

(51) Int. Cl.
A61K 39/395 (2006.01)
A61K 31/506 (2006.01)
A61P 35/00 (2006.01)
A61K 39/00 (2006.01)

(52) U.S. Cl.
CPC ........ A61K 31/506 (2013.01); A61K 39/3955 (2013.01); A61P 35/00 (2018.01); *A61K 2039/545* (2013.01); *A61K 2300/00* (2013.01)

(58) Field of Classification Search
CPC .................................................. A61K 31/506
See application file for complete search history.

(56) References Cited

U.S. PATENT DOCUMENTS

| 8,552,154 B2* | 10/2013 | Freeman ............ C07K 16/2818 530/387.1 |
| 8,709,416 B2 | 4/2014 | Langermann et al. |
| 8,784,815 B2* | 7/2014 | Korman ............ A01K 67/0275 424/144.1 |
| 8,796,284 B2* | 8/2014 | Camacho Gomez ........................ C07D 403/04 514/256 |
| 2015/0210769 A1 | 7/2015 | Freeman et al. |

FOREIGN PATENT DOCUMENTS

| EP | 257850 A2 | 3/1988 |
| WO | WO2003050241 A2 | 6/2003 |
| WO | WO 2005/058883 A1 | 6/2005 |
| WO | WO2006110884 A2 | 10/2006 |
| WO | WO 2008/116185 A1 | 9/2008 |
| WO | 2008/147482 A2 | 12/2008 |
| WO | WO2009/033161 A1 | 3/2009 |
| WO | 2011/121418 A1 | 10/2011 |
| WO | WO2015/070060 A1 | 5/2015 |
| WO | WO2015/112900 A1 | 7/2015 |

OTHER PUBLICATIONS

Akio Ohta et al: "A2A adenosine receptor protects tumors from antitumor T cells", Proceedings of the National Academy of Sciences, National Academy of Sciences, US, vol. 103, No. 35, Aug. 29, 2006, pp. 13132-13137.
Mediavilla-Varela et al., "Antagonism of adenosine A2A receptor expressed by lung adenocarcinoma tumor cells and cancer associated fibroblasts inhibits their growth", Cancer Biology & Therapy, 14:9, pp. 860-868, Sep. 2013.
Beavis et al., "Blockade of A2A receptors potently suppresses the metastasis of CD73+ tumors", PNAS, vol. 110, No. 36, Sep. 3, 2013.
Mittal et al., "Antimetastatic Effects of Blocking PD-1 and the Adenosine A2A Receptor", Cancer Res; 74(14); pp. 3652-3658, Jul. 14, 2015.
Press Release Lungevity 2014 Therapeutics Award: https://lungevity.org/research-we-fund/research-funded-to-date/research-database/antagonism-of-adenosine-a2a-receptor-to, 2014.
Antonia et al., "Immuno-oncology Combinations: A Review of Clinical Experience and Future Prospects", Clin Cancer Res; 20(24); pp. 6258-6268, Dec. 15, 2014.
Beavis et al., "Adenosine Receptor 2A Blockade Increases the Efficacy of Anti-PD-1 through Enhanced Antitumor T-cell Responses", Cancer Immunology Research, 3(5), pp. 506-517, May 2015.
Leone et al., "A2aR antagonists: Next generation checkpoint blockade for cancer immunotherapy", computational and structural biotechnology journal, vol. 13, pp. 265-272 , 2015.

* cited by examiner

*Primary Examiner* — Sheela J. Huff
(74) *Attorney, Agent, or Firm* — Michelle Han

(57) ABSTRACT

The present invention relates to 5-bromo-2,6-di-(1H-pyrazol-1-yl)pyrimidin-4-amine, its pharmaceutically acceptable salts and co-crystals thereof and to pharmaceutical compositions comprising said compounds for use in the treatment of cancer.

17 Claims, 9 Drawing Sheets

Specification includes a Sequence Listing.

| Clone No. | Concentration µg/mL | Sequence | | | | | |
|---|---|---|---|---|---|---|---|
| | | HC | | | LC | | |
| | | FW1 | FW2 | FW3 | FW1 | FW2 | FW3 |
| | | 4 unique HC | | | 9 unique LC | | |
| 1 | 23.3 | a | a | a | b | a | c |
| 2 | 45.5 | a | a | a | e | a | b |
| 3 | 58.4 | a | b | b | e | a | b |
| 4 | 52.9 | a | b | b | b | b | d |
| 5 | 30 | a | a | a | b | b | d |
| 6 | 7.9 | a | a | a | c | a | a |
| 7 | 24.9 | a | a | a | b | b | a |
| 8 | 32.8 | a | b | b | a | a | a |
| 9 | 16.3 | a | a | a | a | a | a |
| 10 | 61.5 | a | b | b | b | a | a |
| 11 | 31.4 | a | a | a | b | a | a |
| 12 | 34.8 | a | a | a | e | c | a |
| 13 | 8.6 | a | a | a | d | b | a |
| 14 | 48.4 | b | b | b | b | a | a |
| 15 | 20.7 | b | b | b | a | a | a |
| 16 | 32.8 | a | c | b | a | a | a |

Figure 9

| Clone No. | Conc. μg/mL | Sequence | | | | | | Ranking | Competition Binding | | Ranking |
|---|---|---|---|---|---|---|---|---|---|---|---|
| | | HC | | | LC | | | FACS data | 1st exp. | 2nd exp.* | |
| | | FW1 | FW2 | FW3 | FW1 | FW2 | FW3 | | | | |
| Chimeric | 20.6 | 4 unique HC | | | 9 unique LC | | | | | | |
| 1 | 23.3 | a | a | a | b | a | c | 2 | 7 | 2 | A |
| 2 | 45.5 | a | a | a | e | a | b | 6 | 3 | 2 | D |
| 3 | 58.4 | a | b | b | e | a | b | 7 | 8 | 14 | E |
| 4 | 52.9 | a | b | b | b | b | d | 14 | 15 | 15 | B |
| 5 | 30 | a | a | a | b | b | d | 5 | 5 | | A |
| 6 | 7.9 | a | a | a | c | a | a | 1 | 7 | 3 | D |
| 7 | 24.9 | a | a | a | b | b | a | 4 | 7 | | D |
| 8 | 32.8 | a | b | b | a | a | a | 7 | 7 | 4 | C |
| 9 | 16.3 | a | a | a | a | a | a | 7 | 2 | 4 | B |
| 10 | 61.5 | a | b | b | b | a | a | 7 | 6 | | C |
| 11 | 31.4 | a | a | a | b | a | a | 6 | 4 | | B |
| 12 | 34.8 | a | a | a | e | c | a | 3 | 8 | 16 | D |
| 13 | 8.6 | a | a | a | d | b | a | 6 | 1 | 1 | D |
| 14 | 48.4 | b | b | b | b | a | a | 16 | 7 | 15 | C |
| 15 | 20.7 | b | b | b | a | a | a | 6 | 7 | 15 | C |
| 16 | 32.8 | a | c | b | a | a | a | 15 | 16 | 15 | C |

*empty boxes means worse than 4

Figure 10

SEQUENCE LISTING

```
<160> NUMBER OF SEQ ID NOS: 250

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Ile Tyr Pro Gly Thr Gly Gly Ser Asn Phe Asp Glu Lys Phe Lys
1               5                   10                  15

Asn

<210> SEQ ID NO 3
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 3

Trp Thr Thr Gly Thr Gly Ala Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Thr Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Gly Thr Gly Gly
1               5

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala
        115

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
caggtccagc tgcagcaacc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca catcctccac cacagcctac     240
atgcacctcg ccagcctgac atctgaggac tctgcggtct attactgtac aagatggact     300
actgggacgg gagcttattg gggccaaggg actctggtca ctgtctctgc a              351
```

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

```
Gln Val Gln Leu Gln Gln Ser Gly Ser Glu Leu Val Arg Pro Gly Ala
1               5                   10                  15
Ser Val Lys Leu Ser Cys Lys Ala Ser Gly Tyr Thr Phe Thr Thr Tyr
            20                  25                  30
Trp Met His Trp Val Arg Gln Arg Pro Gly Gln Gly Leu Glu Trp Ile
        35                  40                  45
Gly Asn Ile Tyr Pro Gly Thr Gly Gly Ser Asn Phe Asp Glu Lys Phe
    50                  55                  60
Lys Asn Arg Thr Ser Leu Thr Val Asp Thr Ser Ser Thr Thr Ala Tyr
65                  70                  75                  80
Met His Leu Ala Ser Leu Thr Ser Glu Asp Ser Ala Val Tyr Tyr Cys
                85                  90                  95
Thr Arg Trp Thr Thr Gly Thr Gly Ala Tyr Trp Gly Gln Gly Thr Leu
            100                 105                 110
Val Thr Val Ser Ala
        115
```

<210> SEQ ID NO 9
<211> LENGTH: 351
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9

```
caggtccagc tgcagcagtc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca catcctccac cacagcctac     240
atgcacctcg ccagcctgac atctgaggac tctgcggtct attactgtac aagatggact     300
actgggacgg gagcttattg gggccaaggg actctggtca ctgtctctgc a              351
```

<210> SEQ ID NO 10
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 10

Lys Ser Ser Gln Ser Leu Leu Asp Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Asp Tyr Ser Tyr Pro Cys Thr
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Ser Leu Leu Asp Ser Gly Asn Gln Lys Asn Phe
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ala Ser
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Tyr Ser Tyr Pro Cys
1               5

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gly Gly Thr Lys Leu Glu Ile
            100                 105                 110

Lys

<210> SEQ ID NO 17
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gacattgtga tgacccagtc tccatcctcc ctgactgtga cagcaggaga gaaggtcact     60
atgagctgca gtccagtca gagtctgtta gacagtggaa atcaaaagaa cttcttgacc    120
tggtaccagc agaaaccagg gcagcctcct aaactgttga tcttctgggc atccactagg    180
gaatctgggg tccctgatcg cttcacaggc agtggatctg taacagattt cactctcacc    240
atcagcagtg tgcaggctga agacctggca gtttattact gtcagaatga ttatagttat    300
ccgtgcacgt tcggaggggg gaccaagctg gaaataaaa                           339

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe

```
                50                  55                  60
Lys Asn Arg Thr Ser Leu Thr Val Asp Thr Ser Thr Thr Ala Tyr
 65                  70                  75                  80

Met His Leu Ala Ser Leu Thr Ser Glu Asp Ser Ala Val Tyr Tyr Cys
                 85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caggtccagc tgcagcagcc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca catcctccac cacagcctac     240
atgcacctcg ccagcctgac atctgaggac tctgcggtct attactgtac aagatggact     300
actgggacgg gagcttattg gggccagggc accaccgtga ccgtgtcctc c              351
```

<210> SEQ ID NO 20
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Val Gln Leu Gln Gln Pro Gly Ser Glu Leu Val Arg Pro Gly Ala
 1               5                  10                  15

Ser Val Lys Leu Ser Cys Lys Ala Ser Gly Tyr Thr Phe Thr Thr Tyr
             20                  25                  30

Trp Met His Trp Val Arg Gln Arg Pro Gly Gln Gly Leu Glu Trp Ile
         35                  40                  45

Gly Asn Ile Tyr Pro Gly Thr Gly Gly Ser Asn Phe Asp Glu Lys Phe
 50                  55                  60

Lys Asn Arg Thr Ser Leu Thr Val Asp Thr Ser Thr Thr Ala Tyr
 65                  70                  75                  80

Met His Leu Ala Ser Leu Thr Ser Glu Asp Ser Ala Val Tyr Tyr Cys
                 85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
            165                 170                 175
Ser Gly Leu Tyr Ser Leu Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
        260                 265                 270
Asn Trp Tyr Val Asp Gly Val Glu Val His Asn Ala Lys Thr Lys Pro
    275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
        340                 345                 350
Glu Glu Met Thr Lys Asn Gln Val Ser Leu Thr Cys Leu Val Lys Gly
    355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
            405                 410                 415
Gly Asn Val Phe Ser Cys Ser Val Met His Glu Ala Leu His Asn His
        420                 425                 430
Tyr Thr Gln Lys Ser Leu Ser Leu Ser Leu Gly Lys
    435                 440

<210> SEQ ID NO 21
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtccagc tgcagcagcc tgggtctgag ctggtgaggc ctggagcttc agtgaagctg     60
tcctgcaagg cgtctggcta cacattcacc acttactgga tgcactgggt gaggcagagg    120
cctggacaag gccttgagtg gattggaaat atttatcctg gtactggtgg ttctaacttc    180
gatgagaagt tcaaaaacag gacctcactg actgtagaca tcctccacac acagcctac    240 atgcacctcg ccagcctgac atctgaggac tctgcggtct attactgtac aagatggact    300
actgggacgg gagcttattg gggccagggc accacgtga ccgtgtcctc cgcttccacc    360
aagggcccat ccgtcttccc cctggcgccc tgctccagga gcacctccga gagcacagcc    420
gccctgggct gcctggtcaa ggactacttc cccgaaccgg tgacggtgtc gtggaactca    480
```

```
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttgagtc caaatatggt    660
cccccatgcc caccgtgccc agcacctgag ttcctggggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtg    960
tccaacaaag gcctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acgcctcccg tgctggactc cgacggctcc   1200
ttcttcctct acagcaggct aaccgtggac aagagcaggt ggcaggaggg gaatgtcttc   1260
tcatgctccg tgatgcatga ggctctgcac aaccactaca cacagaagag cctctccctg   1320
tctctgggta aa                                                       1332
```

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 23
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
caggtccagc tgcagcagtc tgggtctgag ctggtgaggc ctggagcttc agtgaagctg     60
```

-continued

```
tcctgcaagg cgtctggcta cacattcacc acttactgga tgcactgggt gaggcagagg    120
cctggacaag gccttgagtg gattggaaat atttatcctg gtactggtgg ttctaacttc    180
gatgagaagt tcaaaaacag gacctcactg actgtagaca catcctccac cacagcctac    240
atgcacctcg ccagcctgac atctgaggac tctgcggtct attactgtac aagatggact    300
actgggacgg gagcttattg gggccagggc accaccgtga ccgtgtcctc c             351
```

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gln Gly Thr Lys Val Glu Ile
            100                 105                 110

Lys
```

<210> SEQ ID NO 25
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gacattgtga tgacccagtc tccatcctcc ctgactgtga cagcaggaga gaaggtcact    60
atgagctgca agtccagtca gagtctgtta gacagtggaa atcaaaagaa cttcttgacc    120
tggtaccagc agaaaccagg gcagcctcct aaactgttga tcttctgggc atccactagg    180
gaatctgggg tccctgatcg cttcacaggc agtggatctg taacagattt cactctcacc    240
atcagcagtg tgcaggctga agacctggca gtttattact gtcagaatga ttatagttat    300
ccgtgcacgt tcggccaagg gaccaaggtg gaaatcaaa                           339
```

<210> SEQ ID NO 26
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Met Thr Gln Ser Pro Ser Ser Leu Thr Val Thr Ala Gly

```
            1               5                  10                 15
          Glu Lys Val Thr Met Ser Cys Lys Ser Ser Gln Ser Leu Leu Asp Ser
                          20                  25                  30

Gly Asn Gln Lys Asn Phe Leu Thr Trp Tyr Gln Gln Lys Pro Gly Gln
                       35                  40                  45

Pro Pro Lys Leu Leu Ile Phe Trp Ala Ser Thr Arg Glu Ser Gly Val
          50                  55                  60

Pro Asp Arg Phe Thr Gly Ser Gly Ser Val Thr Asp Phe Thr Leu Thr
          65                  70                  75                  80

Ile Ser Ser Val Gln Ala Glu Asp Leu Ala Val Tyr Tyr Cys Gln Asn
                              85                  90                  95

Asp Tyr Ser Tyr Pro Cys Thr Phe Gly Gln Gly Thr Lys Val Glu Ile
                         100                 105                 110

Lys Arg Thr Val Ala Ala Pro Ser Val Phe Ile Phe Pro Pro Ser Asp
                      115                 120                 125

Glu Gln Leu Lys Ser Gly Thr Ala Ser Val Val Cys Leu Leu Asn Asn
          130                 135                 140

Phe Tyr Pro Arg Glu Ala Lys Val Gln Trp Lys Val Asp Asn Ala Leu
          145                 150                 155                 160

Gln Ser Gly Asn Ser Gln Glu Ser Val Thr Glu Gln Asp Ser Lys Asp
                             165                 170                 175

Ser Thr Tyr Ser Leu Ser Ser Thr Leu Thr Leu Ser Lys Ala Asp Tyr
                         180                 185                 190

Glu Lys His Lys Val Tyr Ala Cys Glu Val Thr His Gln Gly Leu Ser
                     195                 200                 205

Ser Pro Val Thr Lys Ser Phe Asn Arg Gly Glu Cys
          210                 215                 220

<210> SEQ ID NO 27
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gacattgtga tgacccagtc tccatcctcc ctgactgtga cagcaggaga gaaggtcact     60
atgagctgca agtccagtca gagtctgtta gacagtggaa atcaaaagaa cttcttgacc    120
tggtaccagc agaaaccagg gcagcctcct aaactgttga tcttctgggc atccactagg    180
gaatctgggg tccctgatcg cttcacaggc agtggatctg taacagattt cactctcacc    240
atcagcagtg tgcaggctga agacctggca gtttattact gtcagaatga ttatagttat    300
ccgtgcacgt tcggccaagg gaccaaggtg gaaatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660

<210> SEQ ID NO 28

<400> SEQUENCE: 28
```

000

<210> SEQ ID NO 29

<400> SEQUENCE: 29

000

<210> SEQ ID NO 30
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

```
Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 31
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
caggtccagc tgcagcagtc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca tcctccacac acagcctac     240
atgcacctcg ccagcctgac atctgaggac tctgcggtct attactgtac aagatggact     300
actgggacgg gagcttattg gggccagggc accacgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga cccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgccccca tcccaggagg atgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctcccctg    1320
```
tctctgggta aa                                                        1332

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Asn Asp Tyr Ser Tyr Pro Tyr Thr
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Tyr Ser Tyr Pro Tyr
1               5

<210> SEQ ID NO 34
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 35
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gacattgtga tgacccagtc tccatcctcc ctgactgtga cagcaggaga gaaggtcact     60
atgagctgca agtccagtca gagtctgtta gacagtggaa atcaaaagaa cttcttgacc    120

```
tggtaccagc agaaaccagg gcagcctcct aaactgttga tcttctgggc atccactagg      180
gaatctgggg tccctgatcg cttcacaggc agtggatctg taacagattt cactctcacc      240
atcagcagtg tgcaggctga agacctggca gtttattact gtcagaatga ttatagttat      300
ccgtacacgt tcggccaagg gaccaaggtg gaaatcaaa                              339
```

<210> SEQ ID NO 36
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 37
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gacattgtga tgacccagtc tccatcctcc ctgactgtga cagcaggaga gaaggtcact      60
atgagctgca agtccagtca gagtctgtta gacagtggaa atcaaaagaa cttcttgacc      120
tggtaccagc agaaaccagg gcagcctcct aaactgttga tcttctgggc atccactagg      180
```

```
gaatctgggg tccctgatcg cttcacaggc agtggatctg taacagattt cactctcacc    240
atcagcagtg tgcaggctga agacctggca gtttattact gtcagaatga ttatagttat    300
ccgtacacgt tcggccaagg gaccaaggtg gaaatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
```

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 39
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
gaagtgcagc tggtgcagtc tggagcagag gtgaaaaagc ccggggagtc tctgaggatc     60
tcctgtaagg gttctggcta cacattcacc acttactgga tgcactgggt gcgacaggcc    120
actggacaag gcttgagtg gatgggtaat atttatcctg gtactggtgg ttctaacttc    180
gatgagaagt tcaagaacag agtcacgatt accgcggaca aatccacgag cacagcctac    240
atggagctga gcagcctgag atctgaggac acggccgtgt attactgtac aagatggact    300
actgggacgg gagcttattg gggccagggc accaccgtga ccgtgtcctc c             351
```

<210> SEQ ID NO 40
<211> LENGTH: 444
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
```

```
                385                 390                 395                 400
            Phe Phe Leu Tyr Ser Arg Leu Thr Val Asp Lys Ser Arg Trp Gln Glu
                            405                 410                 415

Gly Asn Val Phe Ser Cys Ser Val Met His Glu Ala Leu His Asn His
                        420                 425                 430

Tyr Thr Gln Lys Ser Leu Ser Leu Ser Leu Gly Lys
                        435                 440

<210> SEQ ID NO 41
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaagtgcagc tggtgcagtc tggagcagag gtgaaaaagc ccggggagtc tctgaggatc    60
tcctgtaagg gttctggcta cacattcacc acttactgga tgcactgggt gcgacaggcc   120
actggacaag ggcttgagtg gatgggtaat atttatcctg gtactggtgg ttctaacttc   180
gatgagaagt tcaagaacag agtcacgatt accgcggaca aatccacgag cacagcctac   240
atggagctga gcagcctgag atctgaggac acggccgtgt attactgtac aagatggact   300
actgggacgg gagcttattg gggccagggc accaccgtca ccgtgtcctc cgcttccacc   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacgaagac ctacacctgc   600
aacgtagatc acaagcccag caacaccaag gtggacaaga gagttgagtc caaatatggt   660
cccccatgcc caccgtgccc agcacctgag ttcctggggg gaccatcagt cttcctgttc   720
cccccaaaac ccaaggacac tctcatgatc tcccggaccc ctgaggtcac gtgcgtggtg   780
gtggacgtga gccaggaaga ccccgaggtc cagttcaact ggtacgtgga tggcgtggag   840
gtgcataatg ccaagacaaa gccgcgggag gagcagttca acagcacgta ccgtgtggtc   900
agcgtcctca ccgtcctgca ccaggactgg ctgaacggca aggagtacaa gtgcaaggtg   960
tccaacaaag gcctcccgtc ctccatcgag aaaaccatct ccaaagccaa agggcagccc  1020
cgagagccac aggtgtacac cctgcccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct aaccgtggac aagagcaggt ggcaggaggg gaatgtcttc  1260
tcatgctccg tgatgcatga ggctctgcac aaccactaca cacagaagag cctctccctg  1320
tctctgggta aa                                                      1332

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
            35                  40                  45

Ala Pro Arg Leu Leu Ile Tyr Trp Ala Ser Thr Arg Glu Ser Gly Val
        50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gaaattgtgt tgacacagtc tccagccacc ctgtctttgt ctccagggga aagagccacc    60
ctctcctgca gtccagtca gagtctgtta cagtggaa atcaaaagaa cttcttgacc       120
tggtaccagc agaaacctgg ccaggctccc aggctcctca tctattgggc atccactagg   180
gaatctgggg tcccatcaag gttcagcggc agtggatctg ggacagaatt cactctcacc   240
atcagcagcc tgcagcctga tgattttgca acttattact gtcagaatga ttatagttat   300
ccgtacacgt tcggccaagg gaccaaggtg gaaatcaaa                          339

<210> SEQ ID NO 44
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
            35                  40                  45

Ala Pro Arg Leu Leu Ile Tyr Trp Ala Ser Thr Arg Glu Ser Gly Val
        50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
```

```
                115              120              125
Glu Gln Leu Lys Ser Gly Thr Ala Ser Val Val Cys Leu Leu Asn Asn
    130              135              140

Phe Tyr Pro Arg Glu Ala Lys Val Gln Trp Lys Val Asp Asn Ala Leu
145              150              155              160

Gln Ser Gly Asn Ser Gln Glu Ser Val Thr Glu Gln Asp Ser Lys Asp
                165              170              175

Ser Thr Tyr Ser Leu Ser Ser Thr Leu Thr Leu Ser Lys Ala Asp Tyr
            180              185              190

Glu Lys His Lys Val Tyr Ala Cys Glu Val Thr His Gln Gly Leu Ser
        195              200              205

Ser Pro Val Thr Lys Ser Phe Asn Arg Gly Glu Cys
    210              215              220
```

<210> SEQ ID NO 45
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
gaaattgtgt tgacacagtc tccagccacc ctgtctttgt ctccagggga aagagccacc    60
ctctcctgca gtccagtca  gagtctgtta gacagtggaa atcaaaagaa cttcttgacc   120
tggtaccagc agaaacctgg ccaggctccc aggctcctca tctattgggc atccactagg   180
gaatctgggg tcccatcaag gttcagcggc agtggatctg ggacagaatt cactctcacc   240
atcagcagcc tgcagcctga tgattttgca acttattact gtcagaatga ttatagttat   300
ccgtacacgt tcggccaagg gaccaaggtg gaaatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
```

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Pro Arg Phe Ser Gly Ser Gly Tyr Gly Thr Asp Phe Thr Leu Thr
65                  70                  75                  80
```

| Ile | Asn | Asn | Ile | Glu | Ser | Glu | Asp | Ala | Ala | Tyr | Tyr | Phe | Cys | Gln | Asn |
|---|---|---|---|---|---|---|---|---|---|---|---|---|---|---|---|
| | | | | 85 | | | | 90 | | | | | 95 | | |

| Asp | Tyr | Ser | Tyr | Pro | Tyr | Thr | Phe | Gly | Gln | Gly | Thr | Lys | Val | Glu | Ile |
|---|---|---|---|---|---|---|---|---|---|---|---|---|---|---|---|
| | | | 100 | | | | | 105 | | | | | 110 | | |

Lys

<210> SEQ ID NO 47
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
gacatccaga tgacccagtc tccatcctcc ctgtctgcat ctgtaggaga cagagtcacc      60
atcacttgca agtccagtca gagtctgtta gacagtggaa atcaaaagaa cttcttgacc     120
tggtaccagc agaaacctgg ccaggctccc aggctcctca tctattgggc atccactagg     180
gaatctggga tcccacctcg attcagtggc agcgggtatg gaacagattt taccctcaca     240
attaataaca tagaatctga ggatgctgca tattacttct gtcagaatga ttatagttat     300
ccgtacacgt tcggccaagg gaccaaggtg gaaatcaaa                            339
```

<210> SEQ ID NO 48
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Lys | Ser | Ser | Gln | Ser | Leu | Leu | Asp | Ser |
|---|---|---|---|---|---|---|---|---|---|---|---|---|---|---|---|
| | | | 20 | | | | | 25 | | | | | 30 | | |

| Gly | Asn | Gln | Lys | Asn | Phe | Leu | Thr | Trp | Tyr | Gln | Gln | Lys | Pro | Gly | Gln |
|---|---|---|---|---|---|---|---|---|---|---|---|---|---|---|---|
| | | | 35 | | | | | 40 | | | | | 45 | | |

| Ala | Pro | Arg | Leu | Leu | Ile | Tyr | Trp | Ala | Ser | Thr | Arg | Glu | Ser | Gly | Ile |
|---|---|---|---|---|---|---|---|---|---|---|---|---|---|---|---|
| | 50 | | | | | 55 | | | | | 60 | | | | |

| Pro | Pro | Arg | Phe | Ser | Gly | Ser | Gly | Tyr | Gly | Thr | Asp | Phe | Thr | Leu | Thr |
|---|---|---|---|---|---|---|---|---|---|---|---|---|---|---|---|
| 65 | | | | | 70 | | | | | 75 | | | | | 80 |

| Ile | Asn | Asn | Ile | Glu | Ser | Glu | Asp | Ala | Ala | Tyr | Tyr | Phe | Cys | Gln | Asn |
|---|---|---|---|---|---|---|---|---|---|---|---|---|---|---|---|
| | | | | 85 | | | | 90 | | | | | 95 | | |

| Asp | Tyr | Ser | Tyr | Pro | Tyr | Thr | Phe | Gly | Gln | Gly | Thr | Lys | Val | Glu | Ile |
|---|---|---|---|---|---|---|---|---|---|---|---|---|---|---|---|
| | | | 100 | | | | | 105 | | | | | 110 | | |

| Lys | Arg | Thr | Val | Ala | Ala | Pro | Ser | Val | Phe | Ile | Phe | Pro | Pro | Ser | Asp |
|---|---|---|---|---|---|---|---|---|---|---|---|---|---|---|---|
| | | 115 | | | | | 120 | | | | | 125 | | | |

| Glu | Gln | Leu | Lys | Ser | Gly | Thr | Ala | Ser | Val | Val | Cys | Leu | Leu | Asn | Asn |
|---|---|---|---|---|---|---|---|---|---|---|---|---|---|---|---|
| | 130 | | | | | 135 | | | | | 140 | | | | |

| Phe | Tyr | Pro | Arg | Glu | Ala | Lys | Val | Gln | Trp | Lys | Val | Asp | Asn | Ala | Leu |
|---|---|---|---|---|---|---|---|---|---|---|---|---|---|---|---|
| 145 | | | | | 150 | | | | | 155 | | | | | 160 |

| Gln | Ser | Gly | Asn | Ser | Gln | Glu | Ser | Val | Thr | Glu | Gln | Asp | Ser | Lys | Asp |
|---|---|---|---|---|---|---|---|---|---|---|---|---|---|---|---|
| | | | | 165 | | | | 170 | | | | | 175 | | |

| Ser | Thr | Tyr | Ser | Leu | Ser | Ser | Thr | Leu | Thr | Leu | Ser | Lys | Ala | Asp | Tyr |
|---|---|---|---|---|---|---|---|---|---|---|---|---|---|---|---|
| | | | 180 | | | | | 185 | | | | | 190 | | |

| Glu | Lys | His | Lys | Val | Tyr | Ala | Cys | Glu | Val | Thr | His | Gln | Gly | Leu | Ser |
|---|---|---|---|---|---|---|---|---|---|---|---|---|---|---|---|

Ser Pro Val Thr Lys Ser Phe Asn Arg Gly Glu Cys
    210                 215                 220

<210> SEQ ID NO 49
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gacatccaga tgacccagtc tccatcctcc ctgtctgcat ctgtaggaga cagagtcacc      60
atcacttgca agtccagtca gagtctgtta gacagtggaa atcaaaagaa cttcttgacc     120
tggtaccagc agaaacctgg ccaggctccc aggctcctca tctattgggc atccactagg     180
gaatctggga tcccacctcg attcagtggc agcgggtatg gaacagattt taccctcaca     240
attaataaca tagaatctga ggatgctgca tattacttct gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 51
<211> LENGTH: 351
<212> TYPE: DNA
<213> ORGANISM: Artificial Sequence
<220> FEATURE:

<223> OTHER INFORMATION: Description of Artificial Sequence: Synthetic
     polynucleotide

<400> SEQUENCE: 51

```
gaagtgcagc tggtgcagtc tggagcagag gtgaaaaagc ccggggagtc tctgaggatc    60
tcctgtaagg gttctggcta cacattcacc acttactgga tgcactggat caggcagtcc   120
ccatcgagag gccttgagtg gctgggtaat atttatcctg gtactggtgg ttctaacttc   180
gatgagaagt tcaagaacag attcaccatc tccagagaca attccaagaa cacgctgtat   240
cttcaaatga acagcctgag agccgaggac acggccgtgt attactgtac aagatggact   300
actgggacgg gagcttattg gggccagggc accaccgtga ccgtgtcctc c            351
```

<210> SEQ ID NO 52
<211> LENGTH: 444
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 52

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270
```

```
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
        290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys
        435                 440

<210> SEQ ID NO 53
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaagtgcagc tggtgcagtc tggagcagag gtgaaaaagc ccggggagtc tctgaggatc        60
tcctgtaagg gttctggcta cacattcacc acttactgga tgcactggat caggcagtcc       120
ccatcgagag gccttgagtg gctgggtaat atttatcctg gtactggtgg ttctaacttc       180
gatgagaagt tcaagaacag attcaccatc tccagagaca attccaagaa cacgctgtat       240
cttcaaatga cagcctgag agccgaggac acggccgtgt attactgtac aagatggact       300
actgggacgg gagcttattg gggccagggc accaccgtga ccgtgtcctc cgcttccacc       360
aagggcccat ccgtcttccc cctggcgccc tgctccagga gcacctccga gagcacagcc       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacgaagac ctacacctgc       600
aacgtagatc acaagcccag caacaccaag gtggacaaga gagttgagtc caaatatggt       660
cccccatgcc caccgtgccc agcacctgag ttcctggggg gaccatcagt cttcctgttc       720
cccccaaaac ccaaggacac tctcatgatc tcccggaccc ctgaggtcac gtgcgtggtg       780
gtggacgtga gccaggaaga cccccgaggtc cagttcaact ggtacgtgga tggcgtggag       840
gtgcataatg ccaagacaaa gccgcgggag gagcagttca acagcacgta ccgtgtggtc       900
agcgtcctca ccgtcctgca ccaggactgg ctgaacggca aggagtacaa gtgcaaggtg       960
tccaacaaag gcctcccgtc ctccatcgag aaaaccatct ccaaagccaa agggcagccc      1020
cgagagccac aggtgtacac cctgccccca tcccaggagg agatgaccaa gaaccaggtc      1080
```

```
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                       1332
```

<210> SEQ ID NO 54
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 55
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gaaattgtgt tgacacagtc tccagccacc ctgtctttgt ctccagggga aagagccacc     60
ctctcctgca gtccagtca gagtctgtta gacagtggaa atcaaaagaa cttcttgacc    120
tggtatcagc agaaaccagg gaaagctcct aagctcctga tctattgggc atccactagg    180
gaatctgggg tcccatcaag gttcagtgga agtggatctg ggacagattt tactttcacc    240
atcagcagcc tgcagcctga agatattgca acatattact gtcagaatga ttatagttat    300
ccgtacacgt tcggccaagg gaccaaggtg gaaatcaaa                           339
```

<210> SEQ ID NO 56
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 57
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gaaattgtgt tgacacagtc tccagccacc ctgtctttgt ctccagggga aagagccacc      60
ctctcctgca gtccagtca gagtctgtta gacagtggaa atcaaaagaa cttcttgacc     120
tggtatcagc agaaaccagg gaaagctcct aagctcctga tctattgggc atccactagg     180
gaatctgggg tcccatcaag gttcagtgga agtggatctg ggacagattt tactttcacc     240
atcagcagcc tgcagcctga agatattgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660

<210> SEQ ID NO 58
<211> LENGTH: 113
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 58

```
Asp Ile Val Met Thr Gln Thr Pro Leu Ser Leu Pro Val Thr Pro Gly
 1               5                  10                  15
Glu Pro Ala Ser Ile Ser Cys Lys Ser Ser Gln Ser Leu Leu Asp Ser
             20                  25                  30
Gly Asn Gln Lys Asn Phe Leu Thr Trp Tyr Gln Gln Lys Pro Gly Gln
         35                  40                  45
Ala Pro Arg Leu Leu Ile Tyr Trp Ala Ser Thr Arg Glu Ser Gly Val
     50                  55                  60
Pro Ser Arg Phe Ser Gly Ser Gly Ser Gly Thr Asp Phe Thr Phe Thr
 65                  70                  75                  80
Ile Ser Ser Leu Glu Ala Glu Asp Ala Ala Thr Tyr Tyr Cys Gln Asn
                 85                  90                  95
Asp Tyr Ser Tyr Pro Tyr Thr Phe Gly Gln Gly Thr Lys Val Glu Ile
            100                 105                 110
Lys
```

<210> SEQ ID NO 59
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
gatattgtga tgacccagac tccactctcc ctgcccgtca cccctggaga gccggcctcc    60
atctcctgca gtccagtca gagtctgtta gacagtggaa atcaaaagaa cttcttgacc   120
tggtaccagc agaaacctgg ccaggctccc aggctcctca tctattgggc atccactagg   180
gaatctgggg tccctcgag gttcagtggc agtggatctg ggacagattt cacctttacc   240
atcagtagcc tggaagctga agatgctgca acatattact gtcagaatga ttatagttat   300
ccgtacacgt tcggccaagg gaccaaggtg gaaatcaaa                          339
```

<210> SEQ ID NO 60
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Asp Ile Val Met Thr Gln Thr Pro Leu Ser Leu Pro Val Thr Pro Gly
 1               5                  10                  15
Glu Pro Ala Ser Ile Ser Cys Lys Ser Ser Gln Ser Leu Leu Asp Ser
             20                  25                  30
Gly Asn Gln Lys Asn Phe Leu Thr Trp Tyr Gln Gln Lys Pro Gly Gln
         35                  40                  45
Ala Pro Arg Leu Leu Ile Tyr Trp Ala Ser Thr Arg Glu Ser Gly Val
     50                  55                  60
Pro Ser Arg Phe Ser Gly Ser Gly Ser Gly Thr Asp Phe Thr Phe Thr
 65                  70                  75                  80
```

```
Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 61
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gatattgtga tgacccagac tccactctcc ctgcccgtca cccctggaga gccggcctcc      60
atctcctgca gtccagtca gagtctgtta cacagtggaa atcaaaagaa cttcttgacc     120
tggtaccagc agaaacctgg ccaggctccc aggctcctca tctattgggc atccactagg     180
gaatctgggg tccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45
```

```
Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Phe Thr
 65                  70                  75                  80

Ile Ser Ser Leu Glu Ala Glu Asp Ala Ala Thr Tyr Tyr Cys Gln Asn
                 85                  90                  95

Asp Tyr Ser Tyr Pro Tyr Thr Phe Gly Gln Gly Thr Lys Val Glu Ile
                100                 105                 110

Lys
```

<210> SEQ ID NO 63
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaaattgtgt tgacacagtc tccagccacc ctgtctttgt ctccagggga aagagccacc    60
ctctcctgca gtccagtca gagtctgtta gacagtggaa atcaaaagaa cttcttgacc   120
tggtatcagc agaaaccagg gaaagctcct aagctcctga tctattgggc atccactagg   180
gaatctgggg tccctcgag gttcagtggc agtggatctg ggacagattt cacctttacc   240
atcagtagcc tggaagctga agatgctgca acatattact gtcagaatga ttatagttat   300
ccgtacacgt tcggccaagg gaccaaggtg gaaatcaaa                           339
```

<210> SEQ ID NO 64
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Glu Ile Val Leu Thr Gln Ser Pro Ala Thr Leu Ser Leu Ser Pro Gly
 1               5                  10                  15

Glu Arg Ala Thr Leu Ser Cys Lys Ser Ser Gln Ser Leu Leu Asp Ser
             20                  25                  30

Gly Asn Gln Lys Asn Phe Leu Thr Trp Tyr Gln Gln Lys Pro Gly Lys
         35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Phe Thr
 65                  70                  75                  80

Ile Ser Ser Leu Glu Ala Glu Asp Ala Ala Thr Tyr Tyr Cys Gln Asn
                 85                  90                  95

Asp Tyr Ser Tyr Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

```
<210> SEQ ID NO 65
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gaaattgtgt tgacacagtc tccagccacc ctgtctttgt ctccagggga aagagccacc      60
ctctcctgca agtccagtca gagtctgtta gacagtggaa atcaaaagaa cttcttgacc     120
tggtatcagc agaaaccagg gaaagctcct aagctcctga tctattgggc atccactagg     180
gaatctgggg tcccctcgag gttcagtggc agtggatctg gacagattt caccttaccc     240 atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

```
<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Ile Val Leu Thr Gln Ser Pro Asp Phe Gln Ser Val Thr Pro Lys
1               5                   10                  15

Glu Lys Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 67
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gaaattgtgc tgactcagtc tccagacttt cagtctgtga ctccaaagga gaaagtcacc      60
atcacctgca agtccagtca gagtctgtta gacagtggaa atcaaaagaa cttcttgacc     120
tggtaccagc agaaacctgg ccaggctccc aggctcctca tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaa                            339
```

<210> SEQ ID NO 68
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Glu Ile Val Leu Thr Gln Ser Pro Asp Phe Gln Ser Val Thr Pro Lys
1               5                   10                  15

Glu Lys Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 69
<211> LENGTH: 660

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gaaattgtgc tgactcagtc tccagacttt cagtctgtga ctccaaagga gaaagtcacc      60
atcacctgca gtccagtca gagtctgtta gacagtggaa atcaaaagaa cttcttgacc      120
tggtaccagc agaaacctgg ccaggctccc aggctcctca tctattgggc atccactagg    180
gaatctgggg tcccctcgag gttcagtggc agtggatctg ggacagattt caccttttacc  240
atcagtagcc tggaagctga agatgctgca acatattact gtcagaatga ttatagttat    300
ccgtacacgt tcggccaagg gaccaaggtg gaaatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt   660
```

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Glu Ile Val Leu Thr Gln Ser Pro Ala Thr Leu Ser Leu Ser Pro Gly
1               5                   10                  15
Glu Arg Ala Thr Leu Ser Cys Lys Ser Ser Gln Ser Leu Leu Asp Ser
            20                  25                  30
Gly Asn Gln Lys Asn Phe Leu Thr Trp Tyr Gln Gln Lys Pro Gly Gln
        35                  40                  45
Ala Pro Arg Leu Leu Ile Tyr Trp Ala Ser Thr Arg Glu Ser Gly Val
    50                  55                  60
Pro Ser Arg Phe Ser Gly Ser Gly Ser Gly Thr Asp Phe Thr Phe Thr
65                  70                  75                  80
Ile Ser Ser Leu Glu Ala Glu Asp Ala Ala Thr Tyr Tyr Cys Gln Asn
                85                  90                  95
Asp Tyr Ser Tyr Pro Tyr Thr Phe Gly Gln Gly Thr Lys Val Glu Ile
            100                 105                 110
Lys
```

<210> SEQ ID NO 71
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gaaattgtgt tgacacagtc tccagccacc ctgtctttgt ctccagggga aagagccacc      60
ctctcctgca gtccagtca gagtctgtta gacagtggaa atcaaaagaa cttcttgacc    120
```

```
tggtaccagc agaaacctgg ccaggctccc aggctcctca tctattgggc atccactagg    180
gaatctgggg tcccctcgag gttcagtggc agtggatctg ggacagattt cacctttacc    240
atcagtagcc tggaagctga agatgctgca acatattact gtcagaatga ttatagttat    300
ccgtacacgt tcggccaagg gaccaaggtg gaaatcaaa                            339
```

<210> SEQ ID NO 72
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 73
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
gaaattgtgt tgacacagtc tccagccacc ctgtctttgt ctccagggga aagagccacc    60
ctctcctgca gtccagtca gagtctgtta gacagtggaa atcaaaagaa cttcttgacc    120
tggtaccagc agaaacctgg ccaggctccc aggctcctca tctattgggc atccactagg    180
gaatctgggg tcccctcgag gttcagtggc agtggatctg ggacagattt cacctttacc    240
```

-continued

```
atcagtagcc tggaagctga agatgctgca acatattact gtcagaatga ttatagttat      300
ccgtacacgt tcggccaagg gaccaaggtg gaaatcaaac gtacggtggc tgcaccatct      360
gtcttcatct cccgccatc tgatgagcag ttgaaatctg gaactgcctc tgttgtgtgc       420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
```

```
<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

```
<210> SEQ ID NO 75
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gacatccaga tgacccagtc tccatcctcc ctgtctgcat ctgtaggaga cagagtcacc      60
atcacttgca agtccagtca gagtctgtta gacagtggaa atcaaaagaa cttcttgacc      120
tggtacctgc agaagccagg gcagtctcca cagctcctga tctattgggc atccactagg      180
gaatctgggg tcccctcgag gttcagtggc agtggatctg ggacagattt cacctttacc      240
atcagtagcc tggaagctga agatgctgca acatattact gtcagaatga ttatagttat      300
ccgtacacgt tcggccaagg gaccaaggtg gaaatcaaa                             339
```

```
<210> SEQ ID NO 76
<211> LENGTH: 220
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 76

| | | | | | | | | | | | | | | |
|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Lys | Ser | Ser | Gln | Ser | Leu | Leu | Asp | Ser |
| | | | 20 | | | | | 25 | | | | | 30 | | |
| Gly | Asn | Gln | Lys | Asn | Phe | Leu | Thr | Trp | Tyr | Leu | Gln | Lys | Pro | Gly | Gln |
| | | | 35 | | | | | 40 | | | | | 45 | | |
| Ser | Pro | Gln | Leu | Leu | Ile | Tyr | Trp | Ala | Ser | Thr | Arg | Glu | Ser | Gly | Val |
| | 50 | | | | | 55 | | | | | 60 | | | | |
| Pro | Ser | Arg | Phe | Ser | Gly | Ser | Gly | Ser | Gly | Thr | Asp | Phe | Thr | Phe | Thr |
| 65 | | | | 70 | | | | | 75 | | | | | 80 | |
| Ile | Ser | Ser | Leu | Glu | Ala | Glu | Asp | Ala | Ala | Thr | Tyr | Tyr | Cys | Gln | Asn |
| | | | | 85 | | | | | 90 | | | | | 95 | |
| Asp | Tyr | Ser | Tyr | Pro | Tyr | Thr | Phe | Gly | Gln | Gly | Thr | Lys | Val | Glu | Ile |
| | | | 100 | | | | | 105 | | | | | 110 | | |
| Lys | Arg | Thr | Val | Ala | Ala | Pro | Ser | Val | Phe | Ile | Phe | Pro | Pro | Ser | Asp |
| | | | 115 | | | | | 120 | | | | | 125 | | |
| Glu | Gln | Leu | Lys | Ser | Gly | Thr | Ala | Ser | Val | Val | Cys | Leu | Leu | Asn | Asn |
| | 130 | | | | | 135 | | | | | 140 | | | | |
| Phe | Tyr | Pro | Arg | Glu | Ala | Lys | Val | Gln | Trp | Lys | Val | Asp | Asn | Ala | Leu |
| 145 | | | | | 150 | | | | | 155 | | | | | 160 |
| Gln | Ser | Gly | Asn | Ser | Gln | Glu | Ser | Val | Thr | Glu | Gln | Asp | Ser | Lys | Asp |
| | | | | 165 | | | | | 170 | | | | | 175 | |
| Ser | Thr | Tyr | Ser | Leu | Ser | Ser | Thr | Leu | Thr | Leu | Ser | Lys | Ala | Asp | Tyr |
| | | | 180 | | | | | 185 | | | | | 190 | | |
| Glu | Lys | His | Lys | Val | Tyr | Ala | Cys | Glu | Val | Thr | His | Gln | Gly | Leu | Ser |
| | | | 195 | | | | | 200 | | | | | 205 | | |
| Ser | Pro | Val | Thr | Lys | Ser | Phe | Asn | Arg | Gly | Glu | Cys | | | | |
| | 210 | | | | | 215 | | | | | 220 | | | | |

<210> SEQ ID NO 77
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
gacatccaga tgacccagtc tccatcctcc ctgtctgcat ctgtaggaga cagagtcacc      60
atcacttgca agtccagtca gagtctgtta cagtggaa atcaaaagaa cttcttgacc     120
tggtacctgc agaagccagg gcagtctcca cagctcctga tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 78
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 79
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
gatgttgtga tgactcagtc tccactctcc ctgcccgtca cccttggaca gccggcctcc    60
atctcctgca gtccagtca gagtctgtta cacagtggaa atcaaaagaa cttcttaacc    120
tggtatcagc agaaaccagg gaaagctcct aagctcctga tctattgggc atccactagg    180
gaatctgggg tccctcgag gttcagtggc agtggatctg ggacagattt cacctttacc    240
atcagtagcc tggaagctga agatgctgca acatattact gtcagaatga ttatagttat    300
ccgtacacgt tcggccaagg gaccaaggtg gaaatcaaa                           339
```

<210> SEQ ID NO 80
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60
```

```
Pro Ser Arg Phe Ser Gly Ser Gly Ser Gly Thr Asp Phe Thr Phe Thr
 65                  70                  75                  80

Ile Ser Ser Leu Glu Ala Glu Asp Ala Ala Thr Tyr Tyr Cys Gln Asn
                 85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 81
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gatgttgtga tgactcagtc tccactctcc ctgcccgtca cccttggaca gccggcctcc    60
atctcctgca gtccagtca gagtctgtta cagagtggaa atcaaaagaa cttcttaacc   120
tggtatcagc agaaaccagg gaaagctcct aagctcctga tctattgggc atccactagg   180
gaatctgggg tcccctcgag gttcagtggc agtggatctg ggacagattt caccttacc   240 atcagtagcc tggaagctga agatgctgca acatattact gtcagaatga ttatagttat   300
ccgtacacgt tcggccaagg gaccaaggtg gaaatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600 gaagtcaccc atcagggcct gagctcgccc gtcacaaaga gcttcaacag gggagagtgt   660

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Thr Tyr
```

```
            20                  25                  30
Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 83
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggttcagc tggtgcagtc tggagctgag gtgaagaagc ctggggcctc agtgaaggtc      60
tcctgcaagg cttctggcta cacattcacc acttactgga tgcactggat caggcagtcc    120
ccatcgagag gccttgagtg gctgggtaat atttatcctg gtactggtgg ttctaacttc    180
gatgagaagt tcaagaacag attcaccatc tccagagaca attccaagaa cacgctgtat    240
cttcaaatga acagcctgag agccgaggac acggccgtgt attactgtac aagatggact    300
actgggacgg gagcttactg gggccaggqc accaccgtga ccgtgtcctc c             351

<210> SEQ ID NO 84
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 85
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
caggttcagc tggtgcagtc tggagctgag gtgaagaagc ctggggcctc agtgaaggtc    60
tcctgcaagg cttctggcta cacattcacc acttactgga tgcactggat caggcagtcc   120
ccatcgagag gccttgagtg gctgggtaat atttatcctg gtactggtgg ttctaacttc   180
gatgagaagt tcaagaacag attcaccatc tccagagaca attccaagaa cacgctgtat   240
cttcaaatga acagcctgag agccgaggac acggccgtgt attactgtac aagatggact   300

```
actgggacgg gagcttactg gggccagggc accaccgtga ccgtgtcctc cgcttccacc   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacgaagac ctacacctgc   600
aacgtagatc acaagcccag caacaccaag gtggacaaga gagttgagtc caaatatggt   660
cccccatgcc caccgtgccc agcacctgag ttcctggggg gaccatcagt cttcctgttc   720
cccccaaaac ccaaggacac tctcatgatc tcccggaccc ctgaggtcac gtgcgtggtg   780
gtggacgtga gccaggaaga ccccgaggtc cagttcaact ggtacgtgga tggcgtggag   840
gtgcataatg ccaagacaaa gccgcgggag gagcagttca acagcacgta ccgtgtggtc   900
agcgtcctca ccgtcctgca ccaggactgg ctgaacggca aggagtacaa gtgcaaggtg   960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct aaccgtggac aagagcaggt ggcaggaggg gaatgtcttc  1260
tcatgctccg tgatgcatga ggctctgcac aaccactaca cacagaagag cctctcc ctg  1320
tctctgggta aa                                                      1332

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 87
<211> LENGTH: 351
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 87

```
gaagtgcagc tggtgcagtc tggagcagag gtgaaaaagc ccggggagtc tctgaggatc      60
tcctgtaagg gttctggcta cacattcacc acttactgga tgcactgggt gcgacaggcc     120
cctggacaag ggcttgagtg gatgggtaat atttatcctg gtactggtgg ttctaacttc     180
gatgagaagt tcaagaacag attcaccatc tccagagaca attccaagaa cacgctgtat     240
cttcaaatga acagcctgag agccgaggac acggccgtgt attactgtac aagatggact     300
actgggacgg gagcttattg gggccagggc accaccgtga ccgtgtcctc c              351
```

<210> SEQ ID NO 88
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
```

```
                275                 280                 285
Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440
```

<210> SEQ ID NO 89
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
gaagtgcagc tggtgcagtc tggagcagag gtgaaaaagc ccggggagtc tctgaggatc    60
tcctgtaagg gttctggcta cattcacc   acttactgga tgcactgggt gcgacaggcc   120
cctggacaag gcttgagtg  gatgggtaat atttatcctg gtactggtgg ttctaacttc   180
gatgagaagt tcaagaacag attcaccatc tccagagaca attccaagaa cacgctgtat   240
cttcaaatga acagcctgag agccgaggac acggccgtgt attactgtac aagatggact   300
actgggacgg gagcttattg gggccagggc accaccgtga ccgtgtcctc cgcttccacc   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacgaagac ctacacctgc   600
aacgtagatc acaagcccag caacaccaag gtggacaaga gagttgagtc caaatatggt   660
cccccatgcc caccgtgccc agcacctgag ttcctggggg gaccatcagt cttcctgttc   720
cccccaaaac ccaaggacac tctcatgatc tcccggaccc ctgaggtcac gtgcgtggtg   780
gtggacgtga gccaggaaga ccccgaggtc cagttcaact ggtacgtgga tggcgtggag   840
gtgcataatg ccaagacaaa gccgcgggag gagcagttca acagcacgta ccgtgtggtc   900
agcgtcctca ccgtcctgca ccaggactgg ctgaacggca aggagtacaa gtgcaaggtg   960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
```

-continued

```
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                        1332
```

<210> SEQ ID NO 90
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
gaagtgcagc tggtgcagtc tggcgccgaa gtgaagaagc ctggcgagtc cctgcggatc     60
tcctgcaagg gctctggcta caccttcacc acctactgga tgcactgggt gcgacaggct    120
accggccagg gcctggaatg gatgggcaac atctatcctg gcaccggcgg ctccaacttc    180
gacgagaagt tcaagaacag agtgaccatc accgccgaca gtccacctc caccgcctac    240 atggaactgt cctccctgag atccgaggac accgccgtgt actactgcac ccggtggaca    300
accggcacag gcgcttattg gggccagggc accacagtga ccgtgtcctc t             351
```

<210> SEQ ID NO 91
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 92
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gaagtgcagc tggtgcagtc tggcgccgaa gtgaagaagc ctggcgagtc cctgcggatc      60
tcctgcaagg gctctggcta caccttcacc acctactgga tgcactgggt gcgacaggct     120
accggccagg gcctggaatg gatgggcaac atctatcctg gcaccggcgg ctccaacttc     180
gacgagaagt tcaagaacag agtgaccatc accgccgaca gtccacctc accgcctac       240 atggaactgt cctccctgag atccgaggac accgccgtgt actactgcac ccggtggaca     300
accggcacag cgcttattg gggccagggc accacagtga ccgtgtcctc tgcttctacc      360
aagggcccca gcgtgttccc cctggccccc tgctccagaa gcaccagcga gagcacagcc     420
gccctgggct gcctggtgaa ggactacttc cccgagcccg tgaccgtgtc ctggaacagc     480
ggagccctga ccagcggcgt gcacaccttc cccgccgtgc tgcagagcag cggcctgtac     540
agcctgagca gcgtggtgac cgtgcccagc agcagcctgg gcaccaagac ctacacctgt     600
```

```
aacgtggacc acaagcccag caacaccaag gtggacaaga gggtggagag caagtacggc    660
ccaccctgcc cccctgccc agccccgag ttcctgggcg acccagcgt gttcctgttc       720
cccccaagc ccaaggacac cctgatgatc agcagaaccc ccgaggtgac ctgtgtggtg    780
gtggacgtgt cccaggagga ccccgaggtc cagttcaact ggtacgtgga cggcgtggag    840
gtgcacaacg ccaagaccaa gcccagagag gagcagttta acagcaccta ccgggtggtg    900
tccgtgctga ccgtgctgca ccaggactgg ctgaacggca agagtacaa gtgtaaggtc     960
tccaacaagg gcctgccaag cagcatcgaa aagaccatca gcaaggccaa gggccagcct   1020
agagagcccc aggtctacac cctgccaccc agccaagagg agatgaccaa gaaccaggtg   1080
tccctgacct gtctggtgaa gggcttctac ccaagcgaca tcgccgtgga gtgggagagc   1140
aacggccagc ccgagaacaa ctacaagacc acccccccag tgctggacag cgacggcagc   1200
ttcttcctgt acagcaggct gaccgtggac aagtccagat ggcaggaggg caacgtcttt   1260
agctgctccg tgatgcacga ggccctgcac aaccactaca cccagaagag cctgagcctg   1320
tccctgggc                                                           1329

<210> SEQ ID NO 93
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gagatcgtgc tgacccagtc ccctgccacc ctgtcactgt ctccaggcga gagagctacc      60
ctgtcctgca gtcctcccca gtccctgctg gactccggca accagaagaa cttcctgacc    120
tggtatcagc agaagcccgg ccaggccccc agactgctga tctactgggc ctccacccgg    180
gaatctggcg tgccctctag attctccggc tccggctctg gcaccgagtt taccctgacc    240
atctccagcc tgcagcccga cgacttcgcc acctactact gccagaacga ctactcctac    300
ccctacacct tcggccaggg caccaaggtg gaaatcaag                           339

<210> SEQ ID NO 94
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gagatcgtgc tgacccagtc ccctgccacc ctgtcactgt ctccaggcga gagagctacc      60
ctgtcctgca gtcctcccca gtccctgctg gactccggca accagaagaa cttcctgacc    120
tggtatcagc agaagcccgg ccaggccccc agactgctga tctactgggc ctccacccgg    180
gaatctggcg tgccctctag attctccggc tccggctctg gcaccgagtt taccctgacc    240
atctccagcc tgcagcccga cgacttcgcc acctactact gccagaacga ctactcctac    300
ccctacacct tcggccaggg caccaaggtg gaaatcaagc gtacggtggc cgctcccagc    360
gtgttcatct tccccccaag cgacgagcag ctgaagagcg gcaccgccag cgtggtgtgt    420
ctgctgaaca acttctaccc cagggaggcc aaggtgcagt ggaaggtgga caacgccctg    480
cagagcggca acagccagga gagcgtcacc gagcaggaca gcaaggactc cacctacagc    540
```

| | |
|---|---:|
| ctgagcagca ccctgaccct gagcaaggcc gactacgaga agcacaaggt gtacgcctgt | 600 |
| gaggtgaccc accagggcct gtccagcccc gtgaccaaga gcttcaacag gggcgagtgc | 660 |

<210> SEQ ID NO 95
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

| | |
|---|---:|
| gaggtgcagc tggtgcagtc aggcgccgaa gtgaagaagc ccggcgagtc actgagaatt | 60 |
| agctgtaaag gttcaggcta caccttcact acctactgga tgcactgggt ccgccaggct | 120 |
| accggtcaag gcctcgagtg gatgggtaat atctaccccg gcaccggcgg ctctaacttc | 180 |
| gacgagaagt ttaagaatag agtgactatc accgccgata agtctactag caccgcctat | 240 |
| atggaactgt ctagcctgag atcagaggac accgccgtct actactgcac taggtggact | 300 |
| accggcacag gcgcctactg gggtcaaggc actaccgtga ccgtgtctag c | 351 |

<210> SEQ ID NO 96
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

| | |
|---|---:|
| gaggtgcagc tggtgcagtc aggcgccgaa gtgaagaagc ccggcgagtc actgagaatt | 60 |
| agctgtaaag gttcaggcta caccttcact acctactgga tgcactgggt ccgccaggct | 120 |
| accggtcaag gcctcgagtg gatgggtaat atctaccccg gcaccggcgg ctctaacttc | 180 |
| gacgagaagt ttaagaatag agtgactatc accgccgata agtctactag caccgcctat | 240 |
| atggaactgt ctagcctgag atcagaggac accgccgtct actactgcac taggtggact | 300 |
| accggcacag gcgcctactg gggtcaaggc actaccgtga ccgtgtctag cgctagcact | 360 |
| aagggcccgt ccgtgttccc cctggcacct tgtagccgga gcactagcga atccaccgct | 420 |
| gccctcggct gcctggtcaa ggattacttc ccggagcccg tgaccgtgtc ctggaacagc | 480 |
| ggagccctga cctccggagt gcacaccttc cccgctgtgc tgcagagctc cgggctgtac | 540 |
| tcgctgtcgt cggtggtcac ggtgccttca tctagcctgg gtaccaagac ctacacttgc | 600 |
| aacgtggacc acaagccttc caacactaag gtggacaagc gcgtcgaatc gaagtacggc | 660 |
| ccaccgtgcc cgccttgtcc cgcgccggag ttcctcggcg gtccctcggt ctttctgttc | 720 |
| ccaccgaagc ccaaggacac tttgatgatt tcccgcaccc ctgaagtgac atgcgtggtc | 780 |
| gtggacgtgt cacaggaaga tccggaggtg cagttcaatt ggtacgtgga tggcgtcgag | 840 |
| gtgcacaacg ccaaaaccaa gccgagggag gagcagttca actccactta ccgcgtcgtg | 900 |
| tccgtgctga cggtgctgca tcaggactgg ctgaacggga aggagtacaa gtgcaaagtg | 960 |
| tccaacaagg gacttcctag ctcaatcgaa aagaccatct cgaaagccaa gggacagccc | 1020 |
| cgggaacccc aagtgtatac cctgccaccg agccaggaag aaatgactaa gaaccaagtc | 1080 |
| tcattgactt gccttgtgaa gggcttctac ccatcggata tcgccgtgga atgggagtcc | 1140 |
| aacggccagc cggaaaacaa ctacaagacc acccctccgg tgctggactc agacggatcc | 1200 |
| ttcttcctct actcgcggct gaccgtggat aagagcagat ggcaggaggg aaatgtgttc | 1260 |

```
agctgttctg tgatgcatga agccctgcac aaccactaca ctcagaagtc cctgtccctc    1320
tccctggga                                                            1329
```

<210> SEQ ID NO 97
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
gagatcgtcc tgactcagtc acccgctacc ctgagcctga gccctggcga gcgggctaca     60
ctgagctgta aatctagtca gtcactgctg gatagcggta atcagaagaa cttcctgacc    120
tggtatcagc agaagcccgg taaagcccct aagctgctga tctactgggc ctctactaga    180
gaatcaggcg tgccctctag gtttagcggt agcggtagtg gcaccgactt caccttcact    240
atctctagcc tgcagcccga ggatatcgct acctactact gtcagaacga ctatagctac    300
ccctacacct tcggtcaagg cactaaggtc gagattaag                           339
```

<210> SEQ ID NO 98
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gagatcgtcc tgactcagtc acccgctacc ctgagcctga gccctggcga gcgggctaca     60
ctgagctgta aatctagtca gtcactgctg gatagcggta atcagaagaa cttcctgacc    120
tggtatcagc agaagcccgg taaagcccct aagctgctga tctactgggc ctctactaga    180
gaatcaggcg tgccctctag gtttagcggt agcggtagtg gcaccgactt caccttcact    240
atctctagcc tgcagcccga ggatatcgct acctactact gtcagaacga ctatagctac    300
ccctacacct tcggtcaagg cactaaggtc gagattaagc gtacggtggc cgctcccagc    360
gtgttcatct ccccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgaccct gagcaaggcc gactacgaga agcataaggt gtacgcctgc    600
gaggtgaccc accagggcct gtccagcccc gtgaccaaga gcttcaacag gggcgagtgc    660
```

<210> SEQ ID NO 99
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gagatcgtgc tgacccagtc ccccgacttc cagtccgtga cccccaaaga aaaagtgacc     60
atcacatgca gtcctcccca gtccctgctg gactccggca accagaagaa cttcctgacc    120
tggtatcagc agaagcccgg ccaggccccc agactgctga tctactgggc ctccacccgg    180
gaatctggcg tgccctctag attctccggc tccggctctg gcaccgactt taccttcacc    240
```

```
atctccagcc tggaagccga ggacgccgcc acctactact gccagaacga ctactcctac    300
ccctacacct tcggccaggg caccaaggtg gaaatcaag                            339
```

<210> SEQ ID NO 100
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gagatcgtgc tgacccagtc ccccgacttc cagtccgtga cccccaaaga aaaagtgacc     60
atcacatgca gtcctccca gtccctgctg gactccggca accagaagaa cttcctgacc    120
tggtatcagc agaagcccgg ccaggccccc agactgctga tctactgggc ctccacccgg    180
gaatctggcg tgccctctag attctccggc tccggctctg gcaccgactt taccttcacc    240
atctccagcc tggaagccga ggacgccgcc acctactact gccagaacga ctactcctac    300
ccctacacct tcggccaggg caccaaggtg gaaatcaagc gtacggtggc cgctcccagc    360
gtgttcatct cccccccaag cgacgagcag ctgaagagcg gcaccgccag cgtggtgtgt    420
ctgctgaaca acttctaccc cagggaggcc aaggtgcagt ggaaggtgga caacgccctg    480
cagagcggca cagccagga gagcgtcacc gagcaggaca gcaaggactc cacctacagc    540
ctgagcagca ccctgaccct gagcaaggcc gactacgaga agcacaaggt gtacgcctgt    600
gaggtgaccc accagggcct gtccagcccc gtgaccaaga gcttcaacag gggcgagtgc    660
```

<210> SEQ ID NO 101
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
gaagtgcagc tggtgcagtc tggcgccgaa gtgaagaagc ctggcgagtc cctgcggatc     60
tcctgcaagg gctctggcta caccttcacc acctactgga tgcactggat ccggcagtcc    120
ccctctaggg gcctggaatg gctgggcaac atctaccctg gcaccggcgg ctccaacttc    180
gacgagaagt tcaagaacag gttcaccatc tcccgggaca actccaagaa caccctgtac    240
ctgcagatga actccctgcg ggccgaggac accgccgtgt actactgtac cagatggacc    300
accggaaccg cgcgctattg gggccagggc acaacagtga ccgtgtcctc c             351
```

<210> SEQ ID NO 102
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
```

```
            35                  40                  45
Gly Asn Ile Tyr Pro Gly Thr Gly Ser Asn Phe Asp Glu Lys Phe
 50                  55                  60
Lys Asn Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Thr Arg Trp Thr Thr Gly Thr Gly Ala Tyr Trp Gly Gln Gly Thr Thr
            100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly
            435                 440

<210> SEQ ID NO 103
```

<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
gaagtgcagc tggtgcagtc tggcgccgaa gtgaagaagc tggcgagtc cctgcggatc       60
tcctgcaagg gctctggcta caccttcacc acctactgga tgcactggat ccggcagtcc      120
ccctctaggg gcctggaatg gctgggcaac atctaccctg caccggcgg ctccaacttc       180
gacgagaagt tcaagaacag gttcaccatc tcccgggaca actccaagaa caccctgtac      240
ctgcagatga actccctgcg ggccgaggac accgccgtgt actactgtac cagatggacc      300
accggaaccg cgcctattg gggccagggc acaacagtga ccgtgtcctc cgcttctacc       360
aaggggccca cgcgtgttcc cctggccccc tgctccagaa gcaccagcga gagcacagcc      420
gccctgggct gcctggtgaa ggactacttc cccgagcccg tgaccgtgtc ctggaacagc      480
ggagccctga ccagcggcgt gcacaccttc cccgccgtgc tgcagagcag cggcctgtac      540
agcctgagca gcgtggtgac cgtgccagc agcagcctgg gcaccaagac ctacacctgt       600
aacgtggacc acaagcccag caacaccaag gtggacaaga gggtggagag caagtacggc      660
ccaccctgcc cccctgccc agccccgag ttcctgggcg gacccagcgt gttcctgttc         720
cccccaagc caaggacac cctgatgatc agcagaaccc ccgaggtgac ctgtgtggtg         780
gtggacgtgt cccaggagga ccccgaggtc cagttcaact ggtacgtgga cggcgtggag      840
gtgcacaacg ccaagaccaa gcccagagag gagcagttta acagcaccta ccgggtggtg      900
tccgtgctga ccgtgctgca ccaggactgg ctgaacggca agagtacaa gtgtaaggtc       960
tccaacaagg gcctgccaag cagcatcgaa aagaccatca gcaaggccaa gggccagcct      1020
agagagccc aggtctacac cctgccaccc agccaagagg agatgaccaa gaaccaggtg      1080
tccctgacct gtctggtgaa gggcttctac ccaagcgaca tcgccgtgga gtgggagagc     1140
aacggccagc ccgagaacaa ctacaagacc acccccccag tgctggacag cgacggcagc     1200
ttcttcctgt acagcaggct gaccgtggac aagtccagat ggcaggaggg caacgtcttt     1260
agctgctccg tgatgcacga ggccctgcac aaccactaca cccagaagag cctgagcctg      1320
tccctgggc                                                              1329
```

<210> SEQ ID NO 104
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gagatcgtgc tgacccagtc ccctgccacc ctgtcactgt ctccaggcga gagagctacc       60
ctgtcctgca gtcctcccca gtccctgctg gactccggca accagaagaa cttcctgacc      120
tggtatcagc agaagcccgg ccaggccccc agactgctga tctactgggc ctccacccgg      180
gaatctggcg tgccctctag attctccggc tccggctctg gcaccgactt taccttcacc      240
atctccagcc tggaagccga ggacgccgcc acctactact gccagaacga ctactcctac      300
ccctacacct tcggccaggg caccaaggtg gaaatcaag                              339
```

<210> SEQ ID NO 105
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gagatcgtgc tgacccagtc ccctgccacc ctgtcactgt ctccaggcga gagagctacc    60
ctgtcctgca gtcctccca gtccctgctg gactccggca accagaagaa cttcctgacc   120
tggtatcagc agaagcccgg ccaggccccc agactgctga tctactgggc ctccacccgg   180
gaatctggcg tgccctctag attctccggc tccggctctg gcaccgactt taccttcacc   240
atctccagcc tggaagccga ggacgccgcc acctactact gccagaacga ctactcctac   300
ccctacacct tcggccaggg caccaaggtg gaaatcaagc gtacggtggc cgctcccagc   360
gtgttcatct ccccccaag cgacgagcag ctgaagagcg gcaccgccag cgtggtgtgt   420
ctgctgaaca acttctaccc cagggaggcc aaggtgcagt ggaaggtgga caacgccctg   480
cagagcggca acagccagga gagcgtcacc gagcaggaca gcaaggactc cacctacagc   540
ctgagcagca ccctgaccct gagcaaggcc gactacgaga agcacaaggt gtacgcctgt   600
gaggtgaccc accagggcct gtccagcccc gtgaccaaga gcttcaacag gggcgagtgc   660
```

<210> SEQ ID NO 106
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg tcaagcccct agactgctga tctactgggc ctctactaga   180
gaatcaggcg tgccctctag gtttagcggt agcggtagtg gcaccgactt caccttcact   240
atctctagcc tggaagccga ggacgccgct acctactact gtcagaacga ctatagctac   300
ccctacacct tcggtcaagg cactaaggtc gagattaag                          339
```

<210> SEQ ID NO 107
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg tcaagcccct agactgctga tctactgggc ctctactaga   180
gaatcaggcg tgccctctag gtttagcggt agcggtagtg gcaccgactt caccttcact   240
atctctagcc tggaagccga ggacgccgct acctactact gtcagaacga ctatagctac   300
ccctacacct tcggtcaagg cactaaggtc gagattaagc gtacggtggc cgctcccagc   360
gtgttcatct ccccccag cgacgagcag ctgaagagcg gcaccgccag cgtggtgtgc    420
```

```
ctgctgaaca acttctaccc ccgggaggcc aaggtgcagt ggaaggtgga caacgccctg      480
cagagcggca acagccagga gagcgtcacc gagcaggaca gcaaggactc cacctacagc      540
ctgagcagca ccctgaccct gagcaaggcc gactacgaga gcataaggt gtacgcctgc       600 gaggtgaccc caccagggcct gtccagcccc gtgaccaaga gcttcaacag gggcgagtgc    660
```

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
acttactgga tgcac                                                       15
```

<210> SEQ ID NO 109
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
aatatttatc ctggtactgg tggttctaac ttcgatgaga agttcaagaa c              51
```

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
tggactactg ggacgggagc ttat                                             24
```

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

```
ggctacacat tcaccactta c                                                21
```

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
tatcctggta ctggtggt                                                    18
```

<210> SEQ ID NO 113
<211> LENGTH: 51
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 113
aagtccagtc agagtctgtt agacagtgga aatcaaaaga acttcttgac c            51

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgggcatcca ctagggaatc t                                             21

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cagaatgatt atagttatcc gtgcacg                                       27

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
agtcagagtc tgttagacag tggaaatcaa aagaacttc                          39

<210> SEQ ID NO 117
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117 tgggcatcc                                                            9

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gattatagtt atccgtgc                                                 18

<210> SEQ ID NO 119
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 119
cagaatgatt atagttatcc gtacacg                                        27

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gattatagtt atccgtac                                                  18

<210> SEQ ID NO 121
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aagtccagtc agagtctgtt agacagtgga aatcaaaaga acttcttaac c             51

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acctactgga tgcac                                                     15

<210> SEQ ID NO 123
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aacatctatc ctggcaccgg cggctccaac ttcgacgaga agttcaagaa c             51

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tggacaaccg gcacaggcgc ttat                                           24

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 125
ggctacacct tcaccaccta c                                            21

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tatcctggca ccggcggc                                                18

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aagtcctccc agtccctgct ggactccggc aaccagaaga acttcctgac c            51

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgggcctcca cccgggaatc t                                            21

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cagaacgact actcctaccc ctacacc                                      27

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tcccagtccc tgctggactc cggcaaccag aagaacttc                         39

<210> SEQ ID NO 131
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 131 tgggcctcc                                                             9

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gactactcct acccctac                                                  18

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acctactgga tgcac                                                     15

<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aatatctacc ccggcaccgg cggctctaac ttcgacgaga agtttaagaa t             51

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tggactaccg gcacaggcgc ctac                                           24

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggctacacct tcactaccta c                                              21

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 137
taccccggca ccggcggc                                                 18

<210> SEQ ID NO 138
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
aaatctagtc agtcactgct ggatagcggt aatcagaaga acttcctgac c            51

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tgggcctcta ctagagaatc a                                             21

<210> SEQ ID NO 140
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cagaacgact atagctaccc ctacacc                                       27

<210> SEQ ID NO 141
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agtcagtcac tgctggatag cggtaatcag aagaacttc                          39

<210> SEQ ID NO 142
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142 tgggcctct                                                            9

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
```

```
gactatagct acccctac                                                    18

<210> SEQ ID NO 144
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aacatctacc ctggcaccgg cggctccaac ttcgacgaga agttcaagaa c               51

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tggaccaccg gaaccggcgc ctat                                             24

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
taccctggca ccggcggc                                                    18

<210> SEQ ID NO 147
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 148
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gaagtgcagc tggtgcagtc tggagcagag gtgaaaaagc ccggggagtc tctgaggatc      60
tcctgtaagg gttct                                                       75

<210> SEQ ID NO 149
<211> LENGTH: 75
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 149
gaagtgcagc tggtgcagtc tggcgccgaa gtgaagaagc ctggcgagtc cctgcggatc      60
tcctgcaagg gctct                                                       75

<210> SEQ ID NO 150
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gaggtgcagc tggtgcagtc aggcgccgaa gtgaagaagc ccggcgagtc actgagaatt      60
agctgtaaag gttca                                                       75

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 152
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
caggttcagc tggtgcagtc tggagctgag gtgaagaagc tgggggcctc agtgaaggtc      60
tcctgcaagg cttct                                                       75

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Trp Val Arg Gln Ala Thr Gly Gln Gly Leu Glu Trp Met Gly
1               5                   10

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
```

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tgggtgcgac aggccactgg acaagggctt gagtggatgg gt                              42

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tgggtgcgac aggctaccgg ccagggcctg gaatggatgg gc                              42

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tgggtccgcc aggctaccgg tcaaggcctc gagtggatgg gt                              42

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Trp Ile Arg Gln Ser Pro Ser Arg Gly Leu Glu Trp Leu Gly
1               5                   10

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tggatcaggc agtccccatc gagaggcctt gagtggctgg gt                              42

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tggatccggc agtcccctc tagggscctg gaatggctgg gc                               42

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Val Arg Gln Ala Pro Gly Gln Gly Leu Glu Trp Met Gly
1               5                   10

<210> SEQ ID NO 161
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgggtgcgac aggcccctgg acaagggctt gagtggatgg gt                            42

<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Arg Val Thr Ile Thr Ala Asp Lys Ser Thr Ser Thr Ala Tyr Met Glu
1               5                   10                  15
Leu Ser Ser Leu Arg Ser Glu Asp Thr Ala Val Tyr Tyr Cys Thr Arg
                20                  25                  30

<210> SEQ ID NO 163
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
agagtcacga ttaccgcgga caaatccacg agcacagcct acatggagct gagcagcctg        60
agatctgagg acacggccgt gtattactgt acaaga                                  96

<210> SEQ ID NO 164
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
agagtgacca tcaccgccga caagtccacc tccaccgcct acatggaact gtcctccctg        60
agatccgagg acaccgccgt gtactactgc acccgg                                  96

<210> SEQ ID NO 165
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
agagtgacta tcaccgccga taagtctact agcaccgcct atatggaact gtctagcctg        60
agatcagagg acaccgccgt ctactactgc actagg        96

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 167
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
agattcacca tctccagaga caattccaag aacacgctgt atcttcaaat gaacagcctg        60
agagccgagg acacggccgt gtattactgt acaaga        96

<210> SEQ ID NO 168
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aggttcacca tctcccggga caactccaag aacaccctgt acctgcagat gaactccctg        60
cgggccgagg acaccgccgt gtactactgt accaga        96

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Trp Gly Gln Gly Thr Thr Val Thr Val Ser Ser
1               5                   10

<210> SEQ ID NO 170
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tggggccagg gcaccaccgt gaccgtgtcc tcc        33

<210> SEQ ID NO 171
<211> LENGTH: 33

```
<210> SEQ ID NO 171
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tggggccagg gcaccacagt gaccgtgtcc tct                                  33

<210> SEQ ID NO 172
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tggggtcaag gcactaccgt gaccgtgtct agc                                  33

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tggggccagg gcacaacagt gaccgtgtcc tcc                                  33

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 175
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gaaattgtgc tgactcagtc tccagacttt cagtctgtga ctccaaagga gaaagtcacc    60
atcacctgc                                                            69

<210> SEQ ID NO 176
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
```

```
gagatcgtgc tgacccagtc ccccgacttc cagtccgtga cccccaaaga aaaagtgacc      60
atcacatgc                                                              69
```

<210> SEQ ID NO 177
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 178
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178

```
gaaattgtgt tgacacagtc tccagccacc ctgtctttgt ctccagggga agagccacc       60 ctctcctgc                                                              69
```

<210> SEQ ID NO 179
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
gagatcgtgc tgacccagtc ccctgccacc ctgtcactgt ctccaggcga gagagctacc      60
ctgtcctgc                                                              69
```

<210> SEQ ID NO 180
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180

```
gagatcgtcc tgactcagtc acccgctacc ctgagcctga gccctggcga gcgggctaca      60
ctgagctgt                                                              69
```

<210> SEQ ID NO 181
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Asp Ile Val Met Thr Gln Thr Pro Leu Ser Leu Pro Val Thr Pro Gly
1               5                   10                  15
```

Glu Pro Ala Ser Ile Ser Cys
         20

<210> SEQ ID NO 182
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gatattgtga tgacccagac tccactctcc ctgcccgtca cccctggaga gccggcctcc    60
atctcctgc                                                            69

<210> SEQ ID NO 183
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Val Val Met Thr Gln Ser Pro Leu Ser Leu Pro Val Thr Leu Gly
1               5                   10                  15

Gln Pro Ala Ser Ile Ser Cys
         20

<210> SEQ ID NO 184
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gatgttgtga tgactcagtc tccactctcc ctgcccgtca cccttggaca gccggcctcc    60
atctcctgc                                                            69

<210> SEQ ID NO 185
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys
         20

<210> SEQ ID NO 186
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186

```
gacatccaga tgacccagtc tccatcctcc ctgtctgcat ctgtaggaga cagagtcacc    60
atcacttgc                                                            69
```

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Trp Tyr Gln Gln Lys Pro Gly Gln Ala Pro Arg Leu Leu Ile Tyr
1               5                   10                  15

<210> SEQ ID NO 188
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188

```
tggtaccagc agaaacctgg ccaggctccc aggctcctca tctat                    45
```

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

```
tggtatcagc agaagcccgg ccaggccccc agactgctga tctac                    45
```

<210> SEQ ID NO 190
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

```
tggtatcagc agaagcccgg tcaagcccct agactgctga tctac                    45
```

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Tyr Gln Gln Lys Pro Gly Lys Ala Pro Lys Leu Leu Ile Tyr
1               5                   10                  15

<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tggtatcagc agaaaccagg gaaagctcct aagctcctga tctat        45

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tggtatcagc agaagcccgg taaagcccct aagctgctga tctac        45

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Tyr Leu Gln Lys Pro Gly Gln Ser Pro Gln Leu Leu Ile Tyr
1               5                   10                  15

<210> SEQ ID NO 195
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tggtacctgc agaagccagg gcagtctcca cagctcctga tctat        45

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
                20                  25                  30

<210> SEQ ID NO 197
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggggtcccct cgaggttcag tggcagtgga tctgggacag atttcacctt taccatcagt    60
agcctggaag ctgaagatgc tgcaacatat tactgt                              96

<210> SEQ ID NO 198

-continued

<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggcgtgccct ctagattctc cggctccggc tctggcaccg actttacctt caccatctcc    60
agcctggaag ccgaggacgc cgccacctac tactgc                              96

<210> SEQ ID NO 199
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggcgtgccct ctaggtttag cggtagcggt agtggcaccg acttcacctt cactatctct    60
agcctggaag ccgaggacgc cgctacctac tactgt                              96

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 201
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gggatcccac ctcgattcag tggcagcggg tatggaacag attttaccct cacaattaat    60
aacatagaat ctgaggatgc tgcatattac ttctgt                              96

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 203

```
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggggtcccat caaggttcag cggcagtgga tctgggacag aattcactct caccatcagc    60
agcctgcagc ctgatgattt tgcaacttat tactgt                              96

<210> SEQ ID NO 204
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggcgtgccct ctagattctc cggctccggc tctggcaccg agtttaccct gaccatctcc    60
agcctgcagc ccgacgactt cgccacctac tactgc                              96

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 206
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ggggtcccat caaggttcag tggaagtgga tctgggacag attttacttt caccatcagc    60
agcctgcagc ctgaagatat tgcaacatat tactgt                              96

<210> SEQ ID NO 207
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ggcgtgccct ctaggtttag cggtagcggt agtggcaccg acttcacctt cactatctct    60
agcctgcagc ccgaggatat cgctacctac tactgt                              96

<210> SEQ ID NO 208
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 208

Phe Gly Gln Gly Thr Lys Val Glu Ile Lys
1               5                   10

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttcggccaag ggaccaaggt ggaaatcaaa                                      30

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ttcggccagg gcaccaaggt ggaaatcaag                                      30

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ttcggtcaag gcactaaggt cgagattaag                                      30

<210> SEQ ID NO 212
<211> LENGTH: 327
<212> TYPE: PRT
<213> ORGANISM: Homo sapiens

<400> SEQUENCE: 212

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
```

```
                115                 120                 125
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 213
<211> LENGTH: 107
<212> TYPE: PRT
<213> ORGANISM: Homo sapiens

<400> SEQUENCE: 213

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 214
<211> LENGTH: 326
<212> TYPE: PRT
<213> ORGANISM: Homo sapiens

<400> SEQUENCE: 214

Ala Ser Thr Lys Gly Pro Ser Val Phe Pro Leu Ala Pro Cys Ser Arg
```

```
            1               5                  10                 15
Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Gln Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 215
<211> LENGTH: 330
<212> TYPE: PRT
<213> ORGANISM: Homo sapiens

<400> SEQUENCE: 215

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45
```

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 216
<211> LENGTH: 330
<212> TYPE: PRT
<213> ORGANISM: Homo sapiens

<400> SEQUENCE: 216

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 217
<211> LENGTH: 330
<212> TYPE: PRT
<213> ORGANISM: Homo sapiens

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
                130                 135                 140
Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Ala Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 218
<211> LENGTH: 330
<212> TYPE: PRT
<213> ORGANISM: Homo sapiens

<400> SEQUENCE: 218

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tggactactg ggacgggagc ttac                                            24

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 224

Gly Tyr Thr Phe Thr Thr Tyr Trp Met His
1               5                   10

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Tyr Trp Met Tyr
1               5

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ile Asp Pro Asn Ser Gly Ser Thr Lys Tyr Asn Glu Lys Phe Lys
1               5                   10                  15

Asn

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Tyr Arg Lys Gly Leu Tyr Ala Met Asp Tyr
1               5                   10

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Tyr Thr Phe Thr Ser Tyr
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asp Pro Asn Ser Gly Ser
1               5
```

```
<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Lys Ala Ser Gln Asp Val Gly Thr Ala Val Ala
1               5                   10

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Trp Ala Ser Thr Arg His Thr
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Gln Tyr Asn Ser Tyr Pro Leu Thr
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Gln Asp Val Gly Thr Ala
1               5

<210> SEQ ID NO 234
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Trp Ala Ser
1

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235
```

```
<210> SEQ ID NO 236
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 237
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
gaggtccagc tggtacagtc tggggctgag gtgaagaagc ctggggctac agtgaaaatc     60
tcctgcaagg tttctggcta caccttcacc agttactgga tgtactgggt gcgacaggct    120
cgtggacaac gccttgagtg gataggtagg attgatccta atagtgggag tactaagtac    180
aatgagaagt tcaagaacag attcaccatc tccagagaca attccaagaa cacgctgtat    240
cttcaaatga acagcctgag agccgaggac acggccgtgt attactgtgc aagggactat    300
agaaaggggc tctatgctat ggactactgg ggccagggca ccaccgtgac cgtgtcctcc    360

<210> SEQ ID NO 238
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
gaggtccagc tggtacagtc tggggctgag gtgaagaagc ctggggctac agtgaaaatc     60
tcctgcaagg tttctggcta caccttcacc agttactgga tgtactgggt gcgacaggct    120
cgtggacaac gccttgagtg gataggtagg attgatccta atagtgggag tactaagtac    180
```

Tyr Asn Ser Tyr Pro Leu
1               5

```
aatgagaagt tcaagaacag attcaccatc tccagagaca attccaagaa cacgctgtat    240
cttcaaatga acagcctgag agccgaggac acggccgtgt attactgtgc aagggactat    300 agaaagggc tctatgctat ggactactgg ggccagggca ccaccgtgac cgtgtcctcc    360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accgtgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtgt ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca gagcaggtg gcaggagggg   1260 aatgtcttct catgctccgt gatgcatgag gctctgcaca accactacac acagaagagc   1320
ctctccctgt ctctgggtaa a                                            1341
```

<210> SEQ ID NO 239
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Leu Gln Lys Pro Gly Gln Ser Pro Gln Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 240
<211> LENGTH: 321
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 240

```
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa a                                                321
```

<210> SEQ ID NO 241
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 242
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 242

```
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagctcgc ccgtcacaaa gagcttcaac aggggagagt gt                        642
```

<210> SEQ ID NO 243
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Tyr Thr Phe Thr Ser Tyr Trp Met Tyr
1               5                   10

<210> SEQ ID NO 245
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80
```

```
Met Asn Ser Leu Arg Ala Glu Asp Thr Ala Val Tyr Tyr Cys Ala Arg
            85                  90                  95

Ile Lys Leu Gly Thr Val Thr Val Asp Tyr Trp Gly Gln Gly Thr
            100                 105                 110

Leu Val Thr Val Ser Ser
        115

<210> SEQ ID NO 246
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Ser Ala Leu Thr Gln Pro Ala Ser Val Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 247
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140
```

```
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 248
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 249
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
```

```
            195                 200                 205
Pro Ser Asn Thr Lys Val Asp Lys Arg Val Glu Ser Lys Tyr Gly Pro
    210                 215                 220

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 250
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110
```

-continued

```
Thr Val Ala Ala Pro Ser Val Phe Ile Phe Pro Pro Ser Asp Glu Gln
        115                 120             125

Leu Lys Ser Gly Thr Ala Ser Val Val Cys Leu Leu Asn Asn Phe Tyr
        130                 135             140

Pro Arg Glu Ala Lys Val Gln Trp Lys Val Asp Asn Ala Leu Gln Ser
145             150                 155                     160

Gly Asn Ser Gln Glu Ser Val Thr Glu Gln Asp Ser Lys Asp Ser Thr
                165                 170             175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

5-BROMO-2,6-DI-(1H-PYRAZOL-1-YL)PYRIMIDIN-4-AMINE FOR USE IN THE TREATMENT OF CANCER

This application is a U.S. national Phase filing of International Serial No. PCT/IB2016/054834 filed Aug. 10, 2016, and claims priority to U.S. application Ser. No. 62/335,984 filed May 13, 2016 and EP application No. 15382425.5 filed Aug. 11, 2015, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 5, 2016, is named PAT057215-US-PSP_SL.txt and is 207,763 bytes in size.

FIELD OF THE INVENTION

The present invention relates to 5-bromo-2,6-di-(1H-pyrazol-1-yl)pyrimidin-4-amine, its pharmaceutically acceptable salts and co-crystals thereof and to pharmaceutical compositions comprising said compounds for use in the treatment of cancer, particularly carcinomas, specifically for use in the treatment of lung cancer, and more specifically for use in the treatment of non-small cell lung cancer.

Other objectives of the present invention is to provide methods for the treatment of cancer, particularly carcinomas, specifically lung cancer, and more specifically of non-small cell lung cancer by administration of compound of formula (I), or by administration of a pharmaceutical composition or a combination product comprising compound of formula (I).

BACKGROUND OF THE INVENTION

Cancer is a major public health problem in worldwide. It is currently the second leading cause of death in the United States and in several developed countries, and is expected to surpass heart diseases as the leading cause of death in the next few years. (Siegel R L, et al, Cancer Statistics, 2015, CA Cancer J Clin 2015; 65:5-29. VC 2015 American Cancer Society and references therein).

Cancer is considers a complex disease that is dictated by both cancer cell-intrinsic and cell-extrinsic processes. Several studies conducted in various in vitro and animal models including, for example, lung metastasis, human lung adenocarcinoma cells, murine melanoma cells, murine ovarian cancer cells, murine breast cancer cells, have confirmed that targeting the adenosinergic system has tremendous potential to develop different treatments. A number of lines of evidence highlight the importance of adenosine as a critical regulatory autocrine and paracrine factor that accumulates in the neoplastic microenvironment. Extracellular adenosine, which is usually present at high concentrations in cancer tissues, is a crucial mediator in the alteration of immune cell functions in cancer. This is possibly because the tightly regulated adenosine receptor pathways of immune cells undergo substantial alterations in tumours, thereby switching the functions of these cells from immune surveillance and host defense to the promotion of cancer cell transformation and growth. (Antonioli L et al, *Immunity, inflammation and cancer: a leading role for adenosine*, Nature, 842, December 2013, Volume 13, and references therein).

As it is known tumors use numerous immunosuppressive mechanisms to facilitate tumor growth (Koebel C M. et al, *Adaptive immunity maintains occult cancer in an equilibrium state*, Nature. 2007, 450, 7171:903-907 and Schreiber R D. et al, *Cancer immunoediting: Integrating immunity's roles in cancer suppression and promotion*, Science. 2011, 331, 6024:1565-1570). There are studies establishing that one such mechanism was mediated by the catabolism of extracellular AMP into immunosuppressive adenosine (Ohta A. et al, *A2A adenosine receptor protects tumors from antitumor T cells*. Proc Natl Acad Sci USA. 2006; 103: 13132-13137 and Ohta A. et al, *A2A adenosine receptor may allow expansion of T cells lacking effector functions in extracellular adenosine-rich microenvironments*. J Immunol. 2009, 183, 9:5487-5493). Firstly, extracellular ATP will be converted to AMP by the ectoenzyme CD39. Further dephosphorylation of the AMP through the CD73 ectoenzyme will result in extracellular adenosine production.

During this process, activity of adenosine kinase is also suppressed causing the inhibition of salvage activity of this enzyme and an increase in adenosine levels. For example, under hypoxic conditions during inflammation or within tumor microenvironment, inhibition of adenosine kinase causes 15-20-fold increase in both extracellular as well as intracellular levels of adenosine (Decking U K. Et al, *Hypoxia-induced inhibition of adenosine kinase potentiates cardiac adenosine release*. Circ. Res. 1997; 81(2):154-164. doi: 10.1161/01.RES.81.2.154). The generated extracellular adenosine binds to four known cell surface receptors (A1, A2A, A2B, and A3) that are expressed on multiple immune subsets including T cells, natural killer (NK) cells, natural killer T cells, macrophages, dendritic cells, and myeloid-derived suppressor cells (MDSCs). The A2A and A2B receptor subtypes are essentially responsible for the immunosuppressive effects of adenosine. They share a common signalling pathway, both resulting in the activation of adenylate cyclase and the accumulation of intracellular cAMP. Several evidences have been further provided demonstrating that the intracellular cAMP is the signalling molecule that inhibits T-cell receptor signalling at early and late stages of T-cell receptor-triggered T-cell activating pathway. (Ohta A, Sitkovsky M, *Role of G-protein-coupled adenosine receptors in downregulation of inflammation and protection from tissue damage*, Nature, 2001, 414: 916-920).

It has been suggested that the elimination of $A_2a$ receptor genetically or the inhibition of $A_2a$ receptor signalling using $A_2a$ receptor antagonists prevents inhibition of anti-tumour T cells and improves tumour rejection (Ohta A. et al, *$A_2a$ adenosine receptor protects tumors from antitumor T cells*. Proc Natl Acad Sci USA. 2006; 103: 13132-13137).

$A_2a$ receptor functions as a non-redundant negative regulator of activated T cells to protect normal tissues from excessive collateral inflammatory damage. It has been proposed that $A_2a$ receptor may also 'misguidedly' protect cancerous tissues. It was reasoned that if this were indeed the case, then the genetic inactivation or pharmacological antagonism of $A_2a$ receptor would prevent the inhibition of anti-tumour T cells and thereby improve tumour rejection by these de-inhibited T cells (Sitkovsky M. et al, *Adenosine $A_2a$ receptor antagonists: blockade of adenosinergic effects and T regulatory cells*, British Journal of Pharmacology, 2008, 153, S457-S464).

Lung cancer is the leading cause of cancer death around the world and it has been the most common cancer worldwide since 1985, both in terms of incidence and mortality. Globally, lung cancer is the largest contributor to new cancer diagnoses (12.4% of total new cancer cases) and to death from cancer (17.6% of total cancer deaths).

Lung cancer arises from the cells of the respiratory epithelium and can be divided into two broad categories. Small cell lung cancer (SCLC) is a highly malignant tumor derived from cells exhibiting neuroendocrine characteristics and accounts for 15% of lung cancer cases. Non-small cell lung cancer (NSCLC), which accounts for the remaining 85% of cases, is further divided into 3 major pathologic subtypes: adenocarcinoma, squamous cell carcinoma, and large cell carcinoma. Adenocarcinoma by itself accounts for 38.5% of all lung cancer cases, with squamous cell carcinoma accounting for 20% and large cell carcinoma accounting for 2.9%. In the past several decades, the incidence of adenocarcinoma has increased greatly, and adenocarcinoma has replaced squamous cell carcinoma as the most prevalent type of NSCLC. (De la Cruz, C et al, *Lung Cancer: Epidemiology, Etiology, and Prevention*, Clin Chest Med. 2011 December; 32(4)).

Particularly, in the case of NSCLC, disease stage determines the treatment, which includes surgery, radiation, platinum-based doublet chemotherapy and recently targeted therapies by interrupting signaling pathways responsible for cell proliferation and survival. Earlier stages of the disease benefit from systemic chemotherapy (platinum-doublet, taxanes, gemcitabine, pemetrexed) (Azzoli C G. et al, 2011 *Focused Update of* 2009 *American Society of Clinical Oncology Clinical Practice Guideline Update on Chemotherapy for Stage IV Non-Small-Cell Lung Cancer*, J Oncol Pract. 2012; 8:63-6 doi:10.1200/JOP.2011.000374), that results in modest efficacy, thus, multimodal therapeutic strategy has become an important treating option for NSCLC patients. In several studies, two or more drug combinations were proven to have superior efficacy but at the expense of added toxicity (Yoshida T. et al, *Comparison of adverse events and efficacy between gefitinib and erlotinib in patients with non-small-cell lung cancer: a retrospective analysis*, Med Oncol. 2013; 30:349).

Recently, several approaches are being developed to boost anticancer responses of T-cells and restore their ability to detect and attack cancer cells among them mAbs blocking the cytotoxic lymphocyte-associated antigen 4 (CTLA4) and the programmed cell death protein 1 (PD-1)-mediated T-cell events have been developed.

Ipilimumab, a fully human mAb against CTLA4, has shown a trend toward greater clinical benefit among patients with SQCLC (Lynch T J. et al, *Ipilimumab in combination with paclitaxel and carboplatin as first-line treatment in stage IIIB/IV non-small-cell lung cancer: Results from a randomized, double-blind, multicenter phase II study*, J Clin Oncol. 2012; 30: 2046-54). The PD-1 mAbs (MED14735, BMS-936558, BMS-936559) have demonstrated remarkable sustained tumour regressions in the heavily pre-treated advanced NSCLC patients (Brahmer J R. et al, *Safety and activity of anti-PD-L1 antibody in patients with advanced cancer*, N Engl J Med. 2012; 366: 2455-65).

There are studies showing the alterations provoking changes in the extracellular tumor microenvironment. One of such extracellular alterations is the increased adenosine concentrations, which impair T cell mediated rejection and support angiogenesis. The study showed a significant number of lung adenocarcinomas expressing adenosine $A_2a$ receptor, supporting tests of adenosine $A_2a$ receptor antagonists as anticancer therapies. (Mediavilla-Varela, M et al, *Antagonism of adenosine $A_2a$ receptor expressed by lung adenocarcinoma tumor cells and cancer associated fibroblasts inhibits their growth*, Cancer Biology & Therapy, September 2013, 14:9, 860-868).

Despite the development of new therapeutics, NSCLC still has a 5-year survival rate in only 14% implying the need for the continuing research for novel treatments (Spira A. et al, *Multidisciplinary management of lung cancer*, N Engl J Med. 2004; 350:379-92 doi: 10.1056/NEJMra035536).

SUMMARY OF THE INVENTION

There remains a need for new treatments and therapies for the treatment of cancer. International patent application WO 2011/121418 A1 discloses a group of 4-aminopyrimidine derivatives as antagonists of the $A_2a$ receptors and their use in the treatment of conditions or diseases susceptible of amelioration by antagonism of said adenosine receptors. Although treatment of cancer is not specifically recited in WO 2011/121418 A1, the inventors have investigated the effectiveness of the compounds described in WO 2011/121418 A1 in the treatment of cancer and have unexpectedly found that not all the A2A antagonists covered by the claims of WO 2011/121418 A1 are effective in the treatment of cancer, particularly carcinomas, in particular lung cancer.

The inventors of the current invention have now surprisingly found that 5-bromo-2,6-di-(1H-pyrazol-1-yl)pyrimidin-4-amine of formula (I)

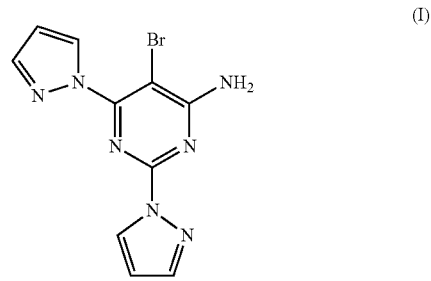 [SMILES: Nc1nc(-n2cccn2)nc(-n2cccn2)c1Br]

is significantly more efficacious for the treatment of cancer, particularly carcinomas, more specifically lung cancer, and more specifically non-small cell lung cancer, in comparison with other adenosine $A_2a$ receptor antagonists disclosed in said patent application WO 2011/121418 A1. Additionally, the compound of formula (I) has demonstrated a synergistic effect with other immunotherapeutic agents to stimulate the immune system for the treatment of cancer.

In one aspect the present invention provides 5-bromo-2,6-di-(1H-pyrazol-1-yl)pyrimidin-4-amine of formula (I), its pharmaceutically acceptable salts and co-crystals thereof for use in the treatment of cancer, particularly carcinomas, more specifically lung cancer, and more specifically non-small cell lung cancer. 5-bromo-2,6-di-(1H-pyrazol-1-yl)pyrimidin-4-amine has the ability to boost the immune system and to block one of the evasion mechanism used by the tumors. Another advantage is given by the low toxicity profile of said compound, already tested in different animal models in comparison with classical chemotherapy and with other adenosine receptor antagonists known in the state of the art. Another differential point is the possibility to be administered orally.

The present invention relates to 5-bromo-2,6-di-(1H-pyrazol-1-yl)pyrimidin-4-amine, its pharmaceutically acceptable salts and co-crystals thereof, to pharmaceutical compositions comprising said compounds and to combinations of said compound with one or more immunotherapeutic agents useful in the treatment of cancer, for use in the treatment of cancer, particularly for use in the treatment of carcinomas, specifically for use in the treatment of lung cancer, and more specifically for use in the treatment of non-small cell lung cancer.

The invention further provides methods of treating, preventing, or ameliorating cancer, comprising administering to a subject in need thereof an effective amount of a compound of Formula I; or a pharmaceutically acceptable salt thereof. Furthermore, the invention provides methods of treating, preventing, or ameliorating cancer, comprising administering to a subject in need thereof an effective amount of a compound of Formula I; or a pharmaceutically acceptable salt thereof, with one or more immunotherapeutic agents as described herein.

In another embodiment, the invention provides a combination, in particular a pharmaceutical combination, comprising a therapeutically effective amount of the compound according to the definition of formula (I), or a pharmaceutically acceptable salt thereof or co-crystals thereof, and one or more immunotherapeutically active agent as described herein.

In another embodiment, the invention pertains to the use of a pharmaceutical combination, comprising a therapeutically acceptable amount of a compound of Formula (I), or a pharmaceutically acceptable salt thereof or co-crystals thereof, and one or more immunotherapeutically active agent, for the manufacture of a medicament for treating cancer.

Kits, e.g. therapeutic kits, that include the immunotherapeutic agent and the compound of Formula (I), and instruction for use, are also disclosed.

In one embodiment, a combination described herein includes as immunotherapeutic agent, a PD-1 inhibitor. In some embodiments, the combination is used to treat a cancer, e.g., a cancer described herein, e.g., a solid tumor or a hematologic malignancy.

In one aspect of the embodiment, the PD-1 inhibitor is an anti-PD-1 antibody molecule which is selected from Nivolumab, Pembrolizumab and Pidilizumab.

In another aspect of above embodiment, the PD-1 inhibitor is anti-PD-1 antibody molecule which is disclosed in US 2015/0210769, published on Jul. 30, 2015, entitled "Antibody Molecules to PD-1 and Uses Thereof," incorporated by reference in its entirety.

In yet another embodiment, a combination described herein includes as immunotherapeutic agent, a PD-L1 inhibitor. In some embodiments, the combination is used to treat a cancer, e.g., a cancer described herein, e.g., a solid tumor or a hematologic malignancy.

In one aspect of the above embodiment, the PD-L1 inhibitor is an anti-PD-L1 antibody selected from YW243.55.S70, MPDL3280A, MEDI-4736, MSB-0010718C, and MDX-1105.

In another aspect of the above embodiment, the PD-L1 inhibitor is an anti-PD-L1 antibody molecule disclosed in US 2016/0108123, filed Oct. 13, 2015, entitled "Antibody Molecules to PD-L1 and Uses Thereof," incorporated by reference in its entirety.

DESCRIPTION OF THE FIGURES

FIG. 9 depicts the structural analysis of the humanized BAP049 clones (a, b, c, d and e represent various types of framework region sequences). The concentratiosn of the mAbs in the samples are also shown FIG. 10 depicts the ranking of humanized BAP049 clones based on FACS data, competition binding and structural analysis. The concentrations of the mAbs in the samples are also shown.

Figure 1A:
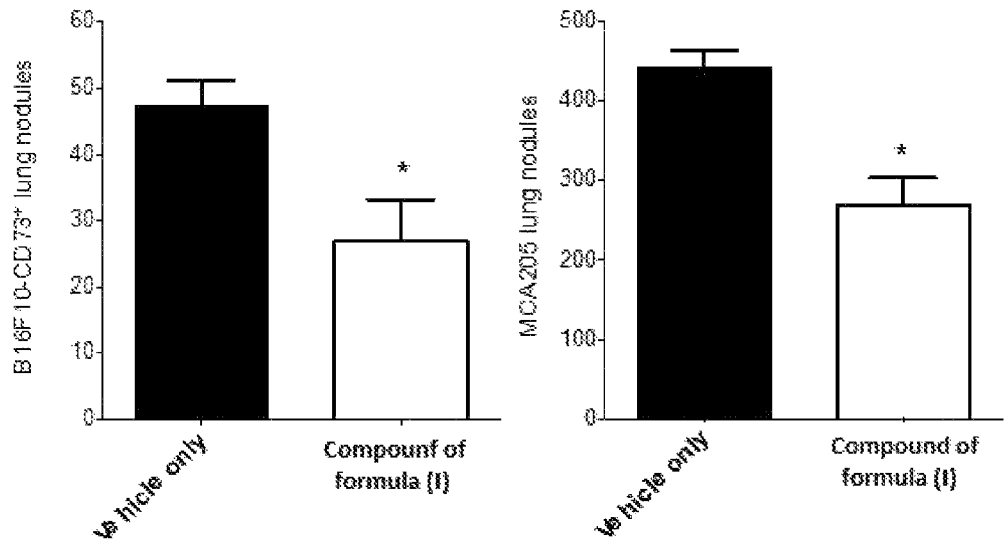
FIG. 1a shows the anti-tumoral activity of orally administered Compound of formula (I) in two syngeneic mouse models of cancer. (mean lung nodules of 9-10 mice/group±standard errors are shown; *: P<0.05 by Student T test).

The following abbreviations are used in the legends of FIGS. 2-8:
Tu=Lung tumor cells (without treatment); IFNg=Interferon gamma; IL1b=Interleukin-1b; IL13=Interleukin-13; IL10=Interleukin-10; IL5=Interleukin-5; IL17=Interleukin-17; TNFa=Tumor Necrosis Factor alfa; MIP1b=Macrophage Inflammatory Protein 1beta.
Anti-PD-L1=human monoclonal antibody against the PD-L1 receptor Functional Grade Purified 100 μg purchased from eBioscience, #16-5983-82.
Anti-PD-1=human monoclonal antibody against the PD-1 receptor Functional Grade Purified 100 μg purchased from eBioscience, #16-9989-82.

DETAILED DESCRIPTION OF THE INVENTION

In one aspect the present invention relates to 5-bromo-2,6-di-(1H-pyrazol-1-yl)pyrimidin-4-amine of formula (I)

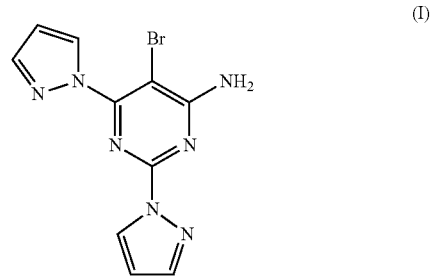 [SMILES: Nc1nc(-n2cccn2)nc(-n2cccn2)c1Br]

its pharmaceutically acceptable salts or co-crystals thereof for use in the treatment of cancer, particularly carcinomas specifically lung cancer, and more specifically non-small cell lung cancer.

In another aspect the present invention relates to the use of 5-bromo-2,6-di-(1H-pyrazol-1-yl)pyrimidin-4-amine of formula (I), its pharmaceutically acceptable salts or co-crystals thereof for the manufacture of a medicament for the treatment of cancer, particularly carcinomas, more specifically lung cancer, and more specifically non-small cell lung cancer.

In yet another aspect the present invention relates to the use of a pharmaceutical composition comprising 5-bromo-2,6-di-(1H-pyrazol-1-yl)pyrimidin-4-amine of formula (I), its pharmaceutically acceptable salt or co-crystals thereof for use in the treatment of cancer, particularly carcinomas, specifically lung cancer, and more specifically non-small cell lung cancer.

In yet another aspect the present invention relates to the use of a pharmaceutical composition comprising 5-bromo-2,6-di-(1H-pyrazol-1-yl)pyrimidin-4-amine of formula (I), its pharmaceutically acceptable salt or co-crystals thereof for the manufacture of a medicament for treating cancer, particularly carcinomas, specifically lung cancer, and more specifically non-small cell lung cancer.

In still another aspect the present invention relates to a pharmaceutical combination comprising 5-bromo-2,6-di-(1H-pyrazol-1-yl)pyrimidin-4-amine of formula (I), its pharmaceutically acceptable salts or co-crystals thereof and one or more immunotherapeutic agent useful in the treatment of cancer In yet another aspect the present invention relates to a combination as described herein for use in the treatment of cancer, particularly carcinomas, specifically lung cancer, and more specifically non-small cell lung cancer.

In still another aspect the present invention relates to the use of a pharmaceutical combination comprising 5-bromo-2,6-di-(1H-pyrazol-1-yl)pyrimidin-4-amine of formula (I), its pharmaceutically acceptable salts or co-crystals thereof and one or more immunotherapeutic agent useful in the treatment of cancer, for the manufacture of a medicament for treating cancer.

In yet another aspect of the present invention refers to methods for the treatment of cancer, particularly carcinomas, specifically lung cancer, and more specifically non-small cell lung cancer, by administration of:
  A compound of formula (I) or a pharmaceutically acceptable salts or co-crystals thereof, or
  A pharmaceutical composition comprising compound of formula (I) or a pharmaceutically acceptable salts or co-crystals thereof, or
  A combination product comprising compound of formula (I) or a pharmaceutically acceptable salt or co-crystals thereof.

In a preferred embodiment 5-bromo-2,6-di-(1H-pyrazol-1-yl)pyrimidin-4-amine of formula (I), its pharmaceutically acceptable salt or co-crystals thereof, the combinations comprising said compounds and one or more immunotherapeutic agents useful in the treatment of cancer and the pharmaceutical compositions comprising said compounds are used in the treatment of lung cancer, more preferably non-small cell lung cancer.

In a preferred embodiment of the present invention, the combination product comprising compound of formula (I) or a pharmaceutically acceptable salt or co-crystal thereof is for use in the treatment of lung cancer, specifically non-small cell lung cancer. In a more preferred embodiment of the present invention, the combination product comprising compound of formula (I) or a pharmaceutically acceptable salt or co-crystal thereof and an anti-PD-L1 antibody, such as MPDL3280A, MED14736, MDX-1105 or an anti-PD-L1 antibody described in US 2016/0108123-A1, is for use in the treatment of lung cancer, specifically non-small cell lung cancer.

According to another embodiment of the present invention, the combination product comprising compound of formula (I) or a pharmaceutically acceptable salt or co-crystal thereof and an anti-PD-1 antibody, such as MDX-1106, MK3475, CT-011, AMP-224 or an anti-PD-1 antibody molecule as described in WO2015/112900, is for use in the treatment of lung cancer, specifically non-small cell lung cancer.

The present invention may be employed in respect of human or animal subject, more preferably a mammal, more preferably a human subject.

Definitions

As used in the present document the term cancer is used to designate a group of diseases involving abnormal cell growth with the potential to invade or spread to other parts of the body. Cancers are classified by the type of cell that the tumor cells resemble and is therefore presumed to be the origin of the tumor. These types include carcinoma, sarcoma, lymphoma and leukemia, germ cell tumor and blastoma.

As used in the present document the term carcinoma is used to designate cancers derived from epithelial cells. This group includes many of the most common cancers, particularly in the aged, and include nearly all those developing in the breast, prostate, lung, pancreas, and colon.

For example the term "cancer" includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, B-cell lymphoma, a non-Hogdkin lymphoma, or a leukemia (e.g., a myeloid leukemia or a lymphoid leukemia).

In another embodiment, the cancer can be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer (e.g., differentiated or undifferentiated metastatic or locally recurrent nasopharyngeal carcinoma), or breast cancer.

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer or small cell lung cancer.

As used in the present document the term lung cancer (also known as carcinoma of the lung or pulmonary carcinoma) is used to designate malignant lung tumors characterized by uncontrolled cell growth in tissues of the lung.

As used in the present document the term non-small-cell lung carcinoma (NSCLC) is used to designate any type of lung cancer other than small cell lung carcinoma (SCLC).

As used in the present document the term immunotherapeutic treatment refers to a broad class of therapies designated to elicit immune-mediated destruction of tumor cells. In said therapies are used immunotherapeutic agents.

As used in the present document the term immunotherapeutic agents refer to compounds useful to carrying out immunotherapeutic treatment of cancer, such as agent selected from the group consisting of anti-CTLA4 antibodies, such as Ipilimumab and Tremelimumab, anti-PD-1 antibodies such as MDX-1106, MK3475, CT-011, AMP-224 or an anti-PD-1 antibody molecule as described in WO2015/112900; and anti-PD-L1 antibodies such as MED14736, MDX-1105 or an anti-PD-L1 antibody described in US 2016/0108123.

As used herein, the term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

As used herein, the term "Programmed Death Ligand 1" or "PD-L1" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

As used herein, the term co-crystals is used to designate crystalline materials composed of two or more molecules in the same crystal lattice, more particularly co-crystals formed by a molecule of 5-bromo-2,6-di-(1H-pyrazol-1-yl)pyrimidin-4-amine of formula (I), its pharmaceutically acceptable salt and a pharmaceutically acceptable mono- di- or tri-carboxylic acid such as mandelic, benzoic, acetic, 1-hydroxy-2-naphthoic, pyroglutamic, benzoic, formic, hippuric, lactic, propionic, glucuronic, pyruvic, sorbic, butyric, valeric, caproic, caprylic, glycolic, salicylic, fumaric, maleic, malic, oxalic, succinic, tartaric, malonic, gluconic, glutaric, adipic, pimelic, glutamic, mesaconic, citraconic, itaconic, mucic, phthalic, oxalacetic, aspartic, glutamic, acetoacetic, levulinic, citric, isocitric, aconitic, propane-1,2,3-tricarboxylic, more preferably a pharmaceutically acceptable dicarboxylic acid such as fumaric, maleic, malic, oxalic, succinic, tartaric, malonic, gluconic, glutaric, adipic, pimelic, glutamic, mesaconic, citraconic, itaconic, mucic, phthalic, oxalacetic, aspartic, glutamic, acetoacetic and levulinic, and more specifically with succinic, fumaric and phthalic acids.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Examples of inorganic acid include hydrochloric, sulphuric, phosphoric, diphosphoric, hydrobromic, hydroiodic and nitric acid and examples of organic acids include citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion (X–) is associated with the positive charge of the N atom. X– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and ptoluenesulphonate. X– is preferably an anion selected from chloride, bromide, iodide, sulphate, nitrate, acetate, maleate, oxalate, succinate or trifluoroacetate. More preferably, X– is chloride, bromide, trifluoroacetate or methanesulphonate.

As used herein the term "combination" refers to either a fixed combination in one dosage unit form, or a combined administration where a compound of Formula I and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that the compound of Formula I and a combination partner (i.e. immunotherapeutic agent), are both administered to a patient simultaneously in the form of a single entity or dosage. The term "non-fixed combination" means that the compound of Formula I and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat a cancer as described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

As used herein, the term "pharmaceutically acceptable carrier" or "pharmaceutically acceptable vehicle" are used interchangeably and includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention (compound of Formula I) refers to an amount of the compound of Formula I that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of Formula I that, when administered to a subject, is effective to (1) at least partially alleviate, inhibit, prevent and/or ameliorate a condition, or a disorder or a disease (i) mediated by $A_2a$ receptor or (ii) associated with $A_2a$ receptor activity, or (iii) characterized by activity (normal or abnormal) of $A_2a$ receptor; or (2) reduce or inhibit the activity of $A_2a$ receptor. In another non-limiting embodiment, the term "a therapeutically effective amount" refers to the amount of the compound of Formula I that, when administered to a cell, or a tissue, or a non-cellular biological material, or a medium, is effective to at least partially reducing or inhibiting the activity of $A_2a$ receptor; or at least partially reducing or inhibiting the expression of $A_2a$ receptor.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

Combination Therapy

In one embodiment, a pharmaceutical combination (or combination product) comprises a compound of formula (I) or a pharmaceutically acceptable salt or co-crystal thereof, and one or more immunotherapeutic agents selected from the group consisting of anti-CTLA4 antibodies, such as Ipilimumab and Tremelimumab, anti-PD-1 antibodies such as MDX-1106 (nivolumab), MK3475 (pembrolizumab), CT-011 (pidilizumab), AMP-224 or an anti-PD-1 antibody molecule as described in WO2015/112900 (US2015/0210769); and anti-PD-L1 antibodies such as MPDL3280A, MED14736 and MDX-1105 or an anti-PD-L1 antibody molecules are disclosed in US 2016/0108123, filed Oct. 13, 2015, entitled "Antibody Molecules to PD-L1 and Uses Thereof".

The components of the combination product are in the same formulation or in separate formulations.

In a preferred embodiment the combination product comprises a compound of formula (I) or a pharmaceutically acceptable salt or co-crystal thereof, and one or more immunotherapeutic agent useful in the treatment of cancer, specifically in immunotherapeutic treatment of cancer, such agent is selected from the group consisting of anti-PD-1PD-1 antibodies such as MDX-1106, MK3475, CT-011, AMP-224 or an anti-PD-1 antibody molecule as described in WO2015/112900 (US2015/0210769); and anti-PD-L1 antibodies such as MPDL3280A, MED14736, MDX-1105 or an anti-PD-L1 antibody molecules are disclosed in US 2016/0108123.

Example of Anti PD-L1 Antibody Molecule

In one embodiment, the combination product comprises a compound of Formula (I) or a pharmaceutically acceptable salt or co-crystal thereof, and an anti-PD-L1 antibody molecule such as those described herein.

Programmed Death Ligand 1 (PD-L1) has been described as a ligand for the immunoinhibitory receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) *Blood* 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev Immunol.* 2:116-26; Keir et al. (2008) *Annu Rev Immunol.* 26:677-704). PD-1 blockade can inhibit hematogenous spread of poorly immunogenic tumor cells by enhanced recruitment of effector T cells (Iwai et al. (2005) *Int. Immunol.* 17:133-144).

Anti-PD-L1 can enhance T-cell immunity, e.g., through blocking both its inhibitory interactions with PD-1 and B7-1. Anti-PD-1 can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

In some embodiments, the anti-PD-L1 antibody molecule is chosen from YW243.55.S70, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in WO2013/
079174)
                                         (SEQ ID NO: 245)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

Light chain (SEQ ID NO: 25 as disclosed in WO2013/
079174)
                                         (SEQ ID NO: 246)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In one embodiment, the PD-L1 inhibitor is YW243.55.S70. The YW243.55.S70 antibody is an anti-PD-L1 described in WO 2010/077634 (heavy and light chain variable region sequences shown in SEQ ID NOs. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In another embodiment, the PD-L1 inhibitor is an anti-PD-L1 antibody molecule disclosed in US 2016/0108123, filed Oct. 13, 2015, entitled "Antibody Molecules to PD-L1 and Uses Thereof," incorporated by reference in its entirety.

In one embodiment, the anti-PD-L1 antibody molecule includes at least one or two heavy chain variable domains (optionally including a constant region), at least one or two light chain variable domains (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In one embodiment, the anti-PD-L1 antibody molecule includes at least one, two or three CDRs or hypervariable loops from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, according to the Kabat and Chothia definition (e.g., at least one, two, or three CDRs or hypervariable loops according to the Kabat and Chothia definition as set out in Table 1 of US 2016/0108123); or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1 of US 2016/0108123.

In one embodiment, the anti-PD-L1 antibody molecule can include VH CDR1 according to Kabat et al. ((1991), "Sequences of Proteins of Immunological Interest," 5th Ed. Public Health Service, National Institutes of Health, Bethesda, Md.) or VH hypervariable loop 1 according to Chothia et al. (1992) *J. Mol. Biol.* 227:799-817, or a combination thereof, e.g., as shown in Table 1 of US 2016/0108123. In one embodiment, the combination of Kabat and Chothia CDR of VH CDR1 comprises the amino acid sequence GYTFTSYWMY (SEQ ID NO: 244), or an amino acid sequence substantially identical thereto (e.g., having at least one amino acid alteration, but not more than two, three or four alterations (e.g., substitutions, deletions, or insertions, e.g., conservative substitutions)). The anti-PD-L1 antibody molecule can further include, e.g., VH CDRs 2-3 according to Kabat et al. and VL CDRs 1-3 according to Kabat et al., e.g., as shown in Table 1 of US 2016/0108123.

In a preferred embodiment, the anti PD-L1 antibody molecule for use in the invention comprises:

(a) a heavy chain variable region (VH) comprising a VHCDR1 amino acid sequence of SEQ ID NO: 228, a VHCDR2 amino acid sequence of SEQ ID NO: 229, and a VHCDR3 amino acid sequence of SEQ ID NO: 227; and a light chain variable region (VL) comprising a VLCDR1 amino acid sequence of SEQ ID NO: 233, a VLCDR2 amino acid sequence of SEQ ID NO: 234, and a VLCDR3 amino acid sequence of SEQ ID NO: 235;

(b) a VH comprising a VHCDR1 amino acid sequence of SEQ ID NO: 225; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232;

(c) a VH comprising a VHCDR1 amino acid sequence of SEQ ID NO: 244, a VHCDR2 amino acid sequence of SEQ ID NO: 229, and a VHCDR3 amino acid sequence of SEQ ID NO: 227; and a VL comprising a VLCDR1 amino acid sequence of SEQ ID NO: 233, a VLCDR2 amino acid sequence of SEQ ID NO: 234, and a VLCDR3 amino acid sequence of SEQ ID NO: 235; or (d) a VH comprising a VHCDR1 amino acid sequence of SEQ ID NO: 244; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232.

In one aspect of the previous embodiment, the anti-PD-L1 antibody molecule for use in the invention comprises a heavy chain variable domain comprising the amino acid sequence of SEQ ID NO: 236 and a light chain variable domain comprising the amino acid sequence of SEQ ID NO: 239.

In one aspect of the previous embodiment, the anti-PD-L1 antibody molecule for use in the invention comprises a heavy chain comprising the amino acid sequence of SEQ ID NO: 243 and a light chain comprising the amino acid sequence of SEQ ID NO: 241.

TABLE A

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

| BAP058-hum13-HC | | |
| --- | --- | --- |
| SEQ ID NO: 244 (Chothia and Kabat combined) | HCDR1 | GYTFTSYWMY |
| SEQ ID NO: 225 (Kabat) | HCDR1 | SYWMY |
| SEQ ID NO: 226 (Kabat) | HCDR2 | RIDPNSGSTKYNEKFKN |
| SEQ ID NO: 227 (Kabat) | HCDR3 | DYRKGLYAMDY |

TABLE A-continued

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

| SEQ ID NO: 228 (Chothia) | HCDR1 | GYTFTSY |
|---|---|---|
| SEQ ID NO: 229 (Chothia) | HCDR2 | DPNSGS |
| SEQ ID NO: 227 (Chothia) | HCDR3 | DYRKGLYAMDY |
| SEQ ID NO: 236 | VH | EVQLVQSGAEVKKPGATVKISCKVSGYTFTSYWMYWV RQARGQRLEWIGRIDPNSGSTKYNEKFKNRFTISRDNS KNTLYLQMNSLRAEDTAVYYCARDYRKGLYAMDYWG QGTTVTVSS |
| SEQ ID NO: 237 | DNA VH | GAGGTCCAGCTGGTACAGTCTGGGGCTGAGGTGAA GAAGCCTGGGGCTACAGTGAAAATCTCCTGCAAGGT TTCTGGCTACACCTTCACCAGTTACTGGATGTACTGG GTGCGACAGGCTCGTGGACAACGCCTTGAGTGGATA GGTAGGATTGATCCTAATAGTGGGAGTACTAAGTAC AATGAGAAGTTCAAGAACAGATTCACCATCTCCAGA GACAATTCCAAGAACACGCTGTATCTTCAAATGAAC AGCCTGAGAGCCGAGGACACGGCCGTGTATTACTGT GCAAGGGACTATAGAAAGGGGCTCTATGCTATGGA CTACTGGGGCCAGGGCACCACCGTGACCGTGTCCTC C |
| SEQ ID NO: 243 | Heavy Chain | EVQLVQSGAEVKKPGATVKISCKVSGYTFTSYWMYWV RQARGQRLEWIGRIDPNSGSTKYNEKFKNRFTISRDNS KNTLYLQMNSLRAEDTAVYYCARDYRKGLYAMDYWG QGTTVTVSSASTKGPSVFPLAPCSRSTSESTAALGCLVK DYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVD VSQEDPEVQFNWYVDGVEVHNAKTKPREEQFNSTYR VVSVLTVLHQDWLNGKEYKCKVSNKGLPSSIEKTISKAK GQPREPQVYTLPPSQEEMTKNQVSLTCLVKGFYPSDIA VEWESNGQPENNYKTTPPVLDSDGSFFLYSRLTVDKSR WQEGNVFSCSVMHEALHNHYTQKSLSLSLGK |
| SEQ ID NO: 238 | DNA Heavy Chain | GAGGTCCAGCTGGTACAGTCTGGGGCTGAGGTGAA GAAGCCTGGGGCTACAGTGAAAATCTCCTGCAAGGT TTCTGGCTACACCTTCACCAGTTACTGGATGTACTGG GTGCGACAGGCTCGTGGACAACGCCTTGAGTGGATA GGTAGGATTGATCCTAATAGTGGGAGTACTAAGTAC AATGAGAAGTTCAAGAACAGATTCACCATCTCCAGA GACAATTCCAAGAACACGCTGTATCTTCAAATGAAC AGCCTGAGAGCCGAGGACACGGCCGTGTATTACTGT GCAAGGGACTATAGAAAGGGGCTCTATGCTATGGA CTACTGGGGCCAGGGCACCACCGTGACCGTGTCCTC CGCTTCCACCAAGGGCCCATCCGTCTTCCCCCTGGCG CCCTGCTCCAGGAGCACCTCCGAGAGCACAGCCGCC CTGGGCTGCCTGGTCAAGGACTACTTCCCCGAACCG GTGACGGTGTCGTGGAACTCAGGCGCCCTGACCAGC GGCGTGCACACCTTCCCGGCTGTCCTACAGTCCTCAG GACTCTACTCCCTCAGCAGCGTGGTGACCGTGCCCTC CAGCAGCTTGGGCACGAAGACCTACACCTGCAACGT AGATCACAAGCCCAGCAACACCAAGGTGGACAAGA GAGTTGAGTCCAAATATGGTCCCCCATGCCCACCGT GCCCAGCACCTGAGTTCCTGGGGGGACCATCAGTCT TCCTGTTCCCCCCAAAACCCAAGGACACTCTCATGAT CTCCCGGACCCCTGAGGTCACGTGCGTGGTGGTGGA CGTGAGCCAGGAAGACCCCGAGGTCCAGTTCAACTG GTACGTGGATGGCGTGGAGGTGCATAATGCCAAGA CAAAGCCGCGGGAGGAGCAGTTCAACAGCACGTAC CGTGTGGTCAGCGTCCTCACCGTCCTGCACCAGGAC TGGCTGAACGGCAAGGAGTACAAGTGCAAGGTGTC CAACAAAGGCCTCCCGTCCTCCATCGAGAAAACCAT CTCCAAAGCCAAAGGGCAGCCCCGAGAGCCACAGG TGTACACCCTGCCCCCATCCCAGGAGGAGATGACCA AGAACCAGGTCAGCCTGACCTGCCTGGTCAAAGGCT TCTACCCCAGCGACATCGCCGTGGAGTGGGAGAGCA ATGGGCAGCCGGAGAACAACTACAAGACCACGCCTC CCGTGCTGGACTCCGACGGCTCCTTCTTCCTCTACAG CAGGCTAACCGTGGACAAGAGCAGGTGGCAGGAGG GGAATGTCTTCTCATGCTCCGTGATGCATGAGGCTCT GCACAACCACTACACACAGAAGAGCCTCTCCCTGTCT CTGGGTAAA |

TABLE A-continued

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

BAP058-hum13-LC

| | | | |
|---|---|---|---|
| SEQ ID NO: 230 | (Kabat) | LCDR1 | KASQDVGTAVA |
| SEQ ID NO: 231 | (Kabat) | LCDR2 | WASTRHT |
| SEQ ID NO: 232 | (Kabat) | LCDR3 | QQYNSYPLT |
| SEQ ID NO: 233 | (Chothia) | LCDR1 | SQDVGTA |
| SEQ ID NO: 234 | (Chothia) | LCDR2 | WAS |
| SEQ ID NO: 235 | (Chothia) | LCDR3 | YNSYPL |
| SEQ ID NO: 239 | | VL | AIQLTQSPSSLSASVGDRVTITCKASQDVGTAVAWYLQ KPGQSPQLLIYWASTRHTGVPSRFSGSGSGTDFTFTISS LEAEDAATYYCQQYNSYPLTFGQGTKVEIK |
| SEQ ID NO: 240 | | DNA VL | GCCATCCAGTTGACCCAGTCTCCATCCTCCCTGTCTG CATCTGTAGGAGACAGAGTCACCATCACTTGCAAGG CCAGTCAGGATGTGGGTACTGCTGTAGCCTGGTACC TGCAGAAGCCAGGGCAGTCTCCACAGCTCCTGATCT ATTGGGCATCCACCCGGCACACTGGGGTCCCCTCGA GGTTCAGTGGCAGTGGATCTGGGACAGATTTCACCT TTACCATCAGTAGCCTGGAAGCTGAAGATGCTGCAA CATATTACTGTCAGCAGTATAACAGCTATCCTCTCAC GTTCGGCCAAGGGACCAAGGTGGAAATCAAA |
| SEQ ID NO: 241 | | Light Chain | AIQLTQSPSSLSASVGDRVTITCKASQDVGTAVAWYLQ KPGQSPQLLIYWASTRHTGVPSRFSGSGSGTDFTFTISS LEAEDAATYYCQQYNSYPLTFGQGTKVEIKRTVAAPSV FIFPPSDEQLKSGTASVVCLLNNFYPREAKVQWKVDNA LQSGNSQESVTEQDSKDSTYSLSSTLTLSKADYEKHKVY ACEVTHQGLSSPVTKSFNRGEC |
| SEQ ID NO: 242 | | DNA Light Chain | GCCATCCAGTTGACCCAGTCTCCATCCTCCCTGTCTG CATCTGTAGGAGACAGAGTCACCATCACTTGCAAGG CCAGTCAGGATGTGGGTACTGCTGTAGCCTGGTACC TGCAGAAGCCAGGGCAGTCTCCACAGCTCCTGATCT ATTGGGCATCCACCCGGCACACTGGGGTCCCCTCGA GGTTCAGTGGCAGTGGATCTGGGACAGATTTCACCT TTACCATCAGTAGCCTGGAAGCTGAAGATGCTGCAA CATATTACTGTCAGCAGTATAACAGCTATCCTCTCAC GTTCGGCCAAGGGACCAAGGTGGAAATCAAACGTA CGGTGGCTGCACCATCTGTCTTCATCTTCCCGCCATC TGATGAGCAGTTGAAATCTGGAACTGCCTCTGTTGT GTGCCTGCTGAATAACTTCTATCCCAGAGAGGCCAA AGTACAGTGGAAGGTGGATAACGCCCTCCAATCGG GTAACTCCCAGGAGAGTGTCACAGAGCAGGACAGC AAGGACAGCACCTACAGCCTCAGCAGCACCCTGACG CTGAGCAAAGCAGACTACGAGAAACACAAAGTCTAC GCCTGCGAAGTCACCCATCAGGGCCTGAGCTCGCCC GTCACAAAGAGCTTCAACAGGGGAGAGTGT |

Examples of Anti PD-1 Antibody Molecule

In a preferred embodiment, the combination product comprises a compound of Formula (I) or a pharmaceutically acceptable salt or co-crystal thereof, and an anti-PD-1 antibody molecule such as those described herein.

PD-1 is a CD28/CTLA-4 family member expressed, e.g., on activated CD4$^+$ and CD8$^+$ T cells, T$_{regs}$, and B cells. It negatively regulates effector T cell signaling and function. PD-1 is induced on tumor-infiltrating T cells, and can result in functional exhaustion or dysfunction (Keir et al. (2008) *Annu. Rev. Immunol.* 26:677-704; Pardoll et al. (2012) *Nat Rev Cancer* 12(4):252-64). PD-1 delivers a coinhibitory signal upon binding to either of its two ligands, Programmed Death-Ligand 1 (PD-L1) or Programmed Death-Ligand 2 (PD-L2). PD-L1 is expressed on a number of cell types, including T cells, Natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) *Annu. Rev. Immunol.* 26:677-704; Pardoll et al. (2012) *Nat Rev Cancer* 12(4):252-64). PD-L2 is expressed on dendritic cells, macrophages, and some tumors. Blockade of the PD-1 pathway has been pre-clinically and clinically validate for cancer immunotherapy. Both preclinical and clinical studies have demonstrated that anti-PD-1 blockade can restore activity of effector T cells and results in robust anti-tumor response. For example, blockade of PD-1 pathway can restore exhausted/dysfunctional effector T cell function (e.g. proliferation, IFN-g secretion, or cytolytic function) and/or inhibit T$_{reg}$ cell function (Keir et al. (2008) *Annu. Rev. Immunol.* 26:677-704; Pardoll et al. (2012) *Nat Rev Cancer* 12(4):252-64). Blockade of the PD-1 pathway can be effected with an antibody, an antigen binding fragment thereof, an immunoadhesin, a fusion protein, or oligopeptide of PD-1, PD-L1 and/or PD-L2.

In one embodiment, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

The heavy and light chain amino acid sequences of Nivolumab are as follows:

```
Heavy chain
                                              (SEQ ID NO: 247)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK
```

```
Light chain
                                              (SEQ IS NO: 248)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. The heavy and light chain amino acid sequences of Pembrolizumab are as follows:

```
Heavy chain
                                                         (SEQ ID NO: 249)
QVQLVQSGVE  VKKPGASVKV  SCKASGYTFT  NYYMYWVRQA  PGQGLEWMGG   50

INPSNGGTNF  NEKFKNRVTL  TTDSSTTTAY  MELKSLQFDD  TAVYYCARRD  100

YRFDMGFDYW  GQGTTVTVSS  ASTKGPSVFP  LAPCSRSTSE  STAALGCLVK  150

DYFPEPVTVS  WNSGALTSGV  HTFPAVLQSS  GLYSLSSVVT  VPSSSLGTKT  200

YTCNVDHKPS  NTKVDKRVES  KYGPPCPPCP  APEFLGGPSV  FLFPPKPKDT  250

LMISRTPEVT  CVVVDVSQED  PEVQFNWYVD  GVEVHNAKTK  PREEQFNSTY  300

RVVSVLTVLH  QDWLNGKEYK  CKVSNKGLPS  SIEKTISKAK  GQPREPQVYT  350

LPPSQEEMTK  NQVSLTCLVK  GFYPSDIAVE  WESNGQPENN  YKTTPPVLDS  400

DGSFFLYSRL  TVDKSRWQEG  NVFSCSVMHE  ALHNHYTQKS  LSLSLGK     447

Ligh chain
                                                         (SEQ ID NO: 250)
EIVLTQSPAT  LSLSPGERAT  LSCRASKGVS  TSGYSYLHWY  QQKPGQAPRL   50

LIYLASYLES  GVPARFSGSG  SGTDFTLTIS  SLEPEDFAVY  YCQHSRDLPL  100

TFGGGTKVEI  KRTVAAPSVF  IFPPSDEQLK  SGTASVVCLL  NNFYPREAKV  150

QWKVDNA     LQS GNSQESVTEQ  DSKDSTYSLS  STLTLSKADY  EKHKVYACEV 200

THQGLSSPVT  KSFNRGEC                                        218'
```

In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

Other anti-PD-1 antibodies include AMP 514 (Amplimmune), among others, e.g., anti-PD-1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-LI or PD-L2 fused to a constant region (e.g., an Fc region of an immunoglobulin sequence). In some embodiments, the PD-1 inhibitor is AMP-224 (137-DCIg; Amplimmune; e.g., disclosed in WO2010/027827 and WO2011/066342), is a PD-L2 Fc fusion soluble receptor that blocks the interaction between PD-1 and 137-H1.

In a more preferred embodiment, the anti-PD-1 antibody is an anti-PD-1 antibody molecule as described in WO2015/112900 (US2015/0210769), published on Jul. 30, 2015, entitled "Antibody Molecules to PD-1 and Uses Thereof," incorporated by reference in its entirety.

In some embodiments, the anti-PD-1 antibody molecule (e.g., an isolated or recombinant antibody molecule) has one or more of the following properties:

(i) binds to PD-1, e.g., human PD-1, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;

(ii) does not substantially bind to CD28, CTLA-4, ICOS or BTLA;

(iii) inhibits or reduces binding of PD-1 to a PD-1 ligand, e.g., PD-L1 or PD-L2, or both;

(iv) binds specifically to an epitope on PD-1, e.g., the same or similar epitope as the epitope recognized by murine monoclonal antibody BAP049 or a chimeric antibody BAP049, e.g., BAP049-chi or BAP049-chi-Y;

(v) shows the same or similar binding affinity or specificity, or both, as any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(vi) shows the same or similar binding affinity or specificity, or both, as an antibody molecule (e.g., an heavy chain variable region and light chain variable region) described in Table B;

(vii) shows the same or similar binding affinity or specificity, or both, as an antibody molecule (e.g., an heavy chain variable region and light chain variable region) having an amino acid sequence shown in Table B;

(viii) shows the same or similar binding affinity or specificity, or both, as an antibody molecule (e.g., an heavy chain variable region and light chain variable region) encoded by the nucleotide sequence shown in Table B;

(ix) inhibits, e.g., competitively inhibits, the binding of a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(x) binds the same or an overlapping epitope with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xi) competes for binding, and/or binds the same epitope, with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xii) has one or more biological properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiii) has one or more pharmacokinetic properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiv) inhibits one or more activities of PD-1, e.g., results in one or more of: an increase in tumor infiltrating lymphocytes, an increase in T-cell receptor mediated proliferation, or a decrease in immune evasion by cancerous cells;

(xv) binds human PD-1 and is cross-reactive with cynomolgus PD-1;

(xvi) binds to one or more residues within the C strand, CC' loop, C' strand, or FG loop of PD-1, or a combination two, three or all of the C strand, CC' loop, C' strand or FG loop of PD-1, e.g., wherein the binding is assayed using ELISA or Biacore; or (xvii) has a VL region that contributes more to binding to PD-1 than a VH region.

In some embodiments, the antibody molecule binds to PD-1 with high affinity, e.g., with a $K_D$ that is about the same, or at least about 10%, 20%, 30%, 40%, 50%, 60%, 70%, 80% or 90% higher or lower than the $K_D$ of a murine or chimeric anti-PD-1 antibody molecule, e.g., a murine or chimeric anti-PD-1 antibody molecule described herein. In some embodiments, the $K_D$ of the murine or chimeric anti-PD-1 antibody molecule is less than about 0.4, 0.3, 0.2, 0.1, or 0.05 nM, e.g., measured by a Biacore method. In some embodiments, the $K_D$ of the murine or chimeric anti-PD-1 antibody molecule is less than about 0.2 nM, e.g., about 0.135 nM. In other embodiments, the $K_D$ of the murine or chimeric anti PD-1 antibody molecule is less than about 10, 5, 3, 2, or 1 nM, e.g., measured by binding on cells expressing PD-1 (e.g., 300.19 cells). In some embodiments, the $K_D$ of the murine or chimeric anti PD-1 antibody molecule is less than about 5 nM, e.g., about 4.60 nM (or about 0.69 µg/mL).

In some embodiments, the anti-PD-1 antibody molecule binds to PD-1 with a $K_{off}$ slower than $1\times10^{-4}$, $5\times10^{-5}$, or $1\times10^{-5}$ $s^{-1}$, e.g., about $1.65\times10^{-5}$ $s^{-1}$. In some embodiments, the anti-PD-1 antibody molecule binds to PD-1 with a $K_{on}$ faster than $1 \times 10^4$, $5 \times 10^4$, $1 \times 10^5$, or $5 \times 10^5$ M$^{-1}$s$^{-1}$, e.g., about $1.23 \times 10^5$ M$^{-1}$s$^{-1}$.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine or chimeric anti-PD-1 antibody molecule described herein. In some embodiments, the antibody molecule is expressed in CHO cells.

In some embodiments, the anti-PD-1 antibody molecule reduces one or more PD-1-associated activities with an IC$_{50}$ (concentration at 50% inhibition) that is about the same or lower, e.g., at least about 10%, 20%, 30%, 40%, 50%, 60%, 70%, 80% or 90% lower, than the IC$_{50}$ of a murine or chimeric anti-PD-1 antibody molecule, e.g., a murine or chimeric anti-PD-1 antibody molecule described herein. In some embodiments, the IC$_{50}$ of the murine or chimeric anti-PD-1 antibody molecule is less than about 6, 5, 4, 3, 2, or 1 nM, e.g., measured by binding on cells expressing PD-1 (e.g., 300.19 cells). In some embodiments, the IC$_{50}$ of the murine or chimeric anti-PD-1 antibody molecule is less than about 4 nM, e.g., about 3.40 nM (or about 0.51 µg/mL). In some embodiments, the PD-1-associated activity reduced is the binding of PD-L1 and/or PD-L2 to PD-1. In some embodiments, the anti-PD-1 antibody molecule binds to peripheral blood mononucleated cells (PBMCs) activated by Staphylococcal enterotoxin B (SEB). In other embodiments, the anti-PD-1 antibody molecule increases the expression of IL-2 on whole blood activated by SEB. For example, the anti-PD-1 antibody increases the expression of IL-2 by at least about 2, 3, 4, or 5-fold, compared to the expression of IL-2 when an isotype control (e.g., IgG4) is used.

In some embodiments, the anti-PD-1 antibody molecule has improved stability, e.g., at least about 0.5, 1, 2, 3, 4, 5, 6, 7, 8, 9 or 10-fold more stable in vivo or in vitro, than a murine or chimeric anti-PD-1 antibody molecule, e.g., a murine or chimeric anti-PD-1 antibody molecule described herein.

In one embodiment, the anti PD-1 antibody molecule is a humanized antibody molecule and has a risk score based on T cell epitope analysis of 300 to 700, 400 to 650, 450 to 600, or a risk score as described herein.

In another embodiment, the anti-PD-1 antibody molecule comprises at least one antigen-binding region, e.g., a variable region or an antigen-binding fragment thereof, from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two heavy chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two light chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes a heavy chain constant region for an IgG4, e.g., a human IgG4. In one embodiment, the human IgG4 includes a substitution at position 228 according to EU numbering (e.g., a Ser to Pro substitution). In still another embodiment, the anti-PD-1 antibody molecule includes a heavy chain constant region for an IgG1, e.g., a human IgG1. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235). In one embodiment, the heavy chain constant region comprises an amino sequence set forth in Table D, or a sequence substantially identical (e.g., at least 80%, 85%, 90%, 92%, 95%, 97%, 98%, 99% or higher identical) thereto.

In yet another embodiment, the anti-PD-1 antibody molecule includes a kappa light chain constant region, e.g., a human kappa light chain constant region. In one embodiment, the light chain constant region comprises an amino sequence set forth in Table D, or a sequence substantially identical (e.g., at least 80%, 85%, 90%, 92%, 95%, 97%, 98%, 99% or higher identical) thereto.

In another embodiment, the anti-PD-1 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table D, or a sequence substantially identical (e.g., at least 80%, 85%, 90%, 92%, 95%, 97%, 98%, 99% or higher identical) thereto. In one embodiment, the human IgG4 includes a substitution at position 228 according to EU numbering (e.g., a Ser to Pro substitution). In yet another embodiment, the anti-PD-1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table D, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235).

In another embodiment, the anti-PD-1 antibody molecule includes a heavy chain variable domain and a constant region, a light chain variable domain and a constant region, or both, comprising the amino acid sequence of BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three complementarity determining regions (CDRs) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table B, or encoded by a nucleotide sequence shown in Table B. In one embodiment, one or more of the CDRs (or collectively all of the CDRs) have one, two, three, four, five, six or more changes, e.g., amino acid substitutions or deletions, relative to the amino acid sequence shown in Table B, or encoded by a nucleotide sequence shown in Table B.

In yet another embodiment, the anti-PD-1 antibody molecule includes at least one, two, or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequence.

In yet another embodiment, the anti-PD-1 antibody molecule includes at least one, two, or three CDRs (or collectively all of the CDRs) from a light chain variable region comprising an amino acid sequence shown in Table B, or encoded by a nucleotide sequence shown in Table B. In one embodiment, one or more of the CDRs (or collectively all of the CDRs) have one, two, three, four, five, six or more changes, e.g., amino acid substitutions or deletions, relative to the amino acid sequence shown in Table B, or encoded by a nucleotide sequence shown in Table B. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table B (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table B, or encoded by a nucleotide sequence shown in Table B. In one embodiment, one or more of the CDRs (or collectively all of the CDRs) have one, two, three, four, five, six or more changes, e.g., amino acid substitutions or deletions, relative to the amino acid sequence shown in Table B, or encoded by a nucleotide sequence shown in Table B.

In one embodiment, the anti-PD-1 antibody molecule includes all six CDRs from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-PD-1 antibody molecule may include any CDR described herein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table B (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, or three CDRs according to Kabat et al. (e.g., at least one, two, or three CDRs according to the Kabat definition as set out in Table B) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table B.

In another embodiment, the anti-PD-1 antibody molecule includes at least one, two, or three CDRs according to Kabat et al. (e.g., at least one, two, or three CDRs according to the Kabat definition as set out in Table B) from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table B.

In yet another embodiment, the anti-PD-1 antibody molecule includes at least one, two, three, four, five, or six CDRs according to Kabat et al. (e.g., at least one, two, three, four, five, or six CDRs according to the Kabat definition as set out in Table B) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table B.

In yet another embodiment, the anti-PD-1 antibody molecule includes all six CDRs according to Kabat et al. (e.g., all six CDRs according to the Kabat definition as set out in Table B) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table B. In one embodiment, the anti-PD-1 antibody molecule may include any CDR described herein.

In another embodiment, the anti-PD-1 antibody molecule includes at least one, two, or three Chothia hypervariable loops (e.g., at least one, two, or three hypervariable loops according to the Chothia definition as set out in Table B) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table B.

In another embodiment, the anti-PD-1 antibody molecule includes at least one, two, or three Chothia hypervariable loops (e.g., at least one, two, or three hypervariable loops according to the Chothia definition as set out in Table B) of a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table B.

In yet another embodiment, the anti-PD-1 antibody molecule includes at least one, two, three, four, five, or six hypervariable loops (e.g., at least one, two, three, four, five, or six hypervariable loops according to the Chothia definition as set out in Table B) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table B, or encoded by the nucleotide sequence in Table B; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table B.

In one embodiment, the anti-PD-1 antibody molecule includes all six hypervariable loops (e.g., all six hypervariable loops according to the Chothia definition as set out in Table B) of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table B. In one embodiment, the anti-PD-1 antibody molecule may include any hypervariable loop described herein.

In still another embodiment, the anti-PD-1 antibody molecule includes at least one, two, or three hypervariable loops that have the same canonical structures as the corresponding hypervariable loop of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-PD-1 antibody molecule includes a combination of CDRs or hypervariable loops defined according to the Kabat et al. and Chothia et al.

In one embodiment, the anti-PD-1 antibody molecule includes at least one, two or three CDRs or hypervariable loops from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs or hypervariable loops according to the Kabat and Chothia definition as set out in Table B); or encoded by the nucleotide sequence in Table B; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table B.

For example, the anti-PD-1 antibody molecule can include VH CDR1 according to Kabat et al. or VH hypervariable loop 1 according to Chothia et al., or a combination thereof, e.g., as shown in Table B. In one embodiment, the combination of Kabat and Chothia CDR of VH CDR1 comprises the amino acid sequence GYTFTTYWMH (SEQ ID NO: 224), or an amino acid sequence substantially identical thereto (e.g., having at least one amino acid alteration, but not more than two, three or four alterations (e.g., substitutions, deletions, or insertions, e.g., conservative substitutions)). The anti-PD-1 antibody molecule can further include, e.g., VH CDRs 2-3 according to Kabat et al. and VL CDRs 1-3 according to Kabat et al., e.g., as shown in Table B. Accordingly, in some embodiments, framework regions are defined based on a combination of CDRs defined according to Kabat et al. and hypervariable loops defined according to Chothia et al. For example, the anti-PD-1 antibody molecule can include VH FR1 defined based on VH hypervariable loop 1 according to Chothia et al. and VH FR2 defined based on VH CDRs 1-2 according to Kabat et al., e.g., as shown in Table B. The anti-PD-1 antibody molecule can further include, e.g., VH FRs 3-4 defined based on VH CDRs 2-3 according to Kabat et al. and VL FRs 1-4 defined based on VL CDRs 1-3 according to Kabat et al.

The anti-PD-1 antibody molecule can contain any combination of CDRs or hypervariable loops according to the Kabat and Chothia definitions. In one embodiment, the anti-PD-1 antibody molecule includes at least one, two or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs according to the Kabat and Chothia definition as set out in Table B).

In an embodiment, e.g., an embodiment comprising a variable region, a CDR (e.g., Chothia CDR or Kabat CDR), or other sequence referred to herein, e.g., in Table B, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments the antibody molecule is a bispecific antibody molecule having a first binding specificity for PD-1 and a second binding specificity for TIM-3, LAG-3, CEACAM (e.g., CEACAM-1 and/or CEACAM-5), PD-L1 or PD-L2.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the antibody molecule is a humanized antibody molecule. In another embodiment, the antibody molecule is a monospecific antibody molecule. In yet another embodiment, the antibody molecule is a bispecific antibody molecule.

In one embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 32.

In another embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises the VHCDR1 amino acid sequence of SEQ ID NO: 1. In another embodiment, the anti-PD-1 antibody molecule comprises the VHCDR1 amino acid sequence of SEQ ID NO: 4. In yet another embodiment, the anti-PD-1 antibody molecule comprises the VHCDR1 amino acid sequence of SEQ ID NO: 224.

In one embodiment, the light or the heavy chain variable framework (e.g., the region encompassing at least FR1, FR2, FR3, and optionally FR4) of the anti-PD-1 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-PD-1 antibody molecule comprises a heavy chain variable domain having at least one, two, three, four, five, six, seven, ten, fifteen, twenty or more changes, e.g., amino acid substitutions or deletions, from an amino acid sequence of BAP049-chi-HC, e.g., the amino acid sequence of the FR region in the entire variable region, e.g., SEQ ID NO: 18, 20, 22 or 30. In one embodiment, the anti-PD-1 antibody molecule comprises a heavy chain variable domain having one or more of: E at position 1, V at position 5, A at position 9, V at position 11, K at position 12, K at position 13, E at position 16, L at position 18, R at position 19, I or V at position 20, G at position 24, I at position 37, A or S at position 40, T at position 41, S at position 42, R at position 43, M or L at position 48, V or F at position 68, T at position 69, I at position 70, S at position 71, A or R at position 72, K or N at position 74, T or K at position 76, S or N at position 77, L at position 79, L at position 81, E or Q at position 82, M at position 83, S or N at position 84, R at position 87, A at position 88, or T at position 91 of amino acid sequence of BAP049-chi-HC, e.g., the amino acid sequence of the FR in the entire variable region, e.g., SEQ ID NO: 18, 20, 22 or 30.

Alternatively, or in combination with the heavy chain substitutions of BAP049-chi-HC described herein, the anti-PD-1 antibody molecule comprises a light chain variable domain having at least one, two, three, four, five, six, seven, ten, fifteen, twenty or more amino acid changes, e.g., amino acid substitutions or deletions, from an amino acid sequence of BAP049-chi-LC, e.g., the amino acid sequence shown in SEQ ID NO: 24 or 26. In one embodiment, the anti-PD-1 antibody molecule comprises a heavy chain variable domain having one or more of: E at position 1, V at position 2, Q at position 3, L at position 4, T at position 7, D or L or A at position 9, F or T at position 10, Q at position 11, S or P at position 12, L or A at position 13, S at position 14, P or L or V at position 15, K at position 16, Q or D at position 17, R at position 18, A at position 19, S at position 20, I or L at position 21, T at position 22, L at position 43, K at position 48, A or S at position 49, R or Q at position 51, Y at position 55, I at position 64, S or P at position 66, S at position 69, Y at position 73, G at position 74, E at position 76, F at position 79, N at position 82, N at position 83, L or I at position 84, E at position 85, S or P at position 86, D at position 87, A or F or I at position 89, T or Y at position 91, F at position 93, or Y at position 102 of the amino acid sequence of BAP049-chi-LC, e.g., the amino acid sequence SEQ ID NO: 24 or 26.

In other embodiments, the anti-PD-1 antibody molecule includes one, two, three, or four heavy chain framework regions (e.g., a VHFW amino acid sequence shown in Table C, or encoded by the nucleotide sequence shown in Table C), or a sequence substantially identical thereto.

In yet other embodiments, the anti-PD-1 antibody molecule includes one, two, three, or four light chain framework regions (e.g., a VLFW amino acid sequence shown in Table C, or encoded by the nucleotide sequence shown in Table C), or a sequence substantially identical thereto.

In other embodiments, the anti-PD-1 antibody molecule includes one, two, three, or four heavy chain framework regions (e.g., a VHFW amino acid sequence shown in Table C, or encoded by the nucleotide sequence shown in Table C), or a sequence substantially identical thereto; and one, two, three, or four light chain framework regions (e.g., a VLFW amino acid sequence shown in Table C, or encoded by the nucleotide sequence shown in Table C), or a sequence substantially identical thereto.

In some embodiments, the anti-PD-1 antibody molecule comprises the heavy chain framework region 1 (VHFW1) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum15, BAP049-hum16, BAP049-Clone-A, BAP049-Clone-B, BAP049-Clone-C, BAP049-Clone-D, or BAP049-Clone-E (e.g., SEQ ID NO: 147). In some embodiments, the antibody molecule comprises the heavy chain framework region 1 (VHFW1) of BAP049-hum14 or BAP049-hum15 (e.g., SEQ ID NO: 151).

In some embodiments, the anti-PD-1 antibody molecule comprises the heavy chain framework region 2 (VHFW2) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 153). In some embodiments, the antibody molecule comprises the heavy chain framework region 2 (VHFW2) of BAP049-hum03, BAP049-hum04, BAP049-hum08, BAP049-hum10, BAP049-hum14, BAP049-hum15, or BAP049-Clone-D (e.g., SEQ ID NO: 157). In some embodiments, the antibody molecule comprises the heavy chain framework region 2 (VHFW2) of BAP049-hum16 (e.g., SEQ ID NO: 160).

In some embodiments, the anti-PD-1 antibody molecule comprises the heavy chain framework region 3 (VHFW3) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 162). In some embodiments, the antibody molecule comprises the heavy chain framework region 3 (VHFW3) of BAP049-hum03, BAP049-hum04, BAP049-hum08, BAP049-hum10, BAP049-hum14, BAP049-hum15, BAP049-hum16, or BAP049-Clone-D (e.g., SEQ ID NO: 166).

In some embodiments, the anti-PD-1 antibody molecule comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework region 1 (VLFW1) of BAP049-hum08, BAP049-hum09, BAP049-hum15, BAP049-hum16, or BAP049-Clone-C (e.g., SEQ ID NO: 174). In some embodiments, the antibody molecule comprises the light chain framework region 1 (VLFW1) of BAP049-hum01, BAP049-hum04, BAP049-hum05, BAP049-hum07, BAP049-hum10, BAP049-hum11, BAP049-hum14, BAP049-Clone-A, BAP049-Clone-B, BAP049-Clone-D, or BAP049-Clone-E (e.g., SEQ ID NO: 177). In some embodiments, the antibody molecule comprises the light chain framework region 1 (VLFW1) of BAP049-hum06 (e.g., SEQ ID NO: 181). In some embodiments, the antibody molecule comprises the light chain framework region 1 (VLFW1) of BAP049-hum13 (e.g., SEQ ID NO: 183). In some embodiments, the antibody molecule comprises the light chain framework region 1 (VLFW1) of BAP049-hum02, BAP049-hum03, or BAP049-hum12 (e.g., SEQ ID NO: 185).

In some embodiments, the anti-PD-1 antibody molecule comprises the light chain framework region 2 (VLFW2) of BAP049-hum01, BAP049-hum02, BAP049-hum03, BAP049-hum06, BAP049-hum08, BAP049-hum09, BAP049-hum10, BAP049-hum11, BAP049-hum14, BAP049-hum15, BAP049-hum16, BAP049-Clone-A, BAP049-Clone-B, BAP049-Clone-D, or BAP049-Clone-E (e.g., SEQ ID NO: 187). In some embodiments, the antibody molecule comprises the light chain framework region 2 (VLFW2) of BAP049-hum04, BAP049-hum05, BAP049-hum07, BAP049-hum13, or BAP049-Clone-C (e.g., SEQ ID NO: 191). In some embodiments, the antibody molecule comprises the light chain framework region 2 (VLFW2) of BAP049-hum12 (e.g., SEQ ID NO: 194).

In some embodiments, the anti-PD-1 antibody molecule comprises the light chain framework region 3 (VLFW3) of BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-C, BAP049-Clone-D, or BAP049-Clone-E (e.g., SEQ ID NO: 196). In some embodiments, the antibody molecule comprises the light chain framework region 3 (VLFW3) of BAP049-hum02 or BAP049-hum03 (e.g., SEQ ID NO: 200). In some embodiments, the antibody molecule comprises the light chain framework region 3 (VLFW3) of BAP049-hum01 or BAP049-Clone-A (e.g., SEQ ID NO: 202). In some embodiments, the antibody molecule comprises the light chain framework region 3 (VLFW3) of BAP049-hum04, BAP049-hum05, or BAP049-Clone-B (e.g., SEQ ID NO: 205).

In some embodiments, the anti-PD-1 antibody molecule comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01, BAP049-hum02, BAP049-hum05, BAP049-hum06, BAP-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 147 (VHFW1), SEQ ID NO: 153 (VHFW2), and SEQ ID NO: 162 (VHFW3)). In some embodiments, the antibody molecule comprises the heavy chain framework regions 1-3 of BAP049-hum03, BAP049-hum04, BAP049-hum08, BAP049-hum10, or BAP049-Clone-D (e.g., SEQ ID NO: 147 (VHFW1), SEQ ID NO: 157 (VHFW2), and SEQ ID NO: 166 (VHFW3)). In some embodiments, the antibody molecule comprises the heavy chain framework regions 1-3 of BAP049-hum14 or BAP049-hum15 (e.g., SEQ ID NO: 151 (VHFW1), SEQ ID NO: 157 (VHFW2), and SEQ ID NO: 166 (VHFW3)). In some embodiments, the antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)). In some embodiments, the antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)). In some embodiments, the antibody molecule comprises the light chain framework regions 1-3 of BAP049-hum02 or BAP049-hum03 (e.g., SEQ ID NO: 185 (VLFW1), SEQ ID NO: 187 (VLFW2), and SEQ ID NO: 200 (VLFW3)). In some embodiments, the antibody molecule comprises the light chain framework regions 1-3 of BAP049-hum04, BAP049-hum05, or BAP049-Clone-B (e.g., SEQ ID NO: 177 (VLFW1), SEQ ID NO: 191 (VLFW2), and SEQ ID NO: 205 (VLFW3)). In some embodiments, the antibody molecule comprises the light chain framework regions 1-3 of BAP049-hum06 (e.g., SEQ ID NO: 181 (VLFW1), SEQ ID NO: 187 (VLFW2), and SEQ ID NO: 196 (VLFW3)). In some embodiments, the antibody molecule comprises the light chain framework regions 1-3 of BAP049-hum07 (e.g., SEQ ID NO: 177 (VLFW1), SEQ ID NO: 191 (VLFW2), and SEQ ID NO: 196 (VLFW3)). In some embodiments, the antibody molecule comprises the light chain framework regions 1-3 of BAP049-hum08, BAP049-hum09, BAP049-hum15, BAP049-hum16, or BAP049-Clone-C (e.g., SEQ ID NO: 174 (VLFW1), SEQ ID NO: 187 (VLFW2), and SEQ ID NO: 196 (VLFW3)). In some embodiments, the antibody molecule comprises the light chain framework regions 1-3 of BAP049-hum10, BAP049-hum11, BAP049-hum14, BAP049-Clone-D, or BAP049-Clone-E (e.g., SEQ ID NO: 177 (VLFW1), SEQ ID NO: 187 (VLFW2), and SEQ ID NO: 196 (VLFW3)). In some embodiments, the antibody molecule comprises the light chain framework regions 1-3 of BAP049-hum12 (e.g., SEQ ID NO: 185 (VLFW1), SEQ ID NO: 194 (VLFW2), and SEQ ID NO: 196 (VLFW3)). In some embodiments, the antibody molecule comprises the light chain framework regions 1-3 of BAP049-hum13 (e.g., SEQ ID NO: 183 (VLFW1), SEQ ID NO: 191 (VLFW2), and SEQ ID NO: 196 (VLFW3)). In some embodiments, the antibody molecule further comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01 or BAP049-Clone-A (e.g., SEQ ID NO: 147 (VHFW1), SEQ ID NO: 153 (VHFW2), and SEQ ID NO: 162 (VHFW3)) and the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)).

In some embodiments, the anti-PD-1 antibody molecule comprises the heavy chain framework regions 1-3 of BAP049-hum02 (e.g., SEQ ID NO: 147 (VHFW1), SEQ ID NO: 153 (VHFW2), and SEQ ID NO: 162 (VHFW3)) and the light chain framework regions 1-3 of BAP049-hum02 (e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum03 (e.g., SEQ ID NO: 147 (VHFW1), SEQ ID NO: 157 (VHFW2), and SEQ ID NO: 166 (VHFW3)) and the light chain framework regions 1-3 of BAP049-hum03

(e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum04 (e.g., SEQ ID NO: 147 (VHFW1), SEQ ID NO: 157 (VHFW2), and SEQ ID NO: 166 (VHFW3)) and the light chain framework regions 1-3 of BAP049-hum04 (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum05 or BAP049-Clone-B (e.g., SEQ ID NO: 147 (VHFW1), SEQ ID NO: 153 (VHFW2), and SEQ ID NO: 162 (VHFW3)) and the light chain framework regions 1-3 of BAP049-hum05 or BAP049-Clone-B (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum06 (e.g., SEQ ID NO: 147 (VHFW1), SEQ ID NO: 153 (VHFW2), and SEQ ID NO: 162 (VHFW3)) and the light chain framework regions 1-3 of BAP049-hum06 (e.g., SEQ ID NO: 181 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum07 (e.g., SEQ ID NO: 147 (VHFW1), SEQ ID NO: 153 (VHFW2), and SEQ ID NO: 162 (VHFW3)) and the light chain framework regions 1-3 of BAP049-hum07 (e.g., SEQ ID NO: 177 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum08 (e.g., SEQ ID NO: 147 (VHFW1), SEQ ID NO: 157 (VHFW2), and SEQ ID NO: 166 (VHFW3)) and the light chain framework regions 1-3 of BAP049-hum08 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum09 or BAP049-Clone-C (e.g., SEQ ID NO: 147 (VHFW1), SEQ ID NO: 153 (VHFW2), and SEQ ID NO: 162 (VHFW3)) and the light chain framework regions 1-3 of BAP049-hum09 or BAP049-Clone-C (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum10 or BAP049-Clone-D (e.g., SEQ ID NO: 147 (VHFW1), SEQ ID NO: 157 (VHFW2), and SEQ ID NO: 166 (VHFW3)) and the light chain framework regions 1-3 of BAP049-hum10 or BAP049-Clone-D (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum11 or BAP049-Clone-E (e.g., SEQ ID NO: 147 (VHFW1), SEQ ID NO: 153 (VHFW2), and SEQ ID NO: 162 (VHFW3)) and the light chain framework regions 1-3 of BAP049-hum11 or BAP049-Clone-E (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum12 (e.g., SEQ ID NO: 147 (VHFW1), SEQ ID NO: 153 (VHFW2), and SEQ ID NO: 162 (VHFW3)) and the light chain framework regions 1-3 of BAP049-hum12 (e.g., SEQ ID NO: 185 (VLFW1), SEQ ID NO: 194 (VLFW2), and SEQ ID NO: 196 (VLFW3)).

In some embodiments, the anti-PD-1 antibody molecule comprises the heavy chain framework regions 1-3 of BAP049-hum13 (e.g., SEQ ID NO: 147 (VHFW1), SEQ ID NO: 153 (VHFW2), and SEQ ID NO: 162 (VHFW3)) and the light chain framework regions 1-3 of BAP049-hum13 (e.g., SEQ ID NO: 183 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum14 (e.g., SEQ ID NO: 151 (VHFW1), SEQ ID NO: 157 (VHFW2), and SEQ ID NO: 166 (VHFW3)) and the light chain framework regions 1-3 of BAP049-hum14 (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum15 (e.g., SEQ ID NO: 151 (VHFW1), SEQ ID NO: 157 (VHFW2), and SEQ ID NO: 166 (VHFW3)) and the light chain framework regions 1-3 of BAP049-hum15 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)) and the light chain framework regions 1-3 of BAP049-hum16 (e.g., SEQ ID NO: 174 (VLFW1), SEQ ID NO: 187 (VLFW2), and SEQ ID NO: 196 (VLFW3)).

In some embodiments, the anti-PD-1 antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169) and the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises a heavy chain framework region having a combination of framework regions FW1, FW2 and FW3 as show in FIG. 9 or 10. In other embodiment, the antibody molecule comprises a light chain framework region having a combination of framework regions FW1, FW2 and FW3 as show in FIG. 9 or 10. In yet other embodiments, the antibody molecule comprises a heavy chain framework region having a combination of framework regions FW1, FW2 and FW3 as show in FIG. 9 or 10, and a light chain framework region having a combination of framework regions FW1, FW2 and FW3 as shown in FIG. 9 or 10.

In one embodiment, the heavy or light chain variable domain, or both, of the anti-PD-1 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-Clone-A, BAP049-Clone-B, BAP049-Clone-C, BAP049-Clone-D, or BAP049-Clone-E; or as described in Table B, or encoded by the nucleotide sequence in Table B; or which differs at least 1 or 5 residues, but less than 40, 30, 20, or 10 residues, from a variable region of an antibody described herein.

In one embodiment, the heavy or light chain variable region, or both, of the anti-PD-1 antibody molecule includes an amino acid sequence encoded by a nucleic acid sequence described herein or a nucleic acid that hybridizes to a nucleic acid sequence described herein (e.g., a nucleic acid sequence as shown in Tables 1 and 2) or its complement, e.g., under low stringency, medium stringency, or high stringency, or other hybridization condition described herein.

In another embodiment, the anti-PD-1 antibody molecule comprises at least one, two, three, or four antigen-binding regions, e.g., variable regions, having an amino acid sequence as set forth in Table B, or a sequence substantially identical thereto (e.g., a sequence at least about 85%, 90%, 95%, 99% or more identical thereto, or which differs by no more than 1, 2, 5, 10, or 15 amino acid residues from the sequences shown in Table B. In another embodiment, the anti-PD-1 antibody molecule includes a VH and/or VL domain encoded by a nucleic acid having a nucleotide sequence as set forth in Table B, or a sequence substantially identical thereto (e.g., a sequence at least about 85%, 90%, 95%, 99% or more identical thereto, or which differs by no more than 3, 6, 15, 30, or 45 nucleotides from the sequences shown in Table B.

In yet another embodiment, the anti-PD-1 antibody molecule comprises at least one, two, or three CDRs from a heavy chain variable region having an amino acid sequence as set forth in Table B, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, or three CDRs from a light chain variable region having an amino acid sequence as set forth in Table B, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, three, four, five or six CDRs from heavy and light chain variable regions having an amino acid sequence as set forth in Table B), or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the anti-PD-1 antibody molecule comprises at least one, two, or three CDRs and/or hypervariable loops from a heavy chain variable region having an amino acid sequence of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table B, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-PD-1 antibody molecule comprises at least one, two, or three CDRs and/or hypervariable loops from a light chain variable region having an amino acid sequence of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table B, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-PD-1 antibody molecule comprises all six CDRs and/or hypervariable loops described herein, e.g., described in Table B.

In one embodiment, the anti-PD-1 antibody molecule has a variable region that is identical in sequence, or which differs by 1, 2, 3, or 4 amino acids from a variable region described herein (e.g., an FR region disclosed herein).

In one embodiment, the anti-PD-1 antibody molecule is a full antibody or fragment thereof (e.g., a Fab, F(ab')$_2$, Fv, or a single chain Fv fragment (scFv)). In certain embodiments, the anti-PD-1 antibody molecule is a monoclonal antibody or an antibody with single specificity. The anti-PD-1 antibody molecule can also be a humanized, chimeric, camelid, shark, or an in vitro-generated antibody molecule. In one embodiment, the anti-PD-1 antibody molecule thereof is a humanized antibody molecule. The heavy and light chains of the anti-PD-1 antibody molecule can be full-length (e.g., an antibody can include at least one, and preferably two, complete heavy chains, and at least one, and preferably two, complete light chains) or can include an antigen-binding fragment (e.g., a Fab, F(ab')$_2$, Fv, a single chain Fv fragment, a single domain antibody, a diabody (dAb), a bivalent antibody, or bispecific antibody or fragment thereof, a single domain variant thereof, or a camelid antibody).

In yet other embodiments, the anti-PD-1 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1, IgG2 or IgG4). In one embodiment, the heavy chain constant region is human IgG1. In another embodiment, the anti-PD-1 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-PD-1 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 according to EU numbering (e.g., S to P), e.g., as shown in Table D. In certain embodiments, the anti-PD-1 antibody molecules comprises a human IgG4 mutated at position 228 according to EU numbering (e.g., S to P), e.g., as shown in Table D; and a kappa light chain constant region, e.g., as shown in Table D. In still another embodiment, the heavy chain constant region of an IgG1, e.g., a human IgG1, is mutated at one or more of position 297 according to EU numbering (e.g., N to A), position 265 according to EU numbering (e.g., D to A), position 329 according to EU numbering (e.g., P to A), position 234 according to EU numbering (e.g., L to A), or position 235 according to EU numbering (e.g., L to A), e.g., as shown in Table D. In certain embodiments, the anti-PD-1 antibody molecules comprises a human IgG1 mutated at one or more of the aforesaid positions, e.g., as shown in Table D; and a kappa light chain constant region, e.g., as shown in Table D.

In one embodiment, the anti-PD-1 antibody molecule is isolated or recombinant.

In one embodiment, the anti-PD-1 antibody molecule is a humanized antibody molecule.

In one embodiment, the anti-PD-1 antibody molecule has a risk score based on T cell epitope analysis of less than 700, 600, 500, 400 or less.

In one embodiment, the anti-PD-1 antibody molecule is a humanized antibody molecule and has a risk score based on T cell epitope analysis of 300 to 700, 400 to 650, 450 to 600, or a risk score as described herein.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In certain embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In other embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 224.

In embodiments, the aforesaid antibody molecules have a heavy chain variable region comprising at least one framework (FW) region comprising the amino acid sequence of any of SEQ ID NOs: 147, 151, 153, 157, 160, 162, 166, or 169, or an amino acid sequence at least 90% identical thereto, or having no more than two amino acid substitutions, insertions or deletions compared to the amino acid sequence of any of SEQ ID NOs: 147, 151, 153, 157, 160, 162, 166, or 169.

In other embodiments, the aforesaid antibody molecules have a heavy chain variable region comprising at least one framework region comprising the amino acid sequence of any of SEQ ID NOs: 147, 151, 153, 157, 160, 162, 166, or 169.

In yet other embodiments, the aforesaid antibody molecules have a heavy chain variable region comprising at least two, three, or four framework regions comprising the amino acid sequences of any of SEQ ID NOs: 147, 151, 153, 157, 160, 162, 166, or 169.

In other embodiments, the aforesaid antibody molecules comprise a VHFW1 amino acid sequence of SEQ ID NO: 147 or 151, a VHFW2 amino acid sequence of SEQ ID NO: 153, 157, or 160, and a VHFW3 amino acid sequence of SEQ ID NO: 162 or 166, and, optionally, further comprising a VHFW4 amino acid sequence of SEQ ID NO: 169.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208, or an amino acid sequence at least 90% identical thereto, or having no more than two amino acid substitutions, insertions or deletions compared to the amino acid sequence of any of 174, 177, 181, 183, 185, 187, 191, 194, 196, 200, 202, 205, or 208.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208.

In other embodiments, the aforesaid antibody molecules have a light chain variable region comprising at least two, three, or four framework regions comprising the amino acid sequences of any of SEQ ID NOs: 174, 177, 181, 183, 185, 187, 191, 194, 196, 200, 202, 205, or 208.

In other embodiments, the aforesaid antibody molecules comprise a VLFW1 amino acid sequence of SEQ ID NO: 174, 177, 181, 183, or 185, a VLFW2 amino acid sequence of SEQ ID NO: 187, 191, or 194, and a VLFW3 amino acid sequence of SEQ ID NO: 196, 200, 202, or 205, and, optionally, further comprising a VLFW4 amino acid sequence of SEQ ID NO: 208.

In other embodiments, the aforesaid antibodies comprise a heavy chain variable domain comprising an amino acid sequence at least 85% identical to any of SEQ ID NOs: 38, 50, 82, or 86.

In other embodiments, the aforesaid antibody molecules comprise a heavy chain variable domain comprising the amino acid sequence of SEQ ID NO: 38, 50, 82, or 86.

In other embodiments, the aforesaid antibody molecules comprise a light chain variable domain comprising an amino acid sequence at least 85% identical to any of SEQ ID NOs: 42, 46, 54, 58, 62, 66, 70, 74, or 78.

In other embodiments, the aforesaid antibody molecules comprise a light chain variable domain comprising the amino acid sequence of SEQ ID NO: 42, 46, 54, 58, 62, 66, 70, 74, or 78.

In other embodiments, the aforesaid antibody molecules comprise a heavy chain variable domain comprising the amino acid sequence of SEQ ID NO: 38.

In other embodiments, the aforesaid antibody molecules comprise a heavy chain comprising the amino acid sequence of SEQ ID NO: 40.

In other embodiments, the aforesaid antibody molecules comprise a heavy chain comprising the amino acid sequence of SEQ ID NO: 91.

In other embodiments, the aforesaid antibody molecules comprise a heavy chain variable domain comprising the amino acid sequence of SEQ ID NO: 50.

In other embodiments, the aforesaid antibody molecules comprise a heavy chain comprising the amino acid sequence of SEQ ID NO: 52 or SEQ ID NO: 102.

In other embodiments, the aforesaid antibody molecules comprise a heavy chain variable domain comprising the amino acid sequence of SEQ ID NO: 82.

In other embodiments, the aforesaid antibody molecules comprise a heavy chain comprising the amino acid sequence of SEQ ID NO: 84.

In other embodiments, the aforesaid antibody molecules comprise a heavy chain variable domain comprising the amino acid sequence of SEQ ID NO: 86.

In other embodiments, the aforesaid antibody molecules comprise a heavy chain comprising the amino acid sequence of SEQ ID NO: 88.

In other embodiments, the aforesaid antibody molecules comprise a light chain variable domain comprising the amino acid sequence of SEQ ID NO: 42.

In other embodiments, the aforesaid antibody molecules comprise a light chain comprising the amino acid sequence of SEQ ID NO: 44.

In other embodiments, the aforesaid antibody molecules comprise a light chain variable domain comprising the amino acid sequence of SEQ ID NO: 46.

In other embodiments, the aforesaid antibody molecules comprise a light chain comprising the amino acid sequence of SEQ ID NO: 48.

In other embodiments, the aforesaid antibody molecules comprise a light chain variable domain comprising the amino acid sequence of SEQ ID NO: 54.

In other embodiments, the aforesaid antibody molecules comprise a light chain comprising the amino acid sequence of SEQ ID NO: 56.

In other embodiments, the aforesaid antibody molecules comprise a light chain variable domain comprising the amino acid sequence of SEQ ID NO: 58.

In other embodiments, the aforesaid antibody molecules comprise a light chain comprising the amino acid sequence of SEQ ID NO: 60.

In other embodiments, the aforesaid antibody molecules comprise a light chain variable domain comprising the amino acid sequence of SEQ ID NO: 62.

In other embodiments, the aforesaid antibodies comprise a light chain comprising the amino acid sequence of SEQ ID NO: 64.

In other embodiments, the aforesaid antibody molecules comprise a light chain variable domain comprising the amino acid sequence of SEQ ID NO: 66.

In other embodiments, the aforesaid antibody molecules comprise a light chain comprising the amino acid sequence of SEQ ID NO: 68.

In other embodiments, the aforesaid antibody molecules comprise a light chain variable domain comprising the amino acid sequence of SEQ ID NO: 70.

In other embodiments, the aforesaid antibody molecules comprise a light chain comprising the amino acid sequence of SEQ ID NO: 72.

In other embodiments, the aforesaid antibody molecules comprise a light chain variable domain comprising the amino acid sequence of SEQ ID NO: 74.

In other embodiments, the aforesaid antibody molecules comprise a light chain comprising the amino acid sequence of SEQ ID NO: 76.

In other embodiments, the aforesaid antibody molecules comprise a light chain variable domain comprising the amino acid sequence of SEQ ID NO: 78.

In other embodiments, the aforesaid antibody molecules comprise a light chain comprising the amino acid sequence of SEQ ID NO: 80.

In other embodiments, the aforesaid antibody molecules comprise a heavy chain variable domain comprising the amino acid sequence of SEQ ID NO: 38 and a light chain variable domain comprising the amino acid sequence of SEQ ID NO: 42.

In other embodiments, the aforesaid antibody molecules comprise a heavy chain variable domain comprising the amino acid sequence of SEQ ID NO: 38 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 70.

In other embodiments, the aforesaid antibody molecules comprise a heavy chain variable domain comprising the amino acid sequence of SEQ ID NO: 50 and a light chain variable domain comprising the amino acid sequence of SEQ ID NO: 70.

In other embodiments, the aforesaid antibody molecules comprise a heavy chain variable domain comprising the amino acid sequence of SEQ ID NO: 38 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 58.

In other embodiments, the aforesaid antibody molecules comprise a heavy chain variable domain comprising the amino acid sequence of SEQ ID NO: 38 and a light chain variable domain comprising the amino acid sequence of SEQ ID NO: 62.

In other embodiments, the aforesaid antibody molecules comprise a heavy chain variable domain comprising the amino acid sequence of SEQ ID NO: 50 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 74.

In other embodiments, the aforesaid antibody molecules comprise a heavy chain variable domain comprising the amino acid sequence of SEQ ID NO: 38 and a light chain variable domain comprising the amino acid sequence of SEQ ID NO: 78.

In other embodiments, the aforesaid antibody molecules comprise a heavy chain variable domain comprising the amino acid sequence of SEQ ID NO: 82 and a light chain variable domain comprising the amino acid sequence of SEQ ID NO: 70.

In other embodiments, the aforesaid antibody molecules comprise a heavy chain variable domain comprising the amino acid sequence of SEQ ID NO: 82 and a light chain variable domain comprising the amino acid sequence of SEQ ID NO: 66.

In other embodiments, the aforesaid antibody molecules comprise a heavy chain variable domain comprising the amino acid sequence of SEQ ID NO: 86 and a light chain variable domain comprising the amino acid sequence of SEQ ID NO: 66.

In other embodiments, the aforesaid antibody molecules comprise a heavy chain comprising the amino acid sequence of SEQ ID NO: 91 and a light chain comprising the amino acid sequence of SEQ ID NO: 44.

In other embodiments, the aforesaid antibody molecules comprise a heavy chain comprising the amino acid sequence of SEQ ID NO: 91 and a light chain comprising the amino acid sequence of SEQ ID NO: 56.

In other embodiments, the aforesaid antibody molecules comprise a heavy chain comprising the amino acid sequence of SEQ ID NO: 91 and a light chain comprising the amino acid sequence of SEQ ID NO: 68.

In other embodiments, the aforesaid antibody molecules comprise a heavy chain comprising the amino acid sequence of SEQ ID NO: 91 and a light chain comprising the amino acid sequence of SEQ ID NO: 72.

In other embodiments, the aforesaid antibody molecules comprise a heavy chain comprising the amino acid sequence of SEQ ID NO: 102 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 44.

In other embodiments, the aforesaid antibody molecules comprise a heavy chain comprising the amino acid sequence of SEQ ID NO: 40 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 56.

In other embodiments, the aforesaid antibody molecules comprise a heavy chain comprising the amino acid sequence of SEQ ID NO: 40 and a light chain comprising the amino acid sequence of SEQ ID NO: 56.

In other embodiments, the aforesaid antibodies comprise a heavy chain comprising the amino acid sequence of SEQ ID NO: 40 and a light chain comprising the amino acid sequence of SEQ ID NO: 60.

In other embodiments, the aforesaid antibody molecules comprise a heavy chain comprising the amino acid sequence of SEQ ID NO: 40 and a light chain comprising the amino acid sequence of SEQ ID NO: 64.

In other embodiments, the aforesaid antibody molecules comprise a heavy chain comprising the amino acid sequence of SEQ ID NO: 52 and a light chain comprising the amino acid sequence of SEQ ID NO: 68.

In other embodiments, the aforesaid antibody molecules comprise a heavy chain comprising the amino acid sequence of SEQ ID NO: 40 and a light chain comprising the amino acid sequence of SEQ ID NO: 68.

In other embodiments, the aforesaid antibody molecules comprise a heavy chain comprising the amino acid sequence of SEQ ID NO: 52 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 76.

In other embodiments, the aforesaid antibody molecules comprise a heavy chain comprising the amino acid sequence of SEQ ID NO: 40 and a light chain comprising the amino acid sequence of SEQ ID NO: 80.

In other embodiments, the aforesaid antibody molecules comprise a heavy chain comprising the amino acid sequence of SEQ ID NO: 84 and a light chain comprising the amino acid sequence of SEQ ID NO: 72.

In other embodiments, the aforesaid antibodies comprise a heavy chain comprising the amino acid sequence of SEQ ID NO: 84 and a light chain comprising the amino acid sequence of SEQ ID NO: 68.

In other embodiments, the aforesaid antibody molecules comprise a heavy chain comprising the amino acid sequence of SEQ ID NO: 88 and a light chain comprising the amino acid sequence of SEQ ID NO: 68.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 according to EU numbering or position 108 of SEQ ID NO: 212 or 214 and a kappa light chain constant region.

In other embodiments, the aforesaid antibody molecules comprise a human IgG4 heavy chain constant region with a Serine to Proline mutation at position 228 according to EU numbering or position 108 of SEQ ID NO: 212 or 214 and a kappa light chain constant region.

In other embodiments, the aforesaid antibody molecules comprise a human IgG1 heavy chain constant region with an Asparagine to Alanine mutation at position 297 according to EU numbering or position 180 of SEQ ID NO: 216 and a kappa light chain constant region.

In other embodiments, the aforesaid antibody molecules comprise a human IgG1 heavy chain constant region with an Aspartate to Alanine mutation at position 265 according to EU numbering or position 148 of SEQ ID NO: 217, and Proline to Alanine mutation at position 329 according to EU numbering or position 212 of SEQ ID NO: 217 and a kappa light chain constant region.

In other embodiments, the aforesaid antibody molecules comprise a human IgG1 heavy chain constant region with a Leucine to Alanine mutation at position 234 according to EU numbering or position 117 of SEQ ID NO: 218, and Leucine to Alanine mutation at position 235 according to EU numbering or position 118 of SEQ ID NO: 218 and a kappa light chain constant region.

In other embodiments, the aforesaid antibody molecules are capable of binding to human PD-1 with a dissociation constant ($K_D$) of less than about 0.2 nM.

In some embodiments, the aforesaid antibody molecules bind to human PD-1 with a $K_D$ of less than about 0.2 nM, 0.15 nM, 0.1 nM, 0.05 nM, or 0.02 nM, e.g., about 0.13 nM to 0.03 nM, e.g., about 0.077 nM to 0.088 nM, e.g., about 0.083 nM, e.g., as measured by a Biacore method.

In other embodiments, the aforesaid antibody molecules bind to cynomolgus PD-1 with a $K_D$ of less than about 0.2 nM, 0.15 nM, 0.1 nM, 0.05 nM, or 0.02 nM, e.g., about 0.11 nM to 0.08 nM, e.g., about 0.093 nM, e.g., as measured by a Biacore method.

In certain embodiments, the aforesaid antibody molecules bind to both human PD-1 and cynomolgus PD-1 with similar $K_D$, e.g., in the nM range, e.g., as measured by a Biacore method. In some embodiments, the aforesaid antibody molecules bind to a human PD-1-Ig fusion protein with a $K_D$ of less than about 0.1 nM, 0.075 nM, 0.05 nM, 0.025 nM, or 0.01 nM, e.g., about 0.04 nM, e.g., as measured by ELISA.

In some embodiments, the aforesaid antibody molecules bind to Jurkat cells that express human PD-1 (e.g., human PD-1-transfected Jurkat cells) with a $K_D$ of less than about 0.1 nM, 0.075 nM, 0.05 nM, 0.025 nM, or 0.01 nM, e.g., about 0.06 nM, e.g., as measured by FACS analysis.

In some embodiments, the aforesaid antibody molecules bind to cynomolgus T cells with a $K_D$ of less than about 1 nM, 0.75 nM, 0.5 nM, 0.25 nM, or 0.1 nM, e.g., about 0.4 nM, e.g., as measured by FACS analysis.

In some embodiments, the aforesaid antibody molecules bind to cells that express cynomolgus PD-1 (e.g., cells transfected with cynomolgus PD-1) with a $K_D$ of less than about 1 nM, 0.75 nM, 0.5 nM, 0.25 nM, or 0.01 nM, e.g., about 0.6 nM, e.g., as measured by FACS analysis.

In certain embodiments, the aforesaid antibody molecules are not cross-reactive with mouse or rat PD-1. In other embodiments, the aforesaid antibodies are cross-reactive with rhesus PD-1. For example, the cross-reactivity can be measured by a Biacore method or a binding assay using cells that expresses PD-1 (e.g., human PD-1-expressing 300.19 cells). In other embodiments, the aforesaid antibody molecules bind an extracellular Ig-like domain of PD-1.

In other embodiments, the aforesaid antibody molecules are capable of reducing binding of PD-1 to PD-L1, PD-L2, or both, or a cell that expresses PD-L1, PD-L2, or both. In some embodiments, the aforesaid antibody molecules reduce (e.g., block) PD-L1 binding to a cell that expresses PD-1 (e.g., human PD-1-expressing 300.19 cells) with an IC50 of less than about 1.5 nM, 1 nM, 0.8 nM, 0.6 nM, 0.4 nM, 0.2 nM, or 0.1 nM, e.g., between about 0.79 nM and about 1.09 nM, e.g., about 0.94 nM, or about 0.78 nM or less, e.g., about 0.3 nM. In some embodiments, the aforesaid antibodies reduce (e.g., block) PD-L2 binding to a cell that expresses PD-1 (e.g., human PD-1-expressing 300.19 cells) with an IC50 of less than about 2 nM, 1.5 nM, 1 nM, 0.5 nM, or 0.2 nM, e.g., between about 1.05 nM and about 1.55 nM, or about 1.3 nM or less, e.g., about 0.9 nM.

In other embodiments, the aforesaid antibody molecules are capable of enhancing an antigen-specific T cell response.

In embodiments, the antibody molecule is a monospecific antibody molecule or a bispecific antibody molecule. In embodiments, the antibody molecule has a first binding specificity for PD-1 and a second binding specificity for TIM-3, LAG-3, CEACAM (e.g., CEACAM-1, CEACAM-3, and/or CEACAM-5), PD-L1 or PD-L2. In embodiments, the antibody molecule comprises an antigen binding fragment of an antibody, e.g., a half antibody or antigen binding fragment of a half antibody.

In some embodiments, the aforesaid antibody molecules increase the expression of IL-2 from cells activated by Staphylococcal enterotoxin B (SEB) (e.g., at 25 µg/mL) by at least about 2, 3, 4, 5-fold, e.g., about 2 to 3-fold, e.g., about 2 to 2.6-fold, e.g., about 2.3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 µg/mL) by at least about 2, 3, 4, 5-fold, e.g., about 1.2 to 3.4-fold, e.g., about 2.3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 pg/mL) by at least about 2, 3, 4, 5-fold, e.g., about 0.5 to 4.5-fold, e.g., about 2.5-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated with an CMV peptide by at least about 2, 3, 4, 5-fold, e.g., about 2 to 3.6-fold, e.g., about 2.8-fold, compared to the expression of IFN-γ when an isotype control (e.g., IgG4) is used, e.g., as measured in an IFN-γ activity assay.

In some embodiments, the aforesaid antibody molecules increase the proliferation of CD8+ T cells activated with an CMV peptide by at least about 1, 2, 3, 4, 5-fold, e.g., about 1.5-fold, compared to the proliferation of CD8+ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 100 μg/mL and about 500 μg/mL, between about 150 μg/mL and about 450 μg/mL, between about 250 μg/mL and about 350 μg/mL, or between about 200 μg/mL and about 400 μg/mL, e.g., about 292.5 μg/mL, e.g., as measured in monkey.

In certain embodiments, the aforesaid antibody molecules has a $T_{1/2}$ between about 250 hours and about 650 hours, between about 300 hours and about 600 hours, between about 350 hours and about 550 hours, or between about 400 hours and about 500 hours, e.g., about 465.5 hours, e.g., as measured in monkey.

In some embodiments, the aforesaid antibody molecules bind to PD-1 with a Kd slower than $5 \times 10^{-4}$, $1 \times 10^{-4}$, $5 \times 10^{-5}$, or $1 \times 10^{-5}$ s$^{-1}$, e.g., about $2.13 \times 10^{-4}$ s$^{-1}$, e.g., as measured by a Biacore method. In some embodiments, the aforesaid antibody molecules bind to PD-1 with a Ka faster than $1 \times 10^4$, $5 \times 10^4$, $1 \times 10^5$, or $5 \times 10^5$ M$^{-1}$s$^{-1}$, e.g., about $2.78 \times 10^5$ M$^{-1}$s$^{-1}$, e.g., as measured by a Biacore method.

In some embodiments, the aforesaid anti-PD-1 antibody molecules bind to one or more residues within the C strand, CC' loop, C' strand and FG loop of PD-1. The domain structure of PD-1 is described, e.g., in Cheng et al., "Structure and Interactions of the Human Programmed Cell Death 1 Receptor" *J. Biol. Chem.* 2013, 288:11771-11785. As described in Cheng et. al., the C strand comprises residues F43-M50, the CC' loop comprises S51-N54, the C' strand comprises residues Q55-F62, and the FG loop comprises residues L108-I114 (amino acid numbering according to Chang et al. supra). Accordingly, in some embodiments, an anti-PD-1 antibody as described herein binds to at least one residue in one or more of the ranges F43-M50, S51-N54, Q55-F62, and L108-I114 of PD-1. In some embodiments, an anti-PD-1 antibody as described herein binds to at least one residue in two, three, or all four of the ranges F43-M50, S51-N54, Q55-F62, and L108-I114 of PD-1. In some embodiments, the anti-PD-1 antibody binds to a residue in PD-1 that is also part of a binding site for one or both of PD-L1 and PD-L2.

In another aspect, the invention provides an isolated nucleic acid molecule encoding any of the aforesaid antibody molecules, vectors and host cells thereof.

An isolated nucleic acid encoding the antibody heavy chain variable region or light chain variable region, or both, of any the aforesaid antibody molecules is also provided.

In one embodiment, the isolated nucleic acid encodes heavy chain CDRs 1-3, wherein said nucleic acid comprises a nucleotide sequence of SEQ ID NO: 108-112, 223, 122-126, 133-137, or 144-146.

In another embodiment, the isolated nucleic acid encodes light chain CDRs 1-3, wherein said nucleic acid comprises a nucleotide sequence of SEQ ID NO: 113-120, 127-132, or 138-143.

In other embodiments, the aforesaid nucleic acid further comprises a nucleotide sequence encoding a heavy chain variable domain, wherein said nucleotide sequence is at least 85% identical to any of SEQ ID NO: 39, 51, 83, 87, 90, 95, or 101.

In other embodiments, the aforesaid nucleic acid further comprises a nucleotide sequence encoding a heavy chain variable domain, wherein said nucleotide sequence comprises any of SEQ ID NO: 39, 51, 83, 87, 90, 95, or 101.

In other embodiments, the aforesaid nucleic acid further comprises a nucleotide sequence encoding a heavy chain, wherein said nucleotide sequence is at least 85% identical to any of SEQ ID NO: 41, 53, 85, 89, 92, 96, or 103.

In other embodiments, the aforesaid nucleic acid further comprises a nucleotide sequence encoding a heavy chain, wherein said nucleotide sequence comprises any of SEQ ID NO: 41, 53, 85, 89, 92, 96, or 103.

In other embodiments, the aforesaid nucleic acid further comprises a nucleotide sequence encoding a light chain variable domain, wherein said nucleotide sequence is at least 85% identical to any of SEQ ID NO: 45, 49, 57, 61, 65, 69, 73, 77, 81, 94, 98, 100, 105, or 107.

In other embodiments, the aforesaid nucleic acid further comprises a nucleotide sequence encoding a light chain variable domain, wherein said nucleotide sequence comprises any of SEQ ID NO: 45, 49, 57, 61, 65, 69, 73, 77, 81, 94, 98, 100, 105, or 107.

In other embodiments, the aforesaid nucleic acid further comprises a nucleotide sequence encoding a light chain, wherein said nucleotide sequence is at least 85% identical to any of SEQ ID NO: 45, 49, 57, 61, 65, 69, 73, 77, 81, 94, 98, 100, 105 or 107.

In other embodiments, the aforesaid nucleic acid further comprises a nucleotide sequence encoding a light chain, wherein said nucleotide sequence comprises any of SEQ ID NO: 45, 49, 57, 61, 65, 69, 73, 77, 81, 94, 98, 100, 105 or 107.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

In one aspect, the invention features a method of providing an antibody molecule described herein. The method includes: providing a PD-1 antigen (e.g., an antigen comprising at least a portion of a PD-1 epitope); obtaining an antibody molecule that specifically binds to the PD-1 polypeptide; and evaluating if the antibody molecule specifically binds to the PD-1 polypeptide, or evaluating efficacy of the antibody molecule in modulating, e.g., inhibiting, the activity of the PD-1. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the therapeutic agents, e.g., anti-PD-1 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

TABLE B

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | | |
|---|---|---|---|
| BAP049 HC | | | |
| SEQ ID NO: 1 (Kabat) | | HCDR1 | TYWMH |
| SEQ ID NO: 2 (Kabat) | | HCDR2 | NIYPGTGGSNFDEKFKN |
| SEQ ID NO: 3 (Kabat) | | HCDR3 | WTTGTGAY |
| SEQ ID NO: 4 (Chothia) | | HCDR1 | GYTFTTY |
| SEQ ID NO: 5 (Chothia) | | HCDR2 | YPGTGG |
| SEQ ID NO: 3 (Chothia) | | HCDR3 | WTTGTGAY |
| SEQ ID NO: 6 | | VH | QVQLQQPGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTLVTVSA |
| SEQ ID NO: 7 | | DNA VH | CAGGTCCAGCTGCAGCAACCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AAGGGACTCTGGTCACTGTCTCTGCA |
| SEQ ID NO: 8 | | VH | QVQLQQSGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTLVTVSA |
| SEQ ID NO: 9 | | DNA VH | CAGGTCCAGCTGCAGCAGTCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AAGGGACTCTGGTCACTGTCTCTGCA |
| BAP049 LC | | | |
| SEQ ID NO: 10 (Kabat) | | LCDR1 | KSSQSLLDSGNQKNFLT |
| SEQ ID NO: 11 (Kabat) | | LCDR2 | WASTRES |
| SEQ ID NO: 12 (Kabat) | | LCDR3 | QNDYSYPCT |
| SEQ ID NO: 13 (Chothia) | | LCDR1 | SQSLLDSGNQKNF |
| SEQ ID NO: 14 (Chothia) | | LCDR2 | WAS |
| SEQ ID NO: 15 (Chothia) | | LCDR3 | DYSYPC |
| SEQ ID NO: 16 | | VL | DIVMTQSPSSLTVTAGEKVTMSCKSSQSLLDSGN QKNFLTWYQQKPGQPPKLLIFWASTRESGVPDR FTGSGSVTDFTLTISSVQAEDLAVYYCQNDYSYPC TFGGGTKLEIK |
| SEQ ID NO: 17 | | DNA VL | GACATTGTGATGACCCAGTCTCCATCCTCCCTG ACTGTGACAGCAGGAGAGAAGGTCACTATGAG CTGCAAGTCCAGTCAGAGTCTGTTAGACAGTG GAAATCAAAAGAACTTCTTGACCTGGTACCAGC AGAAACCAGGGCAGCCTCCTAAACTGTTGATCT TCTGGGCATCCACTAGGGAATCTGGGGTCCCT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | GATCGCTTCACAGGCAGTGGATCTGTAACAGA<br>TTTCACTCTCACCATCAGCAGTGTGCAGGCTGA<br>AGACCTGGCAGTTTATTACTGTCAGAATGATTA<br>TAGTTATCCGTGCACGTTCGGAGGGGGGACCA<br>AGCTGGAAATAAAA |
|  | BAP049-chi HC |  |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 18 | VH | QVQLQQPGSELVRPGASVKLSCKASGYTFTTYW<br>MHWVRQRPGQGLEWIGNIYPGTGGSNFDEKFK<br>NRTSLTVDTSSTTAYMHLASLTSEDSAVYYCTRW<br>TTGTGAYWGQGTTVTVSS |
| SEQ ID NO: 19 | DNA VH | CAGGTCCAGCTGCAGCAGCCTGGGTCTGAGCT<br>GGTGAGGCCTGGAGCTTCAGTGAAGCTGTCCT<br>GCAAGGCGTCTGGCTACACATTCACCACTTACT<br>GGATGCACTGGGTGAGGCAGAGGCCTGGACA<br>AGGCCTTGAGTGGATTGGAAATATTTATCCTGG<br>TACTGGTGGTTCTAACTTCGATGAGAAGTTCAA<br>AAACAGGACCTCACTGACTGTAGACACATCCTC<br>CACCACAGCCTACATGCACCTCGCCAGCCTGAC<br>ATCTGAGGACTCTGCGGTCTATTACTGTACAAG<br>ATGGACTACTGGGACGGGAGCTTATTGGGGCC<br>AGGGCACCACCGTGACCGTGTCCTCC |
| SEQ ID NO: 20 | HC | QVQLQQPGSELVRPGASVKLSCKASGYTFTTYW<br>MHWVRQRPGQGLEWIGNIYPGTGGSNFDEKFK<br>NRTSLTVDTSSTTAYMHLASLTSEDSAVYYCTRW<br>TTGTGAYWGQGTTVTVSSASTKGPSVFPLAPCSR<br>STSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPS<br>VFLFPPKPKDTLMISRTPEVTCVVVDVSQEDPEV<br>QFNWYVDGVEVHNAKTKPREEQFNSTYRVVSVL<br>TVLHQDWLNGKEYKCKVSNKGLPSSIEKTISKAKG<br>QPREPQVYTLPPSQEEMTKNQVSLTCLVKGFYPS<br>DIAVEWESNGQPENNYKTTPPVLDSDGSFFLYSR<br>LTVDKSRWQEGNVFSCSVMHEALHNHYTQKSLS<br>LSLGK |
| SEQ ID NO: 21 | DNA HC | CAGGTCCAGCTGCAGCAGCCTGGGTCTGAGCT<br>GGTGAGGCCTGGAGCTTCAGTGAAGCTGTCCT<br>GCAAGGCGTCTGGCTACACATTCACCACTTACT<br>GGATGCACTGGGTGAGGCAGAGGCCTGGACA<br>AGGCCTTGAGTGGATTGGAAATATTTATCCTGG<br>TACTGGTGGTTCTAACTTCGATGAGAAGTTCAA<br>AAACAGGACCTCACTGACTGTAGACACATCCTC<br>CACCACAGCCTACATGCACCTCGCCAGCCTGAC<br>ATCTGAGGACTCTGCGGTCTATTACTGTACAAG<br>ATGGACTACTGGGACGGGAGCTTATTGGGGCC<br>AGGGCACCACCGTGACCGTGTCCTCCGCTTCCA<br>CCAAGGGCCCATCCGTCTTCCCCCTGGCGCCCT<br>GCTCCAGGAGCACCTCCGAGAGCACAGCCGCC<br>CTGGGCTGCCTGGTCAAGGACTACTTCCCCGAA<br>CCGGTGACGGTGTCGTGGAACTCAGGCGCCCT<br>GACCAGCGGCGTGCACACCTTCCCGGCTGTCCT<br>ACAGTCCTCAGGACTCTACTCCCTCAGCAGCGT<br>GGTGACCGTGCCCTCCAGCAGCTTGGGCACGA<br>AGACCTACACCTGCAACGTAGATCACAAGCCCA<br>GCAACACCAAGGTGGACAAGAGAGTTGAGTCC<br>AAATATGGTCCCCCATGCCCACCGTGCCCAGCA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | CCTGAGTTCCTGGGGGGACCATCAGTCTTCCTG TTCCCCCCAAAACCCAAGGACACTCTCATGATC TCCCGGACCCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCAGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |
| SEQ ID NO: 22 | VH | QVQLQQSGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTTVTVSS |
| SEQ ID NO: 23 | DNA VH | CAGGTCCAGCTGCAGCAGTCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AGGGCACCACCGTGACCGTGTCCTCC |
| SEQ ID NO: 30 | HC | QVQLQQSGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTTVTVSSASTKGPSVFPLAPCSR STSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPS VFLFPPKPKDTLMISRTPEVTCVVVDVSQEDPEV QFNWYVDGVEVHNAKTKPREEQFNSTYRVVSVL TVLHQDWLNGKEYKCKVSNKGLPSSIEKTISKAKG QPREPQVYTLPPSQEEMTKNQVSLTCLVKGFYPS DIAVEWESNGQPENNYKTTPPVLDSDGSFFLYSR LTVDKSRWQEGNVFSCSVMHEALHNHYTQKSLS LSLGK |
| SEQ ID NO: 31 | DNA HC | CAGGTCCAGCTGCAGCAGTCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
GCAACACCAAGGTGGACAAGAGAGTTGAGTCC
AAATATGGTCCCCCATGCCCACCGTGCCCAGCA
CCTGAGTTCCTGGGGGGACCATCAGTCTTCCTG
TTCCCCCCAAAACCCAAGGACACTCTCATGATC
TCCCGGACCCCTGAGGTCACGTGCGTGGTGGT
GGACGTGAGCCAGGAAGACCCCGAGGTCCAGT
TCAACTGGTACGTGGATGGCGTGGAGGTGCAT
AATGCCAAGACAAAGCCGCGGGAGGAGCAGTT
CAACAGCACGTACCGTGTGGTCAGCGTCCTCAC
CGTCCTGCACCAGGACTGGCTGAACGGCAAGG
AGTACAAGTGCAAGGTGTCCAACAAAGGCCTC
CCGTCCTCCATCGAGAAAACCATCTCCAAAGCC
AAAGGGCAGCCCCGAGAGCCACAGGTGTACAC
CCTGCCCCCATCCCAGGAGGAGATGACCAAGA
ACCAGGTCAGCCTGACCTGCCTGGTCAAAGGC
TTCTACCCCAGCGACATCGCCGTGGAGTGGGA
GAGCAATGGGCAGCCGGAGAACAACTACAAG
ACCACGCCTCCCGTGCTGGACTCCGACGGCTCC
TTCTTCCTCTACAGCAGGCTAACCGTGGACAAG
AGCAGGTGGCAGGAGGGGAATGTCTTCTCATG
CTCCGTGATGCATGAGGCTCTGCACAACCACTA
CACACAGAAGAGCCTCTCCCTGTCTCTGGGTAA
A
```

BAP049-chi LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 12 (Kabat) | LCDR3 | QNDYSYPCT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPC |
| SEQ ID NO: 24 | VL | DIVMTQSPSSLTVTAGEKVTMSCKSSQSLLDSGN QKNFLTWYQQKPGQPPKLLIFWASTRESGVPDR FTGSGSVTDFTLTISSVQAEDLAVYYCQNDYSYPC TFGQGTKVEIK |
| SEQ ID NO: 25 | DNA VL | GACATTGTGATGACCCAGTCTCCATCCTCCCTG ACTGTGACAGCAGGAGAGAAGGTCACTATGAG CTGCAAGTCCAGTCAGAGTCTGTTAGACAGTG GAAATCAAAAGAACTTCTTGACCTGGTACCAGC AGAAACCAGGGCAGCCTCCTAAACTGTTGATCT TCTGGGCATCCACTAGGGAATCTGGGGTCCCT GATCGCTTCACAGGCAGTGGATCTGTAACAGA TTTCACTCTCACCATCAGCAGTGTGCAGGCTGA AGACCTGGCAGTTTATTACTGTCAGAATGATTA TAGTTATCCGTGCACGTTCGGCCAAGGGACCA AGGTGGAAATCAAA |
| SEQ ID NO: 26 | LC | DIVMTQSPSSLTVTAGEKVTMSCKSSQSLLDSGN QKNFLTWYQQKPGQPPKLLIFWASTRESGVPDR FTGSGSVTDFTLTISSVQAEDLAVYYCQNDYSYPC TFGQGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVTHQ GLSSPVTKSFNRGEC |
| SEQ ID NO: 27 | DNA LC | GACATTGTGATGACCCAGTCTCCATCCTCCCTG ACTGTGACAGCAGGAGAGAAGGTCACTATGAG CTGCAAGTCCAGTCAGAGTCTGTTAGACAGTG GAAATCAAAAGAACTTCTTGACCTGGTACCAGC AGAAACCAGGGCAGCCTCCTAAACTGTTGATCT TCTGGGCATCCACTAGGGAATCTGGGGTCCCT GATCGCTTCACAGGCAGTGGATCTGTAACAGA TTTCACTCTCACCATCAGCAGTGTGCAGGCTGA AGACCTGGCAGTTTATTACTGTCAGAATGATTA TAGTTATCCGTGCACGTTCGGCCAAGGGACCA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  | AGGTGGAAATCAAACGTACGGTGGCTGCACCA TCTGTCTTCATCTTCCCGCCATCTGATGAGCAGT TGAAATCTGGAACTGCCTCTGTTGTGTGCCTGC TGAATAACTTCTATCCCAGAGAGGCCAAAGTAC AGTGGAAGGTGGATAACGCCCTCCAATCGGGT AACTCCCAGGAGAGTGTCACAGAGCAGGACAG CAAGGACAGCACCTACAGCCTCAGCAGCACCCT GACGCTGAGCAAAGCAGACTACGAGAAACACA AAGTCTACGCCTGCGAAGTCACCCATCAGGGC CTGAGCTCGCCCGTCACAAAGAGCTTCAACAG GGGAGAGTGT |
| --- | --- | --- |
|  | BAP049-chi-Y HC |  |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 18 | VH | QVQLQQPGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTTVTVSS |
| SEQ ID NO: 19 | DNA VH | CAGGTCCAGCTGCAGCAGCCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AGGGCACCACCGTGACCGTGTCCTCC |
| SEQ ID NO: 20 | HC | QVQLQQPGSELVRPGASVKLSCKASGYTFTTYW MHWVRQRPGQGLEWIGNIYPGTGGSNFDEKFK NRTSLTVDTSSTTAYMHLASLTSEDSAVYYCTRW TTGTGAYWGQGTTVTVSSASTKGPSVFPLAPCSR STSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPS VFLFPPKPKDTLMISRTPEVTCVVVDVSQEDPEV QFNWYVDGVEVHNAKTKPREEQFNSTYRVVSVL TVLHQDWLNGKEYKCKVSNKGLPSSIEKTISKAKG QPREPQVYTLPPSQEEMTKNQVSLTCLVKGFYPS DIAVEWESNGQPENNYKTTPPVLDSDGSFFLYSR LTVDKSRWQEGNVFSCSVMHEALHNHYTQKSLS LSLGK |
| SEQ ID NO: 21 | DNA HC | CAGGTCCAGCTGCAGCAGCCTGGGTCTGAGCT GGTGAGGCCTGGAGCTTCAGTGAAGCTGTCCT GCAAGGCGTCTGGCTACACATTCACCACTTACT GGATGCACTGGGTGAGGCAGAGGCCTGGACA AGGCCTTGAGTGGATTGGAAATATTTATCCTGG TACTGGTGGTTCTAACTTCGATGAGAAGTTCAA AAACAGGACCTCACTGACTGTAGACACATCCTC CACCACAGCCTACATGCACCTCGCCAGCCTGAC ATCTGAGGACTCTGCGGTCTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GACCAGCGGCGTGCACACCTTCCCGGCTGTCCT<br>ACAGTCCTCAGGACTCTACTCCCTCAGCAGCGT<br>GGTGACCGTGCCCTCCAGCAGCTTGGGCACGA<br>AGACCTACACCTGCAACGTAGATCACAAGCCCA<br>GCAACACCAAGGTGGACAAGAGAGTTGAGTCC<br>AAATATGGTCCCCCATGCCCACCGTGCCCAGCA<br>CCTGAGTTCCTGGGGGGACCATCAGTCTTCCTG<br>TTCCCCCCAAAACCCAAGGACACTCTCATGATC<br>TCCCGGACCCCTGAGGTCACGTGCGTGGTGGT<br>GGACGTGAGCCAGGAAGACCCCGAGGTCCAGT<br>TCAACTGGTACGTGGATGGCGTGGAGGTGCAT<br>AATGCCAAGACAAAGCCGCGGGAGGAGCAGTT<br>CAACAGCACGTACCGTGTGGTCAGCGTCCTCAC<br>CGTCCTGCACCAGGACTGGCTGAACGGCAAGG<br>AGTACAAGTGCAAGGTGTCCAACAAAGGCCTC<br>CCGTCCTCCATCGAGAAAACCATCTCCAAAGCC<br>AAAGGGCAGCCCCGAGAGCCACAGGTGTACAC<br>CCTGCCCCCATCCCAGGAGGAGATGACCAAGA<br>ACCAGGTCAGCCTGACCTGCCTGGTCAAAGGC<br>TTCTACCCCAGCGACATCGCCGTGGAGTGGGA<br>GAGCAATGGGCAGCCGGAGAACAACTACAAG<br>ACCACGCCTCCCGTGCTGGACTCCGACGGCTCC<br>TTCTTCCTCTACAGCAGGCTAACCGTGGACAAG<br>AGCAGGTGGCAGGAGGGGAATGTCTTCTCATG<br>CTCCGTGATGCATGAGGCTCTGCACAACCACTA<br>CACACAGAAGAGCCTCTCCCTGTCTCTGGGTAA<br>A |
| SEQ ID NO: 22 | VH | QVQLQQSGSELVRPGASVKLSCKASGYTFTTYW<br>MHWVRQRPGQGLEWIGNIYPGTGGSNFDEKFK<br>NRTSLTVDTSSTTAYMHLASLTSEDSAVYYCTRW<br>TTGTGAYWGQGTTVTVSS |
| SEQ ID NO: 23 | DNA VH | CAGGTCCAGCTGCAGCAGTCTGGGTCTGAGCT<br>GGTGAGGCCTGGAGCTTCAGTGAAGCTGTCCT<br>GCAAGGCGTCTGGCTACACATTCACCACTTACT<br>GGATGCACTGGGTGAGGCAGAGGCCTGGACA<br>AGGCCTTGAGTGGATTGGAAATATTTATCCTGG<br>TACTGGTGGTTCTAACTTCGATGAGAAGTTCAA<br>AAACAGGACCTCACTGACTGTAGACACATCCTC<br>CACCACAGCCTACATGCACCTCGCCAGCCTGAC<br>ATCTGAGGACTCTGCGGTCTATTACTGTACAAG<br>ATGGACTACTGGGACGGGAGCTTATTGGGGCC<br>AGGGCACCACCGTGACCGTGTCCTCC |
| SEQ ID NO: 30 | HC | QVQLQQSGSELVRPGASVKLSCKASGYTFTTYW<br>MHWVRQRPGQGLEWIGNIYPGTGGSNFDEKFK<br>NRTSLTVDTSSTTAYMHLASLTSEDSAVYYCTRW<br>TTGTGAYWGQGTTVTVSSASTKGPSVFPLAPCSR<br>STSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPS<br>VFLFPPKPKDTLMISRTPEVTCVVVDVSQEDPEV<br>QFNWYVDGVEVHNAKTKPREEQFNSTYRVVSVL<br>TVLHQDWLNGKEYKCKVSNKGLPSSIEKTISKAKG<br>QPREPQVYTLPPSQEEMTKNQVSLTCLVKGFYPS<br>DIAVEWESNGQPENNYKTTPPVLDSDGSFFLYSR<br>LTVDKSRWQEGNVFSCSVMHEALHNHYTQKSLS<br>LSLGK |
| SEQ ID NO: 31 | DNA HC | CAGGTCCAGCTGCAGCAGTCTGGGTCTGAGCT<br>GGTGAGGCCTGGAGCTTCAGTGAAGCTGTCCT<br>GCAAGGCGTCTGGCTACACATTCACCACTTACT<br>GGATGCACTGGGTGAGGCAGAGGCCTGGACA<br>AGGCCTTGAGTGGATTGGAAATATTTATCCTGG<br>TACTGGTGGTTCTAACTTCGATGAGAAGTTCAA<br>AAACAGGACCTCACTGACTGTAGACACATCCTC<br>CACCACAGCCTACATGCACCTCGCCAGCCTGAC<br>ATCTGAGGACTCTGCGGTCTATTACTGTACAAG<br>ATGGACTACTGGGACGGGAGCTTATTGGGGCC<br>AGGGCACCACCGTGACCGTGTCCTCCGCTTCCA<br>CCAAGGGCCCATCCGTCTTCCCCCTGGCGCCCT<br>GCTCCAGGAGCACCTCCGAGAGCACAGCCGCC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | CTGGGCTGCCTGGTCAAGGACTACTTCCCCGAA<br>CCGGTGACGGTGTCGTGGAACTCAGGCGCCCT<br>GACCAGCGGCGTGCACACCTTCCCGGCTGTCCT<br>ACAGTCCTCAGGACTCTACTCCCTCAGCAGCGT<br>GGTGACCGTGCCCTCCAGCAGCTTGGGCACGA<br>AGACCTACACCTGCAACGTAGATCACAAGCCCA<br>GCAACACCAAGGTGGACAAGAGAGTTGAGTCC<br>AAATATGGTCCCCCATGCCCACCGTGCCCAGCA<br>CCTGAGTTCCTGGGGGGACCATCAGTCTTCCTG<br>TTCCCCCCAAAACCCAAGGACACTCTCATGATC<br>TCCCGGACCCCTGAGGTCACGTGCGTGGTGGT<br>GGACGTGAGCCAGGAAGACCCCGAGGTCCAGT<br>TCAACTGGTACGTGGATGGCGTGGAGGTGCAT<br>AATGCCAAGACAAAGCCGCGGGAGGAGCAGTT<br>CAACAGCACGTACCGTGTGGTCAGCGTCCTCAC<br>CGTCCTGCACCAGGACTGGCTGAACGGCAAGG<br>AGTACAAGTGCAAGGTGTCCAACAAAGGCCTC<br>CCGTCCTCCATCGAGAAAACCATCTCCAAAGCC<br>AAAGGGCAGCCCCGAGAGCCACAGGTGTACAC<br>CCTGCCCCCATCCCAGGAGGAGATGACCAAGA<br>ACCAGGTCAGCCTGACCTGCCTGGTCAAAGGC<br>TTCTACCCCAGCGACATCGCCGTGGAGTGGGA<br>GAGCAATGGGCAGCCGGAGAACAACTACAAG<br>ACCACGCCTCCCGTGCTGGACTCCGACGGCTCC<br>TTCTTCCTCTACAGCAGGCTAACCGTGGACAAG<br>AGCAGGTGGCAGGAGGGGAATGTCTTCTCATG<br>CTCCGTGATGCATGAGGCTCTGCACAACCACTA<br>CACACAGAAGAGCCTCTCCCTGTCTCTGGGTAA<br>A |

BAP049-chi-Y LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 34 | VL | DIVMTQSPSSLTVTAGEKVTMSCKSSQSLLDSGN<br>QKNFLTWYQQKPGQPPKLLIFWASTRESGVPDR<br>FTGSGSVTDFTLTISSVQAEDLAVYYCQNDYSYPY<br>TFGQGTKVEIK |
| SEQ ID NO: 35 | DNA VL | GACATTGTGATGACCCAGTCTCCATCCTCCCTG<br>ACTGTGACAGCAGGAGAGAAGGTCACTATGAG<br>CTGCAAGTCCAGTCAGAGTCTGTTAGACAGTG<br>GAAATCAAAAGAACTTCTTGACCTGGTACCAGC<br>AGAAACCAGGGCAGCCTCCTAAACTGTTGATCT<br>TCTGGGCATCCACTAGGGAATCTGGGGTCCCT<br>GATCGCTTCACAGGCAGTGGATCTGTAACAGA<br>TTTCACTCTCACCATCAGCAGTGTGCAGGCTGA<br>AGACCTGGCAGTTTATTACTGTCAGAATGATTA<br>TAGTTATCCGTACACGTTCGGCCAAGGGACCAA<br>GGTGGAAATCAAA |
| SEQ ID NO: 36 | LC | DIVMTQSPSSLTVTAGEKVTMSCKSSQSLLDSGN<br>QKNFLTWYQQKPGQPPKLLIFWASTRESGVPDR<br>FTGSGSVTDFTLTISSVQAEDLAVYYCQNDYSYPY<br>TFGQGTKVEIKRTVAAPSVFIFPPSDEQLKSGTAS<br>VVCLLNNFYPREAKVQWKVDNALQSGNSQESVT<br>EQDSKDSTYSLSSTLTLSKADYEKHKVYACEVTHQ<br>GLSSPVTKSFNRGEC |
| SEQ ID NO: 37 | DNA LC | GACATTGTGATGACCCAGTCTCCATCCTCCCTG<br>ACTGTGACAGCAGGAGAGAAGGTCACTATGAG<br>CTGCAAGTCCAGTCAGAGTCTGTTAGACAGTG<br>GAAATCAAAAGAACTTCTTGACCTGGTACCAGC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  | AGAAACCAGGGCAGCCTCCTAAACTGTTGATCT<br>TCTGGGCATCCACTAGGGAATCTGGGGTCCCT<br>GATCGCTTCACAGGCAGTGGATCTGTAACAGA<br>TTTCACTCTCACCATCAGCAGTGTGCAGGCTGA<br>AGACCTGGCAGTTTATTACTGTCAGAATGATTA<br>TAGTTATCCGTACACGTTCGGCCAAGGGACCAA<br>GGTGGAAATCAAACGTACGGTGGCTGCACCAT<br>CTGTCTTCATCTTCCCGCCATCTGATGAGCAGTT<br>GAAATCTGGAACTGCCTCTGTTGTGTGCCTGCT<br>GAATAACTTCTATCCCAGAGAGGCCAAAGTACA<br>GTGGAAGGTGGATAACGCCCTCCAATCGGGTA<br>ACTCCCAGGAGAGTGTCACAGAGCAGGACAGC<br>AAGGACAGCACCTACAGCCTCAGCAGCACCCT<br>GACGCTGAGCAAAGCAGACTACGAGAAACACA<br>AAGTCTACGCCTGCGAAGTCACCCATCAGGGC<br>CTGAGCTCGCCCGTCACAAAGAGCTTCAACAG<br>GGGAGAGTGT |
|---|---|---|
|  | BAP049-hum01 HC |  |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM<br>HWVRQATGQGLEWMGNIYPGTGGSNFDEKFK<br>NRVTITADKSTSTAYMELSSLRSEDTAVYYCTRWT<br>TGTGAYWGQGTTVTVSS |
| SEQ ID NO: 39 | DNA VH | GAAGTGCAGCTGGTGCAGTCTGGAGCAGAGGT<br>GAAAAAGCCCGGGGAGTCTCTGAGGATCTCCT<br>GTAAGGGTTCTGGCTACACATTCACCACTTACT<br>GGATGCACTGGGTGCGACAGGCCACTGGACAA<br>GGGCTTGAGTGGATGGGTAATATTTATCCTGGT<br>ACTGGTGGTTCTAACTTCGATGAGAAGTTCAAG<br>AACAGAGTCACGATTACCGCGGACAAATCCAC<br>GAGCACAGCCTACATGGAGCTGAGCAGCCTGA<br>GATCTGAGGACACGGCCGTGTATTACTGTACA<br>AGATGGACTACTGGGACGGGAGCTTATTGGGG<br>CCAGGGCACCACCGTGACCGTGTCCTCC |
| SEQ ID NO: 40 | HC | EVQLVQSGAEVKKPGESLRISCKGSGYTFTTYWM<br>HWVRQATGQGLEWMGNIYPGTGGSNFDEKFK<br>NRVTITADKSTSTAYMELSSLRSEDTAVYYCTRWT<br>TGTGAYWGQGTTVTVSSASTKGPSVFPLAPCSRS<br>TSESTAALGCLVKDYFPEPVTVSWNSGALTSGVH<br>TFPAVLQSSGLYSLSSVVTVPSSSLGTKTYTCNVD<br>HKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTV<br>LHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLT<br>VDKSRWQEGNVFSCSVMHEALHNHYTQKSLSLS<br>LGK |
| SEQ ID NO: 41 | DNA HC | GAAGTGCAGCTGGTGCAGTCTGGAGCAGAGGT<br>GAAAAAGCCCGGGGAGTCTCTGAGGATCTCCT<br>GTAAGGGTTCTGGCTACACATTCACCACTTACT<br>GGATGCACTGGGTGCGACAGGCCACTGGACAA<br>GGGCTTGAGTGGATGGGTAATATTTATCCTGGT<br>ACTGGTGGTTCTAACTTCGATGAGAAGTTCAAG<br>AACAGAGTCACGATTACCGCGGACAAATCCAC<br>GAGCACAGCCTACATGGAGCTGAGCAGCCTGA<br>GATCTGAGGACACGGCCGTGTATTACTGTACA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
AGATGGACTACTGGGACGGGAGCTTATTGGGG
CCAGGGCACCACCGTGACCGTGTCCTCCGCTTC
CACCAAGGGCCCATCCGTCTTCCCCCTGGCGCC
CTGCTCCAGGAGCACCTCCGAGAGCACAGCCG
CCCTGGGCTGCCTGGTCAAGGACTACTTCCCCG
AACCGGTGACGGTGTCGTGGAACTCAGGCGCC
CTGACCAGCGGCGTGCACACCTTCCCGGCTGTC
CTACAGTCCTCAGGACTCTACTCCCTCAGCAGC
GTGGTGACCGTGCCCTCCAGCAGCTTGGGCAC
GAAGACCTACACCTGCAACGTAGATCACAAGC
CCAGCAACACCAAGGTGGACAAGAGAGTTGAG
TCCAAATATGGTCCCCCATGCCCACCGTGCCCA
GCACCTGAGTTCCTGGGGGGACCATCAGTCTTC
CTGTTCCCCCCAAAACCCAAGGACACTCTCATG
ATCTCCCGGACCCCTGAGGTCACGTGCGTGGT
GGTGGACGTGAGCCAGGAAGACCCCGAGGTC
CAGTTCAACTGGTACGTGGATGGCGTGGAGGT
GCATAATGCCAAGACAAAGCCGCGGGAGGAG
CAGTTCAACAGCACGTACCGTGTGGTCAGCGTC
CTCACCGTCCTGCACCAGGACTGGCTGAACGG
CAAGGAGTACAAGTGCAAGGTGTCCAACAAAG
GCCTCCCGTCCTCCATCGAGAAAACCATCTCCA
AAGCCAAAGGGCAGCCCCGAGAGCCACAGGT
GTACACCCTGCCCCCATCCCAGGAGGAGATGA
CCAAGAACCAGGTCAGCCTGACCTGCCTGGTC
AAAGGCTTCTACCCCAGCGACATCGCCGTGGA
GTGGGAGAGCAATGGGCAGCCGGAGAACAAC
TACAAGACCACGCCTCCCGTGCTGGACTCCGAC
GGCTCCTTCTTCCTCTACAGCAGGCTAACCGTG
GACAAGAGCAGGTGGCAGGAGGGGAATGTCT
TCTCATGCTCCGTGATGCATGAGGCTCTGCACA
ACCACTACACAGAAGAGCCTCTCCCTGTCTC
TGGGTAAA
```

BAP049-hum01 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 42 | VL | EIVLTQSPATLSLSPGERATLSCKSSQSLLDSGNQK NFLTWYQQKPGQAPRLLIYWASTRESGVPSRFSG SGSGTEFTLTISSLQPDDFATYYCQNDYSYPYTFG QGTKVEIK |
| SEQ ID NO: 43 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCATC AAGGTTCAGCGGCAGTGGATCTGGGACAGAAT TCACTCTCACCATCAGCAGCCTGCAGCCTGATG ATTTTGCAACTTATTACTGTCAGAATGATTATAG TTATCCGTACACGTTCGGCCAAGGGACCAAGG TGGAAATCAAA |
| SEQ ID NO: 44 | LC | EIVLTQSPATLSLSPGERATLSCKSSQSLLDSGNQK NFLTWYQQKPGQAPRLLIYWASTRESGVPSRFSG SGSGTEFTLTISSLQPDDFATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 45 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGG<br>AAATCAAAAGAACTTCTTGACCTGGTACCAGCA<br>GAAACCTGGCCAGGCTCCCAGGCTCCTCATCTA<br>TTGGGCATCCACTAGGGAATCTGGGGTCCCATC<br>AAGGTTCAGCGGCAGTGGATCTGGGACAGAAT<br>TCACTCTCACCATCAGCAGCCTGCAGCCTGATG<br>ATTTTGCAACTTATTACTGTCAGAATGATTATAG<br>TTATCCGTACACGTTCGGCCAAGGGACCAAGG<br>TGGAAATCAAACGTACGGTGGCTGCACCATCT<br>GTCTTCATCTTCCCGCCATCTGATGAGCAGTTG<br>AAATCTGGAACTGCCTCTGTTGTGTGCCTGCTG<br>AATAACTTCTATCCCAGAGAGGCCAAAGTACAG<br>TGGAAGGTGGATAACGCCCTCCAATCGGGTAA<br>CTCCCAGGAGAGTGTCACAGAGCAGGACAGCA<br>AGGACAGCACCTACAGCCTCAGCAGCACCCTG<br>ACGCTGAGCAAAGCAGACTACGAGAAACACAA<br>AGTCTACGCCTGCGAAGTCACCCATCAGGGCCT<br>GAGCTCGCCCGTCACAAAGAGCTTCAACAGGG<br>GAGAGTGT |

BAP049-hum02 HC

| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM<br>HWVRQATGQGLEWMGNIYPGTGGSNFDEKFK<br>NRVTITADKSTSTAYMELSSLRSEDTAVYYCTRWT<br>TGTGAYWGQGTTVTVSS |
| SEQ ID NO: 39 | DNA VH | GAAGTGCAGCTGGTGCAGTCTGGAGCAGAGGT<br>GAAAAAGCCCGGGGAGTCTCTGAGGATCTCCT<br>GTAAGGGTTCTGGCTACACATTCACCACTTACT<br>GGATGCACTGGGTGCGACAGGCCACTGGACAA<br>GGGCTTGAGTGGATGGGTAATATTTATCCTGGT<br>ACTGGTGGTTCTAACTTCGATGAGAAGTTCAAG<br>AACAGAGTCACGATTACCGCGGACAAATCCAC<br>GAGCACAGCCTACATGGAGCTGAGCAGCCTGA<br>GATCTGAGGACACGGCCGTGTATTACTGTACA<br>AGATGGACTACTGGGACGGGAGCTTATTGGGG<br>CCAGGGCACCACCGTGACCGTGTCCTCC |
| SEQ ID NO: 40 | HC | EVQLVQSGAEVKKPGESLRISCKGSGYTFTTYWM<br>HWVRQATGQGLEWMGNIYPGTGGSNFDEKFK<br>NRVTITADKSTSTAYMELSSLRSEDTAVYYCTRWT<br>TGTGAYWGQGTTVTVSSASTKGPSVFPLAPCSRS<br>TSESTAALGCLVKDYFPEPVTVSWNSGALTSGVH<br>TFPAVLQSSGLYSLSSVVTVPSSSLGTKTYTCNVD<br>HKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTV<br>LHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLT<br>VDKSRWQEGNVFSCSVMHEALHNHYTQKSLSLS<br>LGK |
| SEQ ID NO: 41 | DNA HC | GAAGTGCAGCTGGTGCAGTCTGGAGCAGAGGT<br>GAAAAAGCCCGGGGAGTCTCTGAGGATCTCCT<br>GTAAGGGTTCTGGCTACACATTCACCACTTACT<br>GGATGCACTGGGTGCGACAGGCCACTGGACAA<br>GGGCTTGAGTGGATGGGTAATATTTATCCTGGT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
ACTGGTGGTTCTAACTTCGATGAGAAGTTCAAG
AACAGAGTCACGATTACCGCGGACAAATCCAC
GAGCACAGCCTACATGGAGCTGAGCAGCCTGA
GATCTGAGGACACGGCCGTGTATTACTGTACA
AGATGGACTACTGGGACGGGAGCTTATTGGGG
CCAGGGCACCACCGTGACCGTGTCCTCCGCTTC
CACCAAGGGCCCATCCGTCTTCCCCCTGGCGCC
CTGCTCCAGGAGCACCTCCGAGAGCACAGCCG
CCCTGGGCTGCCTGGTCAAGGACTACTTCCCCG
AACCGGTGACGGTGTCGTGGAACTCAGGCGCC
CTGACCAGCGGCGTGCACACCTTCCCGGCTGTC
CTACAGTCCTCAGGACTCTACTCCCTCAGCAGC
GTGGTGACCGTGCCCTCCAGCAGCTTGGGCAC
GAAGACCTACACCTGCAACGTAGATCACAAGC
CCAGCAACACCAAGGTGGACAAGAGAGTTGAG
TCCAAATATGGTCCCCCATGCCCACCGTGCCCA
GCACCTGAGTTCCTGGGGGGACCATCAGTCTTC
CTGTTCCCCCCAAAACCCAAGGACACTCTCATG
ATCTCCCGGACCCCTGAGGTCACGTGCGTGGT
GGTGGACGTGAGCCAGGAAGACCCCGAGGTC
CAGTTCAACTGGTACGTGGATGGCGTGGAGGT
GCATAATGCCAAGACAAAGCCGCGGGAGGAG
CAGTTCAACAGCACGTACCGTGTGGTCAGCGTC
CTCACCGTCCTGCACCAGGACTGGCTGAACGG
CAAGGAGTACAAGTGCAAGGTGTCCAACAAAG
GCCTCCCGTCCTCCATCGAGAAAACCATCTCCA
AAGCCAAAGGGCAGCCCCGAGAGCCACAGGT
GTACACCCTGCCCCCATCCCAGGAGGAGATGA
CCAAGAACCAGGTCAGCCTGACCTGCCTGGTC
AAAGGCTTCTACCCCAGCGACATCGCCGTGGA
GTGGGAGAGCAATGGGCAGCCGGAGAACAAC
TACAAGACCACGCCTCCCGTGCTGGACTCCGAC
GGCTCCTTCTTCCTCTACAGCAGGCTAACCGTG
GACAAGAGCAGGTGGCAGGAGGGGAATGTCT
TCTCATGCTCCGTGATGCATGAGGCTCTGCACA
ACCACTACACAGAAGAGCCTCTCCCTGTCTC
TGGGTAAA
```

BAP049-hum02 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 46 | VL | DIQMTQSPSSLSASVGDRVTITCKSSQSLLDSGNQ KNFLTWYQQKPGQAPRLLIYWASTRESGIPPRFS GSGYGTDFTLTINNIESEDAAYYFCQNDYSYPYTF GQGTKVEIK |
| SEQ ID NO: 47 | DNA VL | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGATCCCACC TCGATTCAGTGGCAGCGGGTATGGAACAGATT TTACCCTCACAATTAATAACATAGAATCTGAGG ATGCTGCATATTACTTCTGTCAGAATGATTATA GTTATCCGTACACGTTCGGCCAAGGGACCAAG GTGGAAATCAAA |
| SEQ ID NO: 48 | LC | DIQMTQSPSSLSASVGDRVTITCKSSQSLLDSGNQ KNFLTWYQQKPGQAPRLLIYWASTRESGIPPRFS GSGYGTDFTLTINNIESEDAAYYFCQNDYSYPYTF GQGTKVEIKRTVAAPSVFIFPPSDEQLKSGTASVV |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | CLLNNFYPREAKVQWKVDNALQSGNSQESVTEQ DSKDSTYSLSSTLTLSKADYEKHKVYACEVTHQGL SSPVTKSFNRGEC |
| SEQ ID NO: 49 | DNA LC | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGATCCCACC TCGATTCAGTGGCAGCGGGTATGGAACAGATT TTACCCTCACAATTAATAACATAGAATCTGAGG ATGCTGCATATTACTTCTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum03 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSS |
| SEQ ID NO: 51 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCC |
| SEQ ID NO: 52 | HC | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSSASTKGPSVFPLAPCSRST SESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFN WYVDGVEVHNAKTKPREEQFNSTYRVVSVLTVL HQDWLNGKEYKCKVSNKGLPSSIEKTISKAKGQP REPQVYTLPPSQEEMTKNQVSLTCLVKGFYPSDIA VEWESNGQPENNYKTTPPVLDSDGSFFLYSRLTV DKSRWQEGNVFSCSVMHEALHNHYTQKSLSLSL GK |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 53 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG TTCCCCCCAAAACCCAAGGACACTCTCATGATC TCCCGGACCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCAGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |

BAP049-hum03 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 46 | VL | DIQMTQSPSSLSASVGDRVTITCKSSQSLLDSGNQ KNFLTWYQQKPGQAPRLLIYWASTRESGIPPRFS GSGYGTDFTLTINNIESEDAAYYFCQNDYSYPYTF GQGTKVEIK |
| SEQ ID NO: 47 | DNA VL | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGATCCCACC TCGATTCAGTGGCAGCGGGTATGGAACAGATT TTACCCTCACAATTAATAACATAGAATCTGAGG ATGCTGCATATTACTTCTGTCAGAATGATTATA GTTATCCGTACACGTTCGGCCAAGGGACCAAG GTGGAAATCAAA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 48 | LC | DIQMTQSPSSLSASVGDRVTITCKSSQSLLDSGNQ KNFLTWYQQKPGQAPRLLIYWASTRESGIPPRFS GSGYGTDFTLTINNIESEDAAYYFCQNDYSYPYTF GQGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC |
|---|---|---|
| SEQ ID NO: 49 | DNA LC | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGATCCCACC TCGATTCAGTGGCAGCGGGTATGGAACAGATT TTACCCTCACAATTAATAACATAGAATCTGAGG ATGCTGCATATTACTTCTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum04 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSS |
| SEQ ID NO: 51 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCC |
| SEQ ID NO: 52 | HC | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSSASTKGPSVFPLAPCSRST SESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFN WYVDGVEVHNAKTKPREEQFNSTYRVVSVLTVL HQDWLNGKEYKCKVSNKGLPSSIEKTISKAKGQP REPQVYTLPPSQEEMTKNQVSLTCLVKGFYPSDIA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | VEWESNGQPENNYKTTPPVLDSDGSFFLYSRLTV DKSRWQEGNVFSCSVMHEALHNHYTQKSLSLSL GK |
| SEQ ID NO: 53 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG TTCCCCCCAAAACCCAAGGACACTCTCATGATC TCCCGGACCCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCAGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |

BAP049-hum04 LC

| | | | |
|---|---|---|---|
| SEQ ID NO: 10 | (Kabat) | LCDR1 | KSSQSLLDSGNQKNFLT |
| SEQ ID NO: 11 | (Kabat) | LCDR2 | WASTRES |
| SEQ ID NO: 32 | (Kabat) | LCDR3 | QNDYSYPYT |
| SEQ ID NO: 13 | (Chothia) | LCDR1 | SQSLLDSGNQKNF |
| SEQ ID NO: 14 | (Chothia) | LCDR2 | WAS |
| SEQ ID NO: 33 | (Chothia) | LCDR3 | DYSYPY |
| SEQ ID NO: 54 | | VL | EIVLTQSPATLSLSPGERATLSCKSSQSLLDSGNQK NFLTWYQQKPGKAPKLLIYWASTRESGVPSRFSG SGSGTDFTFTISSLQPEDIATYYCQNDYSYPYTFG QGTKVEIK |
| SEQ ID NO: 55 | | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTATCAGCA GAAACCAGGGAAAGCTCCTAAGCTCCTGATCTA TTGGGCATCCACTAGGGAATCTGGGGTCCCATC AAGGTTCAGTGGAAGTGGATCTGGGACAGATT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TTACTTTCACCATCAGCAGCCTGCAGCCTGAAG ATATTGCAACATATTACTGTCAGAATGATTATA GTTATCCGTACACGTTCGGCCAAGGGACCAAG GTGGAAATCAAA |
| SEQ ID NO: 56 | LC | EIVLTQSPATLSLSPGERATLSCKSSQSLLDSGNQK NFLTWYQQKPGKAPKLLIYWASTRESGVPSRFSG SGSGTDFTFTISSLQPEDIATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 57 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTATCAGCA GAAACCAGGGAAAGCTCCTAAGCTCCTGATCTA TTGGGCATCCACTAGGGAATCTGGGGTCCCATC AAGGTTCAGTGGAAGTGGATCTGGGACAGATT TTACTTTCACCATCAGCAGCCTGCAGCCTGAAG ATATTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |
| BAP049-hum05 HC | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |
| SEQ ID NO: 40 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 41 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG GACAAGAGCAGGTGGCAGGAGGGGAATGTCT TCTCATGCTCCGTGATGCATGAGGCTCTGCACA ACCACTACACACAGAAGAGCCTCTCCCTGTCTC TGGGTAAA |

BAP049-hum05 LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLDSGNQK NFLTWYQQKPGKAPKLLIYWASTRESGVPSRFSG SGSGTDFTFTISSLQPEDIATYYCQNDYSYPYTFG QGTKVEIK |
| SEQ ID NO: 55 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AAATCAAAAGAACTTCTTGACCTGGTATCAGCA GAAACCAGGGAAAGCTCCTAAGCTCCTGATCTA TTGGGCATCCACTAGGGAATCTGGGGTCCCATC AAGGTTCAGTGGAAGTGGATCTGGGACAGATT TTACTTTCACCATCAGCAGCCTGCAGCCTGAAG ATATTGCAACATATTACTGTCAGAATGATTATA GTTATCCGTACACGTTCGGCCAAGGGACCAAG GTGGAAATCAAA |
| SEQ ID NO: 56 | LC | EIVLTQSPATLSLSPGERATLSCKSSQSLLDSGNQK NFLTWYQQKPGKAPKLLIYWASTRESGVPSRFSG SGSGTDFTFTISSLQPEDIATYYCQNDYSYPYTFG QGTKVEIKRTVAAPSVFIFPPSDEQLKSGTASVVC LLNNFYPREAKVQWKVDNA LQSGNSQESVTEQ DSKDSTYSLSSTLTLSKADYEKHKVYACEVTHQGL SSPVTKSFNRGEC |
| SEQ ID NO: 57 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTATCAGCA GAAACCAGGGAAAGCTCCTAAGCTCCTGATCTA TTGGGCATCCACTAGGGAATCTGGGGTCCCATC AAGGTTCAGTGGAAGTGGATCTGGGACAGATT TTACTTTCACCATCAGCAGCCTGCAGCCTGAAG ATATTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum06 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |
| SEQ ID NO: 40 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 41 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG GACAAGAGCAGGTGGCAGGAGGGGAATGTCT TCTCATGCTCCGTGATGCATGAGGCTCTGCACA ACCACTACACACAGAAGAGCCTCTCCCTGTCTC TGGGTAAA |

BAP049-hum06 LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 58 | VL | DIVMTQTPLSLPVTPGEPASISCKSSQSLLDSGNQ KNFLTWYQQKPGQAPRLLIYWASTRESGVPSRFS GSGSGTDFTFTISSLEAEDAATYYCQNDYSYPYTF GQGTKVEIK |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 59 | DNA VL | GATATTGTGATGACCCAGACTCCACTCTCCCTG CCCGTCACCCCTGGAGAGCCGGCCTCCATCTCC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 60 | LC | DIVMTQTPLSLPVTPGEPASISCKSSQSLLDSGNQ KNFLTWYQQKPGQAPRLLIYWASTRESGVPSRFS GSGSGTDFTFTISSLEAEDAATYYCQNDYSYPYTF GQGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC |
| SEQ ID NO: 61 | DNA LC | GATATTGTGATGACCCAGACTCCACTCTCCCTG CCCGTCACCCCTGGAGAGCCGGCCTCCATCTCC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum07 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 40 | | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
|---|---|---|---|
| SEQ ID NO: 41 | | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG GACAAGAGCAGGTGGCAGGAGGGGAATGTCT TCTCATGCTCCGTGATGCATGAGGCTCTGCACA ACCACTACACACAGAAGAGCCTCTCCCTGTCTC TGGGTAAA |
| | | BAP049-hum07 LC | |
| SEQ ID NO: 10 (Kabat) | | LCDR1 | KSSQSLLDSGNQKNFLT |
| SEQ ID NO: 11 (Kabat) | | LCDR2 | WASTRES |
| SEQ ID NO: 32 (Kabat) | | LCDR3 | QNDYSYPYT |
| SEQ ID NO: 13 (Chothia) | | LCDR1 | SQSLLDSGNQKNF |
| SEQ ID NO: 14 (Chothia) | | LCDR2 | WAS |
| SEQ ID NO: 33 (Chothia) | | LCDR3 | DYSYPY |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 62 | VL | EIVLTQSPATLSLSPGERATLSCKSSQSLLDSGNQK NFLTWYQQKPGKAPKLLIYWASTRESGVPSRFSG SGSGTDFTFTISSLEAEDAATYYCQNDYSYPYTFG QGTKVEIK |
| SEQ ID NO: 63 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTATCAGCA GAAACCAGGGAAAGCTCCTAAGCTCCTGATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 64 | LC | EIVLTQSPATLSLSPGERATLSCKSSQSLLDSGNQK NFLTWYQQKPGKAPKLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 65 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTATCAGCA GAAACCAGGGAAAGCTCCTAAGCTCCTGATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |
| BAP049-hum08 HC | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSS |
| SEQ ID NO: 51 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCC |
| SEQ ID NO: 52 | HC | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSSASTKGPSVFPLAPCSRST SESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFN WYVDGVEVHNAKTKPREEQFNSTYRVVSVLTVL HQDWLNGKEYKCKVSNKGLPSSIEKTISKAKGQP REPQVYTLPPSQEEMTKNQVSLTCLVKGFYPSDIA VEWESNGQPENNYKTTPPVLDSDGSFFLYSRLTV DKSRWQEGNVFSCSVMHEALHNHYTQKSLSLSL GK |
| SEQ ID NO: 53 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG TTCCCCCCAAAACCCAAGGACACTCTCATGATC TCCCGGACCCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCAGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |

BAP049-hum08 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 68 | LC | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum09 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |
| SEQ ID NO: 40 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 41 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG GACAAGAGCAGGTGGCAGGAGGGGAATGTCT TCTCATGCTCCGTGATGCATGAGGCTCTGCACA ACCACTACACACAGAAGAGCCTCTCCCTGTCTC TGGGTAAA |

BAP049-hum09 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 32 (Kabat) | LCDR3 | QNDYSYPYT |
|---|---|---|
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 68 | LC | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum10 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSS |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 51 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCC |
| SEQ ID NO: 52 | HC | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSSASTKGPSVFPLAPCSRST SESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFN WYVDGVEVHNAKTKPREEQFNSTYRVVSVLTVL HQDWLNGKEYKCKVSNKGLPSSIEKTISKAKGQP REPQVYTLPPSQEEMTKNQVSLTCLVKGFYPSDIA VEWESNGQPENNYKTTPPVLDSDGSFFLYSRLTV DKSRWQEGNVFSCSVMHEALHNHYTQKSLSLSL GK |
| SEQ ID NO: 53 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG TTCCCCCCAAAACCCAAGGACACTCTCATGATC TCCCGGACCCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCAGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-hum10 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 71 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 72 | LC | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 73 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum11 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |
| SEQ ID NO: 40 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 41 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | GACAAGAGCAGGTGGCAGGAGGGGAATGTCT<br>TCTCATGCTCCGTGATGCATGAGGCTCTGCACA<br>ACCACTACACACAGAAGAGCCTCTCCCTGTCTC<br>TGGGTAAA |

BAP049-hum11 LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQK<br>NFLTWYQQKPGQAPRLLIYWASTRESGVPSRFSG<br>SGSGTDFTFTISSLEAEDAATYYCQNDYSYPYTFG<br>QGTKVEIK |
| SEQ ID NO: 71 | DNA VL | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGG<br>AAATCAAAAGAACTTCTTGACCTGGTACCAGCA<br>GAAACCTGGCCAGGCTCCCAGGCTCCTCATCTA<br>TTGGGCATCCACTAGGGAATCTGGGGTCCCCTC<br>GAGGTTCAGTGGCAGTGGATCTGGGACAGATT<br>TCACCTTTACCATCAGTAGCCTGGAAGCTGAAG<br>ATGCTGCAACATATTACTGTCAGAATGATTATA<br>GTTATCCGTACACGTTCGGCCAAGGGACCAAG<br>GTGGAAATCAAA |
| SEQ ID NO: 72 | LC | EIVLTQSPATLSLSPGERATLSCKSSQSLLDSGNQK<br>NFLTWYQQKPGQAPRLLIYWASTRESGVPSRFSG<br>SGSGTDFTFTISSLEAEDAATYYCQNDYSYPYTFG<br>QGTKVEIKRTVAAPSVFIFPPSDEQLKSGTASVVC<br>LLNNFYPREAKVQWKVDNALQSGNSQESVTEQ<br>DSKDSTYSLSSTLTLSKADYEKHKVYACEVTHQGL<br>SSPVTKSFNRGEC |
| SEQ ID NO: 73 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGG<br>AAATCAAAAGAACTTCTTGACCTGGTACCAGCA<br>GAAACCTGGCCAGGCTCCCAGGCTCCTCATCTA<br>TTGGGCATCCACTAGGGAATCTGGGGTCCCCTC<br>GAGGTTCAGTGGCAGTGGATCTGGGACAGATT<br>TCACCTTTACCATCAGTAGCCTGGAAGCTGAAG<br>ATGCTGCAACATATTACTGTCAGAATGATTATA<br>GTTATCCGTACACGTTCGGCCAAGGGACCAAG<br>GTGGAAATCAAACGTACGGTGGCTGCACCATC<br>TGTCTTCATCTTCCCGCCATCTGATGAGCAGTTG<br>AAATCTGGAACTGCCTCTGTTGTGTGCCTGCTG<br>AATAACTTCTATCCCAGAGAGGCCAAAGTACAG<br>TGGAAGGTGGATAACGCCCTCCAATCGGGTAA<br>CTCCCAGGAGAGTGTCACAGAGCAGGACAGCA<br>AGGACAGCACCTACAGCCTCAGCAGCACCCTG<br>ACGCTGAGCAAAGCAGACTACGAGAAACACAA<br>AGTCTACGCCTGCGAAGTCACCCATCAGGGCCT<br>GAGCTCGCCCGTCACAAAGAGCTTCAACAGGG<br>GAGAGTGT |

BAP049-hum12 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 39 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCC |
| SEQ ID NO: 40 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 41 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCACTGGACAA GGGCTTGAGTGGATGGGTAATATTTATCCTGGT ACTGGTGGTTCTAACTTCGATGAGAAGTTCAAG AACAGAGTCACGATTACCGCGGACAAATCCAC GAGCACAGCCTACATGGAGCTGAGCAGCCTGA GATCTGAGGACACGGCCGTGTATTACTGTACA AGATGGACTACTGGGACGGGAGCTTATTGGGG CCAGGGCACCACCGTGACCGTGTCCTCCGCTTC CACCAAGGGCCCATCCGTCTTCCCCCTGGCGCC CTGCTCCAGGAGCACCTCCGAGAGCACAGCCG CCCTGGGCTGCCTGGTCAAGGACTACTTCCCCG AACCGGTGACGGTGTCGTGGAACTCAGGCGCC CTGACCAGCGGCGTGCACACCTTCCCGGCTGTC CTACAGTCCTCAGGACTCTACTCCCTCAGCAGC GTGGTGACCGTGCCCTCCAGCAGCTTGGGCAC GAAGACCTACACCTGCAACGTAGATCACAAGC CCAGCAACACCAAGGTGGACAAGAGAGTTGAG TCCAAATATGGTCCCCCATGCCCACCGTGCCCA GCACCTGAGTTCCTGGGGGGACCATCAGTCTTC CTGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGGT GCATAATGCCAAGACAAAGCCGCGGGAGGAG CAGTTCAACAGCACGTACCGTGTGGTCAGCGTC CTCACCGTCCTGCACCAGGACTGGCTGAACGG CAAGGAGTACAAGTGCAAGGTGTCCAACAAAG GCCTCCCGTCCTCCATCGAGAAAACCATCTCCA AAGCCAAAGGGCAGCCCCGAGAGCCACAGGT GTACACCCTGCCCCCATCCCAGGAGGAGATGA CCAAGAACCAGGTCAGCCTGACCTGCCTGGTC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | AAAGGCTTCTACCCCAGCGACATCGCCGTGGA GTGGGAGAGCAATGGGCAGCCGGAGAACAAC TACAAGACCACGCCTCCCGTGCTGGACTCCGAC GGCTCCTTCTTCCTCTACAGCAGGCTAACCGTG GACAAGAGCAGGTGGCAGGAGGGGAATGTCT TCTCATGCTCCGTGATGCATGAGGCTCTGCACA ACCACTACACACAGAAGAGCCTCTCCCTGTCTC TGGGTAAA |

BAP049-hum12 LC

| | | | |
|---|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 74 | VL | DIQMTQSPSSLSASVGDRVTITCKSSQSLLDSGNQ KNFLTWYLQKPGQSPQLLIYWASTRESGVPSRFS GSGSGTDFTFTISSLEAEDAATYYCQNDYSYPYTF GQGTKVEIK |
| SEQ ID NO: 75 | DNA VL | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCTGCA GAAGCCAGGGCAGTCTCCACAGCTCCTGATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 76 | LC | DIQMTQSPSSLSASVGDRVTITCKSSQSLLDSGNQ KNFLTWYLQKPGQSPQLLIYWASTRESGVPSRFS GSGSGTDFTFTISSLEAEDAATYYCQNDYSYPYTF GQGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC |
| SEQ ID NO: 77 | DNA LC | GACATCCAGATGACCCAGTCTCCATCCTCCCTG TCTGCATCTGTAGGAGACAGAGTCACCATCACT TGCAAGTCCAGTCAGAGTCTGTTAGACAGTGG AAATCAAAAGAACTTCTTGACCTGGTACCTGCA GAAGCCAGGGCAGTCTCCACAGCTCCTGATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-hum13 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWMHWVRQATGQGLEWMGNIYPGTGGSNFDEKFKNRVTITADKSTSTAYMELSSLRSEDTAVYYCTRWTTGTGAYWGQGTTVTVSS |
| SEQ ID NO: 39 | DNA VH | GAAGTGCAGCTGGTGCAGTCTGGAGCAGAGGTGAAAAAGCCCGGGGAGTCTCTGAGGATCTCCTGTAAGGGTTCTGGCTACACATTCACCACTTACTGGATGCACTGGGTGCGACAGGCCACTGGACAAGGGCTTGAGTGGATGGGTAATATTTATCCTGGTACTGGTGGTTCTAACTTCGATGAGAAGTTCAAGAACAGAGTCACGATTACCGCGGACAAATCCACGAGCACAGCCTACATGGAGCTGAGCAGCCTGAGATCTGAGGACACGGCCGTGTATTACTGTACAAGATGGACTACTGGGACGGGAGCTTATTGGGGCCAGGGCACCACCGTGACCGTGTCCTCC |
| SEQ ID NO: 40 | HC | EVQLVQSGAEVKKPGESLRISCKGSGYTFTTYWMHWVRQATGQGLEWMGNIYPGTGGSNFDEKFKNRVTITADKSTSTAYMELSSLRSEDTAVYYCTRWTTGTGAYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| SEQ ID NO: 41 | DNA HC | GAAGTGCAGCTGGTGCAGTCTGGAGCAGAGGTGAAAAAGCCCGGGGAGTCTCTGAGGATCTCCTGTAAGGGTTCTGGCTACACATTCACCACTTACTGGATGCACTGGGTGCGACAGGCCACTGGACAAGGGCTTGAGTGGATGGGTAATATTTATCCTGGTACTGGTGGTTCTAACTTCGATGAGAAGTTCAAGAACAGAGTCACGATTACCGCGGACAAATCCACGAGCACAGCCTACATGGAGCTGAGCAGCCTGAGATCTGAGGACACGGCCGTGTATTACTGTACAAGATGGACTACTGGGACGGGAGCTTATTGGGGCCAGGGCACCACCGTGACCGTGTCCTCCGCTTCCACCAAGGGCCCATCCGTCTTCCCCCTGGCGCCCTGCTCCAGGAGCACCTCCGAGAGCACAGCCGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACGAAGACCTACACCTGCAACGTAGATCACAAGCCCAGCAACACCAAGGTGGACAAGAGAGTTGAGTCCAAATATGGTCCCCCATGCCCACCGTGCCCAGCACCTGAGTTCCTGGGGGGACCATCAGTCTTCCTGTTCCCCCCAAAACCCAAGGACACTCTCATGATCTCCCGGACCCCTGAGGTCACGTGCGTGGTGGTGGACGTGAGCCAGGAAGACCCCGAGGTCCAGTTCAACTGGTACGTGGATGGCGTGGAGGT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|   |   |   |
|---|---|---|
|   |   | GCATAATGCCAAGACAAAGCCGCGGGAGGAG |
|   |   | CAGTTCAACAGCACGTACCGTGTGGTCAGCGTC |
|   |   | CTCACCGTCCTGCACCAGGACTGGCTGAACGG |
|   |   | CAAGGAGTACAAGTGCAAGGTGTCCAACAAAG |
|   |   | GCCTCCCGTCCTCCATCGAGAAAACCATCTCCA |
|   |   | AAGCCAAAGGGCAGCCCCGAGAGCCACAGGT |
|   |   | GTACACCCTGCCCCCATCCCAGGAGGAGATGA |
|   |   | CCAAGAACCAGGTCAGCCTGACCTGCCTGGTC |
|   |   | AAAGGCTTCTACCCCAGCGACATCGCCGTGGA |
|   |   | GTGGGAGAGCAATGGGCAGCCGGAGAACAAC |
|   |   | TACAAGACCACGCCTCCCGTGCTGGACTCCGAC |
|   |   | GGCTCCTTCTTCCTCTACAGCAGGCTAACCGTG |
|   |   | GACAAGAGCAGGTGGCAGGAGGGGAATGTCT |
|   |   | TCTCATGCTCCGTGATGCATGAGGCTCTGCACA |
|   |   | ACCACTACACACAGAAGAGCCTCTCCCTGTCTC |
|   |   | TGGGTAAA |

BAP049-hum13 LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 78 | VL | DVVMTQSPLSLPVTLGQPASISCKSSQSLLDSGN QKNFLTWYQQKPGKAPKLLIYWASTRESGVPSRF SGSGSGTDFTFTISSLEAEDAATYYCQNDYSYPYTF GQGTKVEIK |
| SEQ ID NO: 79 | DNA VL | GATGTTGTGATGACTCAGTCTCCACTCTCCCTG CCCGTCACCCTTGGACAGCCGGCCTCCATCTCC TGCAAGTCCAGTCAGAGTCTGTTAGACAGTGG AAATCAAAAGAACTTCTTAACCTGGTATCAGCA GAAACCAGGGAAAGCTCCTAAGCTCCTGATCTA TTGGGCATCCACTAGGGAATCGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 80 | LC | DVVMTQSPLSLPVTLGQPASISCKSSQSLLDSGN QKNFLTWYQQKPGKAPKLLIYWASTRESGVPSRF SGSGSGTDFTFTISSLEAEDAATYYCQNDYSYPYTF GQGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC |
| SEQ ID NO: 81 | DNA LC | GATGTTGTGATGACTCAGTCTCCACTCTCCCTG CCCGTCACCCTTGGACAGCCGGCCTCCATCTCC TGCAAGTCCAGTCAGAGTCTGTTAGACAGTGG AAATCAAAAGAACTTCTTAACCTGGTATCAGCA GAAACCAGGGAAAGCTCCTAAGCTCCTGATCTA TTGGGCATCCACTAGGGAATCGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

ACGCTGAGCAAAGCAGACTACGAGAAACACAA
AGTCTACGCCTGCGAAGTCACCCATCAGGGCCT
GAGCTCGCCCGTCACAAAGAGCTTCAACAGGG
GAGAGTGT

BAP049-hum14 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 82 | VH | QVQLVQSGAEVKKPGASVKVSCKASGYTFTTYW MHWIRQSPSRGLEWLGNIYPGTGGSNFDEKFKN RFTISRDNSKNTLYLQMNSLRAEDTAVYYCTRWT TGTGAYWGQGTTVTVSS |
| SEQ ID NO: 83 | DNA VH | CAGGTTCAGCTGGTGCAGTCTGGAGCTGAGGT GAAGAAGCCTGGGGCCTCAGTGAAGGTCTCCT GCAAGGCTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTACTGGGGCC AGGGCACCACCGTGACCGTGTCCTCC |
| SEQ ID NO: 84 | HC | QVQLVQSGAEVKKPGASVKVSCKASGYTFTTYW MHWIRQSPSRGLEWLGNIYPGTGGSNFDEKFKN RFTISRDNSKNTLYLQMNSLRAEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LGK |
| SEQ ID NO: 85 | DNA HC | CAGGTTCAGCTGGTGCAGTCTGGAGCTGAGGT GAAGAAGCCTGGGGCCTCAGTGAAGGTCTCCT GCAAGGCTTCTGGCTACACATTCACCACTTACT GGATGCACTGGATCAGGCAGTCCCCATCGAGA GGCCTTGAGTGGCTGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTACTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA CCGGTGACGGTGTCGTGGAACTCAGGCGCCCT GACCAGCGGCGTGCACACCTTCCCGGCTGTCCT ACAGTCCTCAGGACTCTACTCCCTCAGCAGCGT GGTGACCGTGCCCTCCAGCAGCTTGGGCACGA AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | TTCCCCCCAAAACCCAAGGACACTCTCATGATC<br>TCCCGGACCCCTGAGGTCACGTGCGTGGTGGT<br>GGACGTGAGCCAGGAAGACCCCGAGGTCCAGT<br>TCAACTGGTACGTGGATGGCGTGGAGGTGCAT<br>AATGCCAAGACAAAGCCGCGGGAGGAGCAGTT<br>CAACAGCACGTACCGTGTGGTCAGCGTCCTCAC<br>CGTCCTGCACCAGGACTGGCTGAACGGCAAGG<br>AGTACAAGTGCAAGGTGTCCAACAAAGGCCTC<br>CCGTCCTCCATCGAGAAAACCATCTCCAAAGCC<br>AAAGGGCAGCCCCGAGAGCCACAGGTGTACAC<br>CCTGCCCCCATCCCAGGAGGAGATGACCAAGA<br>ACCAGGTCAGCCTGACCTGCCTGGTCAAAGGC<br>TTCTACCCCAGCGACATCGCCGTGGAGTGGGA<br>GAGCAATGGGCAGCCGGAGAACAACTACAAG<br>ACCACGCCTCCCGTGCTGGACTCCGACGGCTCC<br>TTCTTCCTCTACAGCAGGCTAACCGTGGACAAG<br>AGCAGGTGGCAGGAGGGGAATGTCTTCTCATG<br>CTCCGTGATGCATGAGGCTCTGCACAACCACTA<br>CACACAGAAGAGCCTCTCCCTGTCTCTGGGTAA<br>A |

BAP049-hum14 LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQK<br>NFLTWYQQKPGQAPRLLIYWASTRESGVPSRFSG<br>SGSGTDFTFTISSLEAEDAATYYCQNDYSYPYTFG<br>QGTKVEIK |
| SEQ ID NO: 71 | DNA VL | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGG<br>AAATCAAAAGAACTTCTTGACCTGGTACCAGCA<br>GAAACCTGGCCAGGCTCCCAGGCTCCTCATCTA<br>TTGGGCATCCACTAGGGAATCTGGGGTCCCCTC<br>GAGGTTCAGTGGCAGTGGATCTGGGACAGATT<br>TCACCTTTACCATCAGTAGCCTGGAAGCTGAAG<br>ATGCTGCAACATATTACTGTCAGAATGATTATA<br>GTTATCCGTACACGTTCGGCCAAGGGACCAAG<br>GTGGAAATCAAA |
| SEQ ID NO: 72 | LC | EIVLTQSPATLSLSPGERATLSCKSSQSLLDSGNQK<br>NFLTWYQQKPGQAPRLLIYWASTRESGVPSRFSG<br>SGSGTDFTFTISSLEAEDAATYYCQNDYSYPYTFG<br>QGTKVEIKRTVAAPSVFIFPPSDEQLKSGTASVVC<br>LLNNFYPREAKVQWKVDNALQSGNSQESVTEQ<br>DSKDSTYSLSSTLTLSKADYEKHKVYACEVTHQGL<br>SSPVTKSFNRGEC |
| SEQ ID NO: 73 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGG<br>AAATCAAAAGAACTTCTTGACCTGGTACCAGCA<br>GAAACCTGGCCAGGCTCCCAGGCTCCTCATCTA<br>TTGGGCATCCACTAGGGAATCTGGGGTCCCCTC<br>GAGGTTCAGTGGCAGTGGATCTGGGACAGATT<br>TCACCTTTACCATCAGTAGCCTGGAAGCTGAAG<br>ATGCTGCAACATATTACTGTCAGAATGATTATA<br>GTTATCCGTACACGTTCGGCCAAGGGACCAAG<br>GTGGAAATCAAACGTACGGTGGCTGCACCATC<br>TGTCTTCATCTTCCCGCCATCTGATGAGCAGTTG<br>AAATCTGGAACTGCCTCTGTTGTGTGCCTGCTG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | AATAACTTCTATCCCAGAGAGGCCAAAGTACAG<br>TGGAAGGTGGATAACGCCCTCCAATCGGGTAA<br>CTCCCAGGAGAGTGTCACAGAGCAGGACAGCA<br>AGGACAGCACCTACAGCCTCAGCAGCACCCTG<br>ACGCTGAGCAAAGCAGACTACGAGAAACACAA<br>AGTCTACGCCTGCGAAGTCACCCATCAGGGCCT<br>GAGCTCGCCCGTCACAAAGAGCTTCAACAGGG<br>GAGAGTGT |

BAP049-hum15 HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 82 | VH | QVQLVQSGAEVKKPGASVKVSCKASGYTFTTYW<br>MHWIRQSPSRGLEWLGNIYPGTGGSNFDEKFKN<br>RFTISRDNSKNTLYLQMNSLRAEDTAVYYCTRWT<br>TGTGAYWGQGTTVTVSS |
| SEQ ID NO: 83 | DNA VH | CAGGTTCAGCTGGTGCAGTCTGGAGCTGAGGT<br>GAAGAAGCCTGGGGCCTCAGTGAAGGTCTCCT<br>GCAAGGCTTCTGGCTACACATTCACCACTTACT<br>GGATGCACTGGATCAGGCAGTCCCCATCGAGA<br>GGCCTTGAGTGGCTGGGTAATATTTATCCTGGT<br>ACTGGTGGTTCTAACTTCGATGAGAAGTTCAAG<br>AACAGATTCACCATCTCCAGAGACAATTCCAAG<br>AACACGCTGTATCTTCAAATGAACAGCCTGAGA<br>GCCGAGGACACGGCCGTGTATTACTGTACAAG<br>ATGGACTACTGGGACGGGAGCTTACTGGGGCC<br>AGGGCACCACCGTGACCGTGTCCTCC |
| SEQ ID NO: 84 | HC | QVQLVQSGAEVKKPGASVKVSCKASGYTFTTYW<br>MHWIRQSPSRGLEWLGNIYPGTGGSNFDEKFKN<br>RFTISRDNSKNTLYLQMNSLRAEDTAVYYCTRWT<br>TGTGAYWGQGTTVTVSSASTKGPSVFPLAPCSRS<br>TSESTAALGCLVKDYFPEPVTVSWNSGALTSGVH<br>TFPAVLQSSGLYSLSSVVTVPSSSLGTKTYTCNVD<br>HKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTV<br>LHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLT<br>VDKSRWQEGNVFSCSVMHEALHNHYTQKSLSLS<br>LGK |
| SEQ ID NO: 85 | DNA HC | CAGGTTCAGCTGGTGCAGTCTGGAGCTGAGGT<br>GAAGAAGCCTGGGGCCTCAGTGAAGGTCTCCT<br>GCAAGGCTTCTGGCTACACATTCACCACTTACT<br>GGATGCACTGGATCAGGCAGTCCCCATCGAGA<br>GGCCTTGAGTGGCTGGGTAATATTTATCCTGGT<br>ACTGGTGGTTCTAACTTCGATGAGAAGTTCAAG<br>AACAGATTCACCATCTCCAGAGACAATTCCAAG<br>AACACGCTGTATCTTCAAATGAACAGCCTGAGA<br>GCCGAGGACACGGCCGTGTATTACTGTACAAG<br>ATGGACTACTGGGACGGGAGCTTACTGGGGCC<br>AGGGCACCACCGTGACCGTGTCCTCCGCTTCCA<br>CCAAGGGCCCATCCGTCTTCCCCCTGGCGCCCT<br>GCTCCAGGAGCACCTCCGAGAGCACAGCCGCC<br>CTGGGCTGCCTGGTCAAGGACTACTTCCCCGAA<br>CCGGTGACGGTGTCGTGGAACTCAGGCGCCCT<br>GACCAGCGGCGTGCACACCTTCCCGGCTGTCCT<br>ACAGTCCTCAGGACTCTACTCCCTCAGCAGCGT<br>GGTGACCGTGCCCTCCAGCAGCTTGGGCACGA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | AGACCTACACCTGCAACGTAGATCACAAGCCCA GCAACACCAAGGTGGACAAGAGAGTTGAGTCC AAATATGGTCCCCCATGCCCACCGTGCCCAGCA CCTGAGTTCCTGGGGGGACCATCAGTCTTCCTG TTCCCCCCAAAACCCAAGGACACTCTCATGATC TCCCGGACCCCTGAGGTCACGTGCGTGGTGGT GGACGTGAGCCAGGAAGACCCCGAGGTCCAGT TCAACTGGTACGTGGATGGCGTGGAGGTGCAT AATGCCAAGACAAAGCCGCGGGAGGAGCAGTT CAACAGCACGTACCGTGTGGTCAGCGTCCTCAC CGTCCTGCACCAGGACTGGCTGAACGGCAAGG AGTACAAGTGCAAGGTGTCCAACAAAGGCCTC CCGTCCTCCATCGAGAAAACCATCTCCAAAGCC AAAGGGCAGCCCCGAGAGCCACAGGTGTACAC CCTGCCCCCATCCCGGAGGAGATGACCAAGA ACCAGGTCAGCCTGACCTGCCTGGTCAAAGGC TTCTACCCCAGCGACATCGCCGTGGAGTGGGA GAGCAATGGGCAGCCGGAGAACAACTACAAG ACCACGCCTCCCGTGCTGGACTCCGACGGCTCC TTCTTCCTCTACAGCAGGCTAACCGTGGACAAG AGCAGGTGGCAGGAGGGGAATGTCTTCTCATG CTCCGTGATGCATGAGGCTCTGCACAACCACTA CACACAGAAGAGCCTCTCCCTGTCTCTGGGTAA A |
|  | BAP049-hum15 LC |  |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 68 | LC | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-hum16 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 86 | VH | EVQLVQSGAEVKKPGESLRISCKGSGYTFTTYWM HWVRQAPGQGLEWMGNIYPGTGGSNFDEKFK NRFTISRDNSKNTLYLQMNSLRAEDTAVYYCTRW TTGTGAYWGQGTTVTVSS |
| SEQ ID NO: 87 | DNA VH | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCCCTGGACAA GGGCTTGAGTGGATGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCC |
| SEQ ID NO: 88 | HC | EVQLVQSGAEVKKPGESLRISCKGSGYTFTTYWM HWVRQAPGQGLEWMGNIYPGTGGSNFDEKFK NRFTISRDNSKNTLYLQMNSLRAEDTAVYYCTRW TTGTGAYWGQGTTVTVSSASTKGPSVFPLAPCSR STSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPS VFLFPPKPKDTLMISRTPEVTCVVVDVSQEDPEV QFNWYVDGVEVHNAKTKPREEQFNSTYRVVSVL TVLHQDWLNGKEYKCKVSNKGLPSSIEKTISKAKG QPREPQVYTLPPSQEEMTKNQVSLTCLVKGFYPS DIAVEWESNGQPENNYKTTPPVLDSDGSFFLYSR LTVDKSRWQEGNVFSCSVMHEALHNHYTQKSLS LSLGK |
| SEQ ID NO: 89 | DNA HC | GAAGTGCAGCTGGTGCAGTCTGGAGCAGAGGT GAAAAAGCCCGGGGAGTCTCTGAGGATCTCCT GTAAGGGTTCTGGCTACACATTCACCACTTACT GGATGCACTGGGTGCGACAGGCCCCTGGACAA GGGCTTGAGTGGATGGGTAATATTTATCCTGGT ACTGGTGGTTCTAACTTCGATGAGAAGTTCAAG AACAGATTCACCATCTCCAGAGACAATTCCAAG AACACGCTGTATCTTCAAATGAACAGCCTGAGA GCCGAGGACACGGCCGTGTATTACTGTACAAG ATGGACTACTGGGACGGGAGCTTATTGGGGCC AGGGCACCACCGTGACCGTGTCCTCCGCTTCCA CCAAGGGCCCATCCGTCTTCCCCCTGGCGCCCT GCTCCAGGAGCACCTCCGAGAGCACAGCCGCC CTGGGCTGCCTGGTCAAGGACTACTTCCCCGAA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
CCGGTGACGGTGTCGTGGAACTCAGGCGCCCT
GACCAGCGGCGTGCACACCTTCCCGGCTGTCCT
ACAGTCCTCAGGACTCTACTCCCTCAGCAGCGT
GGTGACCGTGCCCTCCAGCAGCTTGGGCACGA
AGACCTACACCTGCAACGTAGATCACAAGCCCA
GCAACACCAAGGTGGACAAGAGAGTTGAGTCC
AAATATGGTCCCCCATGCCCACCGTGCCCAGCA
CCTGAGTTCCTGGGGGGACCATCAGTCTTCCTG
TTCCCCCCAAAACCCAAGGACACTCTCATGATC
TCCCGGACCCCTGAGGTCACGTGCGTGGTGGT
GGACGTGAGCCAGGAAGACCCCGAGGTCCAGT
TCAACTGGTACGTGGATGGCGTGGAGGTGCAT
AATGCCAAGACAAAGCCGCGGGAGGAGCAGTT
CAACAGCACGTACCGTGTGGTCAGCGTCCTCAC
CGTCCTGCACCAGGACTGGCTGAACGGCAAGG
AGTACAAGTGCAAGGTGTCCAACAAAGGCCTC
CCGTCCTCCATCGAGAAAACCATCTCCAAAGCC
AAAGGGCAGCCCCGAGAGCCACAGGTGTACAC
CCTGCCCCCATCCCGGAGGAGATGACCAAGA
ACCAGGTCAGCCTGACCTGCCTGGTCAAAGGC
TTCTACCCCAGCGACATCGCCGTGGAGTGGGA
GAGCAATGGGCAGCCGGAGAACAACTACAAG
ACCACGCCTCCCGTGCTGGACTCCGACGGCTCC
TTCTTCCTCTACAGCAGGCTAACCGTGGACAAG
AGCAGGTGGCAGGAGGGGAATGTCTTCTCATG
CTCCGTGATGCATGAGGCTCTGCACAACCACTA
CACACAGAAGAGCCTCTCCCTGTCTCTGGGTAA
A
```

BAP049-hum16 LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAA |
| SEQ ID NO: 68 | LC | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGG AAATCAAAAGAACTTCTTGACCTGGTACCAGCA GAAACCTGGCCAGGCTCCCAGGCTCCTCATCTA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | TTGGGCATCCACTAGGGAATCTGGGGTCCCCTC GAGGTTCAGTGGCAGTGGATCTGGGACAGATT TCACCTTTACCATCAGTAGCCTGGAAGCTGAAG ATGCTGCAACATATTACTGTCAGAATGATTATA GTTATCCGTACACGTTCGGCCAAGGGACCAAG GTGGAAATCAAACGTACGGTGGCTGCACCATC TGTCTTCATCTTCCCGCCATCTGATGAGCAGTTG AAATCTGGAACTGCCTCTGTTGTGTGCCTGCTG AATAACTTCTATCCCAGAGAGGCCAAAGTACAG TGGAAGGTGGATAACGCCCTCCAATCGGGTAA CTCCCAGGAGAGTGTCACAGAGCAGGACAGCA AGGACAGCACCTACAGCCTCAGCAGCACCCTG ACGCTGAGCAAAGCAGACTACGAGAAACACAA AGTCTACGCCTGCGAAGTCACCCATCAGGGCCT GAGCTCGCCCGTCACAAAGAGCTTCAACAGGG GAGAGTGT |

BAP049-Clone-A HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 90 | DNA VH | GAAGTGCAGCTGGTGCAGTCTGGCGCCGAAGT GAAGAAGCCTGGCGAGTCCCTGCGGATCTCCT GCAAGGGCTCTGGCTACACCTTCACCACCTACT GGATGCACTGGGTGCGACAGGCTACCGGCCAG GGCCTGGAATGGATGGGCAACATCTATCCTGG CACCGGCGGCTCCAACTTCGACGAGAAGTTCA AGAACAGAGTGACCATCACCGCCGACAAGTCC ACCTCCACCGCCTACATGGAACTGTCCTCCCTG AGATCCGAGGACACCGCCGTGTACTACTGCAC CCGGTGGACAACCGGCACAGGCGCTTATTGGG GCCAGGGCACCACAGTGACCGTGTCCTCT |
| SEQ ID NO: 91 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LG |
| SEQ ID NO: 92 | DNA HC | GAAGTGCAGCTGGTGCAGTCTGGCGCCGAAGT GAAGAAGCCTGGCGAGTCCCTGCGGATCTCCT GCAAGGGCTCTGGCTACACCTTCACCACCTACT GGATGCACTGGGTGCGACAGGCTACCGGCCAG GGCCTGGAATGGATGGGCAACATCTATCCTGG CACCGGCGGCTCCAACTTCGACGAGAAGTTCA AGAACAGAGTGACCATCACCGCCGACAAGTCC ACCTCCACCGCCTACATGGAACTGTCCTCCCTG AGATCCGAGGACACCGCCGTGTACTACTGCAC CCGGTGGACAACCGGCACAGGCGCTTATTGGG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
GCCAGGGCACCACAGTGACCGTGTCCTCTGCTT
CTACCAAGGGGCCCAGCGTGTTCCCCCTGGCCC
CCTGCTCCAGAAGCACCAGCGAGAGCACAGCC
GCCCTGGGCTGCCTGGTGAAGGACTACTTCCCC
GAGCCCGTGACCGTGTCCTGGAACAGCGGAGC
CCTGACCAGCGGCGTGCACACCTTCCCCGCCGT
GCTGCAGAGCAGCGGCCTGTACAGCCTGAGCA
GCGTGGTGACCGTGCCCAGCAGCAGCCTGGGC
ACCAAGACCTACACCTGTAACGTGGACCACAA
GCCCAGCAACACCAAGGTGGACAAGAGGGTG
GAGAGCAAGTACGGCCCACCCTGCCCCCCCTG
CCCAGCCCCCGAGTTCCTGGGCGGACCCAGCG
TGTTCCTGTTCCCCCCAAGCCCAAGGACACCC
TGATGATCAGCAGAACCCCCGAGGTGACCTGT
GTGGTGGTGGACGTGTCCCAGGAGGACCCCGA
GGTCCAGTTCAACTGGTACGTGGACGGCGTGG
AGGTGCACAACGCCAAGACCAAGCCCAGAGAG
GAGCAGTTTAACAGCACCTACCGGGTGGTGTC
CGTGCTGACCGTGCTGCACCAGGACTGGCTGA
ACGGCAAAGAGTACAAGTGTAAGGTCTCCAAC
AAGGGCCTGCCAAGCAGCATCGAAAAGACCAT
CAGCAAGGCCAAGGGCCAGCCTAGAGAGCCCC
AGGTCTACACCCTGCCACCCAGCCAAGAGGAG
ATGACCAAGAACCAGGTGTCCCTGACCTGTCTG
GTGAAGGGCTTCTACCCAAGCGACATCGCCGT
GGAGTGGGAGAGCAACGGCCAGCCCGAGAAC
AACTACAAGACCACCCCCCCAGTGCTGGACAGC
GACGGCAGCTTCTTCCTGTACAGCAGGCTGACC
GTGGACAAGTCCAGATGGCAGGAGGGCAACG
TCTTTAGCTGCTCCGTGATGCACGAGGCCCTGC
ACAACCACTACACCCAGAAGAGCCTGAGCCTGT
CCCTGGGC
```

BAP049-Clone-A LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 42 | VL | EIVLTQSPATLSLSPGERATLSCKSSQSLLDSGNQK NFLTWYQQKPGQAPRLLIYWASTRESGVPSRFSG SGSGTEFTLTISSLQPDDFATYYCQNDYSYPYTFG QGTKVEIK |
| SEQ ID NO: 93 | DNA VL | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTA CTGGGCCTCCACCCGGGAATCTGGCGTGCCCTC TAGATTCTCCGGCTCCGGCTCTGGCACCGAGTT TACCCTGACCATCTCCAGCCTGCAGCCCGACGA CTTCGCCACCTACTACTGCCAGAACGACTACTC CTACCCCTACACCTTCGGCCAGGGCACCAAGGT GGAAATCAAG |
| SEQ ID NO: 44 | LC | EIVLTQSPATLSLSPGERATLSCKSSQSLLDSGNQK NFLTWYQQKPGQAPRLLIYWASTRESGVPSRFSG SGSGTEFTLTISSLQPDDFATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 94 | DNA LC | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTA CTGGGCCTCCACCCGGGAATCTGGCGTGCCCTC TAGATTCTCCGGCTCCGGCTCTGGCACCGAGTT TACCCTGACCATCTCCAGCCTGCAGCCCGACGA CTTCGCCACCTACTACTGCCAGAACGACTACTC CTACCCCTACACCTTCGGCCAGGGCACCAAGGT GGAAATCAAGCGTACGGTGGCCGCTCCCAGCG TGTTCATCTTCCCCCCAAGCGACGAGCAGCTGA AGAGCGGCACCGCCAGCGTGGTGTGTCTGCTG AACAACTTCTACCCCAGGGAGGCCAAGGTGCA GTGGAAGGTGGACAACGCCCTGCAGAGCGGC AACAGCCAGGAGAGCGTCACCGAGCAGGACA GCAAGGACTCCACCTACAGCCTGAGCAGCACC CTGACCCTGAGCAAGGCCGACTACGAGAAGCA CAAGGTGTACGCCTGTGAGGTGACCCACCAGG GCCTGTCCAGCCCCGTGACCAAGAGCTTCAACA GGGGCGAGTGC |

BAP049-Clone-B HC

| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 95 | DNA VH | GAGGTGCAGCTGGTGCAGTCAGGCGCCGAAGT GAAGAAGCCCGGCGAGTCACTGAGAATTAGCT GTAAAGGTTCAGGCTACACCTTCACTACCTACT GGATGCACTGGGTCCGCCAGGCTACCGGTCAA GGCCTCGAGTGGATGGGTAATATCTACCCCGG CACCGGCGGCTCTAACTTCGACGAGAAGTTTAA GAATAGAGTGACTATCACCGCCGATAAGTCTAC TAGCACCGCCTATATGGAACTGTCTAGCCTGAG ATCAGAGGACACCGCCGTCTACTACTGCACTAG GTGGACTACCGGCACAGGCGCCTACTGGGGTC AAGGCACTACCGTGACCGTGTCTAGC |
| SEQ ID NO: 91 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LG |
| SEQ ID NO: 96 | DNA HC | GAGGTGCAGCTGGTGCAGTCAGGCGCCGAAGT GAAGAAGCCCGGCGAGTCACTGAGAATTAGCT GTAAAGGTTCAGGCTACACCTTCACTACCTACT GGATGCACTGGGTCCGCCAGGCTACCGGTCAA GGCCTCGAGTGGATGGGTAATATCTACCCCGG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | CACCGGCGGCTCTAACTTCGACGAGAAGTTTAA<br>GAATAGAGTGACTATCACCGCCGATAAGTCTAC<br>TAGCACCGCCTATATGGAACTGTCTAGCCTGAG<br>ATCAGAGGACACCGCCGTCTACTACTGCACTAG<br>GTGGACTACCGGCACAGGCGCCTACTGGGGTC<br>AAGGCACTACCGTGACCGTGTCTAGCGCTAGC<br>ACTAAGGGCCCGTCCGTGTTCCCCCTGGCACCT<br>TGTAGCCGGAGCACTAGCGAATCCACCGCTGC<br>CCTCGGCTGCCTGGTCAAGGATTACTTCCCGGA<br>GCCCGTGACCGTGTCCTGGAACAGCGGAGCCC<br>TGACCTCCGGAGTGCACACCTTCCCCGCTGTGC<br>TGCAGAGCTCCGGGCTGTACTCGCTGTCGTCG<br>GTGGTCACGGTGCCTTCATCTAGCCTGGGTACC<br>AAGACCTACACTTGCAACGTGGACCACAAGCCT<br>TCCAACACTAAGGTGGACAAGCGCGTCGAATC<br>GAAGTACGGCCCACCGTGCCCGCCTTGTCCCGC<br>GCCGGAGTTCCTCGGCGGTCCCTCGGTCTTTCT<br>GTTCCCACCGAAGCCCAAGGACACTTTGATGAT<br>TTCCCGCACCCCTGAAGTGACATGCGTGGTCGT<br>GGACGTGTCACAGGAAGATCCGGAGGTGCAGT<br>TCAATTGGTACGTGGATGGCGTCGAGGTGCAC<br>AACGCCAAAACCAAGCCGAGGGAGGAGCAGTT<br>CAACTCCACTTACCGCGTCGTGTCCGTGCTGAC<br>GGTGCTGCATCAGGACTGGCTGAACGGGAAG<br>GAGTACAAGTGCAAAGTGTCCAACAAGGGACT<br>TCCTAGCTCAATCGAAAAGACCATCTCGAAAGC<br>CAAGGGACAGCCCCGGGAACCCCAAGTGTATA<br>CCCTGCCACCGAGCCAGGAAGAAATGACTAAG<br>AACCAAGTCTCATTGACTTGCCTTGTGAAGGGC<br>TTCTACCCATCGGATATCGCCGTGGAATGGGA<br>GTCCAACGGCCAGCCGGAAAACAACTACAAGA<br>CCACCCCTCCGGTGCTGGACTCAGACGGATCCT<br>TCTTCCTCTACTCGCGGCTGACCGTGGATAAGA<br>GCAGATGGCAGGAGGGAAATGTGTTCAGCTGT<br>TCTGTGATGCATGAAGCCCTGCACAACCACTAC<br>ACTCAGAAGTCCCTGTCCCTCTCCCTGGGA |
|  | BAP049-Clone-B LC |  |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLDSGNQK<br>NFLTWYQQKPGKAPKLLIYWASTRESGVPSRFSG<br>SGSGTDFTFTISSLQPEDIATYYCQNDYSYPYTFG<br>QGTKVEIK |
| SEQ ID NO: 97 | DNA VL | GAGATCGTCCTGACTCAGTCACCCGCTACCCTG<br>AGCCTGAGCCCTGGCGAGCGGGCTACACTGAG<br>CTGTAAATCTAGTCAGTCACTGCTGGATAGCGG<br>TAATCAGAAGAACTTCCTGACCTGGTATCAGCA<br>GAAGCCCGGTAAAGCCCCTAAGCTGCTGATCT<br>ACTGGGCCTCTACTAGAGAATCAGGCGTGCCCT<br>CTAGGTTTAGCGGTAGCGGTAGTGGCACCGAC<br>TTCACCTTCACTATCTCTAGCCTGCAGCCCGAG<br>GATATCGCTACCTACTACTGTCAGAACGACTAT<br>AGCTACCCCTACACCTTCGGTCAAGGCACTAAG<br>GTCGAGATTAAG |
| SEQ ID NO: 56 | LC | EIVLTQSPATLSLSPGERATLSCKSSQSLLDSGNQK<br>NFLTWYQQKPGKAPKLLIYWASTRESGVPSRFSG<br>SGSGTDFTFTISSLQPEDIATYYCQNDYSYPYTFG<br>QGTKVEIKRTVAAPSVFIFPPSDEQLKSGTASVVC<br>LLNNFYPREAKVQWKVDNALQSGNSQESVTEQ |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | DSKDSTYSLSSTLTLSKADYEKHKVYACEVTHQGL SSPVTKSFNRGEC |
| SEQ ID NO: 98 | DNA LC | GAGATCGTCCTGACTCAGTCACCCGCTACCCTG AGCCTGAGCCCTGGCGAGCGGGCTACACTGAG CTGTAAATCTAGTCAGTCACTGCTGGATAGCGG TAATCAGAAGAACTTCCTGACCTGGTATCAGCA GAAGCCCGGTAAAGCCCCTAAGCTGCTGATCT ACTGGGCCTCTACTAGAGAATCAGGCGTGCCCT CTAGGTTTAGCGGTAGCGGTAGTGGCACCGAC TTCACCTTCACTATCTCTAGCCTGCAGCCCGAG GATATCGCTACCTACTACTGTCAGACGACTAT AGCTACCCCTACACCTTCGGTCAAGGCACTAAG GTCGAGATTAAGCGTACGGTGGCCGCTCCCAG CGTGTTCATCTTCCCCCCCAGCGACGAGCAGCT GAAGAGCGGCACCGCCAGCGTGGTGTGCCTGC TGAACAACTTCTACCCCGGGAGGCCAAGGTG CAGTGGAAGGTGGACAACGCCCTGCAGAGCG GCAACAGCCAGGAGAGCGTCACCGAGCAGGA CAGCAAGGACTCCACCTACAGCCTGAGCAGCA CCCTGACCCTGAGCAAGGCCGACTACGAGAAG CATAAGGTGTACGCCTGCGAGGTGACCCACCA GGGCCTGTCCAGCCCCGTGACCAAGAGCTTCA ACAGGGGCGAGTGC |

BAP049-Clone-C HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 90 | DNA VH | GAAGTGCAGCTGGTGCAGTCTGGCGCCGAAGT GAAGAAGCCTGGCGAGTCCCTGCGGATCTCCT GCAAGGGCTCTGGCTACACCTTCACCACCTACT GGATGCACTGGGTGCGACAGGCTACCGGCCAG GGCCTGGAATGGATGGGCAACATCTATCCTGG CACCGGCGGCTCCAACTTCGACGAGAAGTTCA AGAACAGAGTGACCATCACCGCCGACAAGTCC ACCTCCACCGCCTACATGGAACTGTCCTCCCTG AGATCCGAGGACACCGCCGTGTACTACTGCAC CCGGTGGACAACCGGCACAGGCGCTTATTGGG GCCAGGGCACCACAGTGACCGTGTCCTCT |
| SEQ ID NO: 91 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 92 | DNA HC | GAAGTGCAGCTGGTGCAGTCTGGCGCCGAAGT<br>GAAGAAGCCTGGCGAGTCCCTGCGGATCTCCT<br>GCAAGGGCTCTGGCTACACCTTCACCACCTACT<br>GGATGCACTGGGTGCGACAGGCTACCGGCCAG<br>GGCCTGGAATGGATGGGCAACATCTATCCTGG<br>CACCGGCGGCTCCAACTTCGACGAGAAGTTCA<br>AGAACAGAGTGACCATCACCGCCGACAAGTCC<br>ACCTCCACCGCCTACATGGAACTGTCCTCCCTG<br>AGATCCGAGGACACCGCCGTGTACTACTGCAC<br>CCGGTGGACAACCGGCACAGGCGCTTATTGGG<br>GCCAGGGCACCACAGTGACCGTGTCCTCTGCTT<br>CTACCAAGGGGCCCAGCGTGTTCCCCCTGGCCC<br>CCTGCTCCAGAAGCACCAGCGAGAGCACAGCC<br>GCCCTGGGCTGCCTGGTGAAGGACTACTTCCCC<br>GAGCCCGTGACCGTGTCCTGGAACAGCGGAGC<br>CCTGACCAGCGGCGTGCACACCTTCCCCGCCGT<br>GCTGCAGAGCAGCGGCCTGTACAGCCTGAGCA<br>GCGTGGTGACCGTGCCCAGCAGCAGCCTGGGC<br>ACCAAGACCTACACCTGTAACGTGGACCACAA<br>GCCCAGCAACACCAAGGTGGACAAGAGGGTG<br>GAGAGCAAGTACGGCCCACCCTGCCCCCCCTG<br>CCCAGCCCCGAGTTCCTGGGCGGACCCAGCG<br>TGTTCCTGTTCCCCCCCAAGCCCAAGGACACCC<br>TGATGATCAGCAGAACCCCCGAGGTGACCTGT<br>GTGGTGGTGGACGTGTCCCAGGAGGACCCCGA<br>GGTCCAGTTCAACTGGTACGTGGACGGCGTGG<br>AGGTGCACAACGCCAAGACCAAGCCCAGAGAG<br>GAGCAGTTTAACAGCACCTACCGGGTGGTGTC<br>CGTGCTGACCGTGCTGCACCAGGACTGGCTGA<br>ACGGCAAAGAGTACAAGTGTAAGGTCTCCAAC<br>AAGGGCCTGCCAAGCAGCATCGAAAAGACCAT<br>CAGCAAGGCCAAGGGCCAGCCTAGAGAGCCCC<br>AGGTCTACACCCTGCCACCCAGCCAAGAGGAG<br>ATGACCAAGAACCAGGTGTCCCTGACCTGTCTG<br>GTGAAGGGCTTCTACCCAAGCGACATCGCCGT<br>GGAGTGGGAGAGCAACGGCCAGCCCGAGAAC<br>AACTACAAGACCACCCCCCCAGTGCTGGACAGC<br>GACGGCAGCTTCTTCCTGTACAGCAGGCTGACC<br>GTGGACAAGTCCAGATGGCAGGAGGGCAACG<br>TCTTTAGCTGCTCCGTGATGCACGAGGCCCTGC<br>ACAACCACTACACCCAGAAGAGCCTGAGCCTGT<br>CCCTGGGC |

BAP049-Clone-C LC

| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSGNQK<br>NFLTWYQQKPGQAPRLLIYWASTRESGVPSRFSG<br>SGSGTDFTFTISSLEAEDAATYYCQNDYSYPYTFG<br>QGTKVEIK |
| SEQ ID NO: 99 | DNA VL | GAGATCGTGCTGACCCAGTCCCCCGACTTCCAG<br>TCCGTGACCCCCAAAGAAAAAGTGACCATCACA<br>TGCAAGTCCTCCCAGTCCCTGCTGGACTCCGGC<br>AACCAGAAGAACTTCCTGACCTGGTATCAGCAG<br>AAGCCCGGCCAGGCCCCCAGACTGCTGATCTA<br>CTGGGCCTCCACCCGGGAATCTGGCGTGCCCTC<br>TAGATTCTCCGGCTCCGGCTCTGGCACCGACTT<br>TACCTTCACCATCTCCAGCCTGGAAGCCGAGGA<br>CGCCGCCACCTACTACTGCCAGAACGACTACTC<br>CTACCCCTACACCTTCGGCCAGGGCACCAAGGT<br>GGAAATCAAG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 68 | LC | EIVLTQSPDFQSVTPKEKVTITCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
|---|---|---|
| SEQ ID NO: 100 | DNA LC | GAGATCGTGCTGACCCAGTCCCCCGACTTCCAG TCCGTGACCCCCAAAGAAAAAGTGACCATCACA TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTA CTGGGCCTCCACCCGGGAATCTGGCGTGCCCTC TAGATTCTCCGGCTCCGGCTCTGGCACCGACTT TACCTTCACCATCTCCAGCCTGGAAGCCGAGGA CGCCGCCACCTACTACTGCCAGAACGACTACTC CTACCCCTACACCTTCGGCCAGGGCACCAAGGT GGAAATCAAGCGTACGGTGGCCGCTCCCAGCG TGTTCATCTTCCCCCCAAGCGACGAGCAGCTGA AGAGCGGCACCGCCAGCGTGGTGTGTCTGCTG AACAACTTCTACCCCAGGGAGGCCAAGGTGCA GTGGAAGGTGGACAACGCCCTGCAGAGCGGC AACAGCCAGGAGAGCGTCACCGAGCAGGACA GCAAGGACTCCACCTACAGCCTGAGCAGCACC CTGACCCTGAGCAAGGCCGACTACGAGAAGCA CAAGGTGTACGCCTGTGAGGTGACCCACCAGG GCCTGTCCAGCCCCGTGACCAAGAGCTTCAACA GGGGCGAGTGC |

BAP049-Clone-D HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSS |
| SEQ ID NO: 101 | DNA VH | GAAGTGCAGCTGGTGCAGTCTGGCGCCGAAGT GAAGAAGCCTGGCGAGTCCCTGCGGATCTCCT GCAAGGGCTCTGGCTACACCTTCACCACCTACT GGATGCACTGGATCCGGCAGTCCCCCTCTAGG GGCCTGGAATGGCTGGGCAACATCTACCCTGG CACCGGCGGCTCCAACTTCGACGAGAAGTTCA AGAACAGGTTCACCATCTCCCGGGACAACTCCA AGAACACCCTGTACCTGCAGATGAACTCCCTGC GGGCCGAGGACACCGCCGTGTACTACTGTACC AGATGGACCACCGGAACCGGCGCCTATTGGGG CCAGGGCACAACAGTGACCGTGTCCTCC |
| SEQ ID NO: 102 | HC | EVQLVQSGAEVKKPGESLRISCKGSGYTFTTYWM HWIRQSPSRGLEWLGNIYPGTGGSNFDEKFKNR FTISRDNSKNTLYLQMNSLRAEDTAVYYCTRWTT GTGAYWGQGTTVTVSSASTKGPSVFPLAPCSRST SESTAALGCLVKDYFPEPVTVSWNSGALTSGVHT FPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFN WYVDGVEVHNAKTKPREEQFNSTYRVVSVLTVL HQDWLNGKEYKCKVSNKGLPSSIEKTISKAKGQP REPQVYTLPPSQEEMTKNQVSLTCLVKGFYPSDIA |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | VEWESNGQPENNYKTTPPVLDSDGSFFLYSRLTV DKSRWQEGNVFSCSVMHEALHNHYTQKSLSLSL G |
| SEQ ID NO: 103 | DNA HC | GAAGTGCAGCTGGTGCAGTCTGGCGCCGAAGT GAAGAAGCCTGGCGAGTCCCTGCGGATCTCCT GCAAGGGCTCTGGCTACACCTTCACCACCTACT GGATGCACTGGATCCGGCAGTCCCCCTCTAGG GGCCTGGAATGGCTGGGCAACATCTACCCTGG CACCGGCGGCTCCAACTTCGACGAGAAGTTCA AGAACAGGTTCACCATCTCCCGGGACAACTCCA AGAACACCCTGTACCTGCAGATGAACTCCCTGC GGGCCGAGGACACCGCCGTGTACTACTGTACC AGATGGACCACCGGAACCGGCGCCTATTGGGG CCAGGGCACAACAGTGACCGTGTCCTCCGCTTC TACCAAGGGGCCCAGCGTGTTCCCCCTGGCCCC CTGCTCCAGAAGCACCAGCGAGAGCACAGCCG CCCTGGGCTGCCTGGTGAAGGACTACTTCCCCG AGCCCGTGACCGTGTCCTGGAACAGCGGAGCC CTGACCAGCGGCGTGCACACCTTCCCCGCCGTG CTGCAGAGCAGCGGCCTGTACAGCCTGAGCAG CGTGGTGACCGTGCCCAGCAGCAGCCTGGGCA CCAAGACCTACACCTGTAACGTGGACCACAAGC CCAGCAACACCAAGGTGGACAAGAGGGTGGA GAGCAAGTACGGCCCCACCCTGCCCCCCCTGCCC AGCCCCCGAGTTCCTGGGCGGACCCAGCGTGT TCCTGTTCCCCCCCAAGCCCAAGGACACCCTGA TGATCAGCAGAACCCCCGAGGTGACCTGTGTG GTGGTGGACGTGTCCCAGGAGGACCCCGAGGT CCAGTTCAACTGGTACGTGGACGGCGTGGAGG TGCACAACGCCAAGACCAAGCCCAGAGAGGAG CAGTTTAACAGCACCTACCGGGTGGTGTCCGTG CTGACCGTGCTGCACCAGGACTGGCTGAACGG CAAAGAGTACAAGTGTAAGGTCTCCAACAAGG GCCTGCCAAGCAGCATCGAAAAGACCATCAGC AAGGCCAAGGGCCAGCCTAGAGAGCCCCAGGT CTACACCCTGCCACCCAGCCAAGAGGAGATGA CCAAGAACCAGGTGTCCCTGACCTGTCTGGTGA AGGGCTTCTACCCAAGCGACATCGCCGTGGAG TGGGAGAGCAACGGCCAGCCCGAGAACAACTA CAAGACCACCCCCCCAGTGCTGGACAGCGACG GCAGCTTCTTCCTGTACAGCAGGCTGACCGTGG ACAAGTCCAGATGGCAGGAGGGCAACGTCTTT AGCTGCTCCGTGATGCACGAGGCCCTGCACAA CCACTACACCCAGAAGAGCCTGAGCCTGTCCCT GGGC |

BAP049-Clone-D LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIK |
| SEQ ID NO: 104 | DNA VL | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTA CTGGGCCTCCACCCGGGAATCTGGCGTGCCCTC TAGATTCTCCGGCTCCGGCTCTGGCACCGACTT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | TACCTTCACCATCTCCAGCCTGGAAGCCGAGGA CGCCGCCACCTACTACTGCCAGAACGACTACTC CTACCCCTACACCTTCGGCCAGGGCACCAAGGT GGAAATCAAG |
| SEQ ID NO: 72 | LC | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 105 | DNA LC | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTA CTGGGCCTCCACCCGGGAATCTGGCGTGCCCTC TAGATTCTCCGGCTCCGGCTCTGGCACCGACTT TACCTTCACCATCTCCAGCCTGGAAGCCGAGGA CGCCGCCACCTACTACTGCCAGAACGACTACTC CTACCCCTACACCTTCGGCCAGGGCACCAAGGT GGAAATCAAGCGTACGGTGGCCGCTCCCAGCG TGTTCATCTTCCCCCCAAGCGACGAGCAGCTGA AGAGCGGCACCGCCAGCGTGGTGTGTCTGCTG AACAACTTCTACCCCAGGGAGGCCAAGGTGCA GTGGAAGGTGGACAACGCCCTGCAGAGCGGC AACAGCCAGGAGAGCGTCACCGAGCAGGACA GCAAGGACTCCACCTACAGCCTGAGCAGCACC CTGACCCTGAGCAAGGCCGACTACGAGAAGCA CAAGGTGTACGCCTGTGAGGTGACCCACCAGG GCCTGTCCAGCCCCGTGACCAAGAGCTTCAACA GGGGCGAGTGC |

BAP049-Clone-E HC

| SEQ ID NO: 224 (Chothia/Kabat combined) | HCDR1 | GYTFTTYWMH |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSS |
| SEQ ID NO: 95 | DNA VH | GAGGTGCAGCTGGTGCAGTCAGGCGCCGAAGT GAAGAAGCCCGGCGAGTCACTGAGAATTAGCT GTAAAGGTTCAGGCTACACCTTCACTACCTACT GGATGCACTGGGTCCGCCAGGCTACCGGTCAA GGCCTCGAGTGGATGGGTAATATCTACCCCGG CACCGGCGGCTCTAACTTCGACGAGAAGTTTAA GAATAGAGTGACTATCACCGCCGATAAGTCTAC TAGCACCGCCTATATGGAACTGTCTAGCCTGAG ATCAGAGGACACCGCCGTCTACTACTGCACTAG GTGGACTACCGGCACAGGCGCCTACTGGGGTC AAGGCACTACCGTGACCGTGTCTAGC |
| SEQ ID NO: 91 | HC | EVQLVQSGAEVKKPGESLRISCKGSGYTFTTYWM HWVRQATGQGLEWMGNIYPGTGGSNFDEKFK NRVTITADKSTSTAYMELSSLRSEDTAVYYCTRWT TGTGAYWGQGTTVTVSSASTKGPSVFPLAPCSRS |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | TSESTAALGCLVKDYFPEPVTVSWNSGALTSGVH TFPAVLQSSGLYSLSSVVTVPSSSLGTKTYTCNVD HKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLT VDKSRWQEGNVFSCSVMHEALHNHYTQKSLSLS LG |
| SEQ ID NO: 96 | DNA HC | GAGGTGCAGCTGGTGCAGTCAGGCGCCGAAGT GAAGAAGCCCGGCGAGTCACTGAGAATTAGCT GTAAAGGTTCAGGCTACACCTTCACTACCTACT GGATGCACTGGGTCCGCCAGGCTACCGGTCAA GGCCTCGAGTGGATGGGTAATATCTACCCCGG CACCGGCGGCTCTAACTTCGACGAGAAGTTTAA GAATAGAGTGACTATCACCGCCGATAAGTCTAC TAGCACCGCCTATATGGAACTGTCTAGCCTGAG ATCAGAGGACACCGCCGTCTACTACTGCACTAG GTGGACTACCGGCACAGGCGCCTACTGGGGTC AAGGCACTACCGTGACCGTGTCTAGCGCTAGC ACTAAGGGCCCGTCCGTGTTCCCCCTGGCACCT TGTAGCCGGAGCACTAGCGAATCCACCGCTGC CCTCGGCTGCCTGGTCAAGGATTACTTCCCGGA GCCCGTGACCGTGTCCTGGAACAGCGGAGCCC TGACCTCCGGAGTGCACACCTTCCCCGCTGTGC TGCAGAGCTCCGGGCTGTACTCGCTGTCGTCG GTGGTCACGGTGCCTTCATCTAGCCTGGGTACC AAGACCTACACTTGCAACGTGGACCACAAGCCT TCCAACACTAAGGTGGACAAGCGCGTCGAATC GAAGTACGGCCCACCGTGCCCGCCTTGTCCCGC GCCGGAGTTCCTCGGCGGTCCCTCGGTCTTTCT GTTCCCACCGAAGCCCAAGGACACTTTGATGAT TTCCCGCACCCCTGAAGTGACATGCGTGGTCGT GGACGTGTCACAGGAAGATCCGGAGGTGCAGT TCAATTGGTACGTGGATGGCGTCGAGGTGCAC AACGCCAAAACCAAGCCGAGGGAGGAGCAGTT CAACTCCACTTACCGCGTCGTGTCCGTGCTGAC GGTGCTGCATCAGGACTGGCTGAACGGGAAG GAGTACAAGTGCAAAGTGTCCAACAAGGGACT TCCTAGCTCAATCGAAAAGACCATCTCGAAAGC CAAGGGACAGCCCCGGGAACCCCAAGTGTATA CCCTGCCACCGAGCCAGGAAGAAATGACTAAG AACCAAGTCTCATTGACTTGCCTTGTGAAGGGC TTCTACCCATCGGATATCGCCGTGGAATGGGA GTCCAACGGCCAGCCGGAAAACAACTACAAGA CCACCCCTCCGGTGCTGGACTCAGACGGATCCT TCTTCCTCTACTCGCGGCTGACCGTGGATAAGA GCAGATGGCAGGAGGGAAATGTGTTCAGCTGT TCTGTGATGCATAAGCCCTGCACAACCACTAC ACTCAGAAGTCCCTGTCCCTCTCCCTGGGA |

BAP049-Clone-E LC

| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIK |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 106 | DNA VL | GAGATCGTCCTGACTCAGTCACCCGCTACCCTG AGCCTGAGCCCTGGCGAGCGGGCTACACTGAG CTGTAAATCTAGTCAGTCACTGCTGGATAGCGG TAATCAGAAGAACTTCCTGACCTGGTATCAGCA GAAGCCCGGTCAAGCCCCTAGACTGCTGATCTA CTGGGCCTCTACTAGAGAATCAGGCGTGCCCTC TAGGTTTAGCGGTAGCGGTAGTGGCACCGACT TCACCTTCACTATCTCTAGCCTGGAAGCCGAGG ACGCCGCTACCTACTACTGTCAGAACGACTATA GCTACCCCTACACCTTCGGTCAAGGCACTAAGG TCGAGATTAAG |
|---|---|---|
| SEQ ID NO: 72 | LC | EIVLTQSPATLSLSPGERATLSCKSSQSLLDSGNQK NFLTWYQQKPGQAPRLLIYWASTRESGVPSRFSG SGSGTDFTFTISSLEAEDAATYYCQNDYSYPYTFG QGTKVEIKRTVAAPSVFIFPPSDEQLKSGTASVVC LLNNFYPREAKVQWKVDNALQSGNSQESVTEQ DSKDSTYSLSSTLTLSKADYEKHKVYACEVTHQGL SSPVTKSFNRGEC |
| SEQ ID NO: 107 | DNA LC | GAGATCGTCCTGACTCAGTCACCCGCTACCCTG AGCCTGAGCCCTGGCGAGCGGGCTACACTGAG CTGTAAATCTAGTCAGTCACTGCTGGATAGCGG TAATCAGAAGAACTTCCTGACCTGGTATCAGCA GAAGCCCGGTCAAGCCCCTAGACTGCTGATCTA CTGGGCCTCTACTAGAGAATCAGGCGTGCCCTC TAGGTTTAGCGGTAGCGGTAGTGGCACCGACT TCACCTTCACTATCTCTAGCCTGGAAGCCGAGG ACGCCGCTACCTACTACTGTCAGAACGACTATA GCTACCCCTACACCTTCGGTCAAGGCACTAAGG TCGAGATTAAGCGTACGGTGGCCGCTCCCAGC GTGTTCATCTTCCCCCCCAGCGACGAGCAGCTG AAGAGCGGCACCGCCAGCGTGGTGTGCCTGCT GAACAACTTCTACCCCGGGAGGCCAAGGTGC AGTGGAAGGTGGACAACGCCCTGCAGAGCGG CAACAGCCAGGAGAGCGTCACCGAGCAGGACA GCAAGGACTCCACCTACAGCCTGAGCAGCACC CTGACCCTGAGCAAGGCCGACTACGAGAAGCA TAAGGTGTACGCCTGCGAGGTGACCCACCAGG GCCTGTCCAGCCCCGTGACCAAGAGCTTCAACA GGGGCGAGTGC |

BAP049 HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049 LC

| SEQ ID NO: 113 (Kabat) | LCDR1 | AAGTCCAGTCAGAGTCTGTTAGACAGTGGAAA TCAAAAGAACTTCTTGACC |
|---|---|---|
| SEQ ID NO: 114 (Kabat) | LCDR2 | TGGGCATCCACTAGGGAATCT |
| SEQ ID NO: 115 (Kabat) | LCDR3 | CAGAATGATTATAGTTATCCGTGCACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 118 (Chothia) | LCDR3 | GATTATAGTTATCCGTGC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-chi HC

| | | | |
|---|---|---|---|
| SEQ ID NO: 108 | (Kabat) | HCDR1 | ACTTACTGGATGCAC |
| SEQ ID NO: 109 | (Kabat) | HCDR2 | AATATTTATCCTGGTACTGGTGGTTCTAACTTCG ATGAGAAGTTCAAGAAC |
| SEQ ID NO: 110 | (Kabat) | HCDR3 | TGGACTACTGGGACGGGAGCTTAT |
| SEQ ID NO: 111 | (Chothia) | HCDR1 | GGCTACACATTCACCACTTAC |
| SEQ ID NO: 112 | (Chothia) | HCDR2 | TATCCTGGTACTGGTGGT |
| SEQ ID NO: 110 | (Chothia) | HCDR3 | TGGACTACTGGGACGGGAGCTTAT |

BAP049-chi LC

| | | | |
|---|---|---|---|
| SEQ ID NO: 113 | (Kabat) | LCDR1 | AAGTCCAGTCAGAGTCTGTTAGACAGTGGAAA TCAAAAGAACTTCTTGACC |
| SEQ ID NO: 114 | (Kabat) | LCDR2 | TGGGCATCCACTAGGGAATCT |
| SEQ ID NO: 115 | (Kabat) | LCDR3 | CAGAATGATTATAGTTATCCGTGCACG |
| SEQ ID NO: 116 | (Chothia) | LCDR1 | AGTCAGAGTCTGTTAGACAGTGGAAATCAAAA GAACTTC |
| SEQ ID NO: 117 | (Chothia) | LCDR2 | TGGGCATCC |
| SEQ ID NO: 118 | (Chothia) | LCDR3 | GATTATAGTTATCCGTGC |

BAP049-chi Y HC

| | | | |
|---|---|---|---|
| SEQ ID NO: 108 | (Kabat) | HCDR1 | ACTTACTGGATGCAC |
| SEQ ID NO: 109 | (Kabat) | HCDR2 | AATATTTATCCTGGTACTGGTGGTTCTAACTTCG ATGAGAAGTTCAAGAAC |
| SEQ ID NO: 110 | (Kabat) | HCDR3 | TGGACTACTGGGACGGGAGCTTAT |
| SEQ ID NO: 111 | (Chothia) | HCDR1 | GGCTACACATTCACCACTTAC |
| SEQ ID NO: 112 | (Chothia) | HCDR2 | TATCCTGGTACTGGTGGT |
| SEQ ID NO: 110 | (Chothia) | HCDR3 | TGGACTACTGGGACGGGAGCTTAT |

BAP049-chi Y LC

| | | | |
|---|---|---|---|
| SEQ ID NO: 113 | (Kabat) | LCDR1 | AAGTCCAGTCAGAGTCTGTTAGACAGTGGAAA TCAAAAGAACTTCTTGACC |
| SEQ ID NO: 114 | (Kabat) | LCDR2 | TGGGCATCCACTAGGGAATCT |
| SEQ ID NO: 119 | (Kabat) | LCDR3 | CAGAATGATTATAGTTATCCGTACACG |
| SEQ ID NO: 116 | (Chothia) | LCDR1 | AGTCAGAGTCTGTTAGACAGTGGAAATCAAAA GAACTTC |
| SEQ ID NO: 117 | (Chothia) | LCDR2 | TGGGCATCC |
| SEQ ID NO: 120 | (Chothia) | LCDR3 | GATTATAGTTATCCGTAC |

BAP049-hum01 HC

| | | | |
|---|---|---|---|
| SEQ ID NO: 108 | (Kabat) | HCDR1 | ACTTACTGGATGCAC |
| SEQ ID NO: 109 | (Kabat) | HCDR2 | AATATTTATCCTGGTACTGGTGGTTCTAACTTCG ATGAGAAGTTCAAGAAC |
| SEQ ID NO: 110 | (Kabat) | HCDR3 | TGGACTACTGGGACGGGAGCTTAT |
| SEQ ID NO: 111 | (Chothia) | HCDR1 | GGCTACACATTCACCACTTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum01 LC

| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum02 HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum02 LC

| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum03 HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum03 LC

| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 116 (Chothia) | LCDR1 | AGTCAGAGTCTGTTAGACAGTGGAAATCAAAAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum04 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum04 LC

| | | |
|---|---|---|
| SEQ ID NO: 113 (Kabat) | LCDR1 | AAGTCCAGTCAGAGTCTGTTAGACAGTGGAAATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum05 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum05 LC

| | | |
|---|---|---|
| SEQ ID NO: 113 (Kabat) | LCDR1 | AAGTCCAGTCAGAGTCTGTTAGACAGTGGAAATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-hum06 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum06 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum07 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum07 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum08 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum08 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum09 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum09 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum10 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum10 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |
| BAP049-hum11 HC | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| BAP049-hum11 LC | | |
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |
| BAP049-hum12 HC | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| BAP049-hum12 LC | | |
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | | |
|---|---|---|---|
| BAP049-hum13 HC | | | |
| SEQ ID NO: 108 (Kabat) | | HCDR1 | ACTTACTGGATGCAC |
| SEQ ID NO: 109 (Kabat) | | HCDR2 | AATATTTATCCTGGTACTGGTGGTTCTAACTTCG ATGAGAAGTTCAAGAAC |
| SEQ ID NO: 110 (Kabat) | | HCDR3 | TGGACTACTGGGACGGGAGCTTAT |
| SEQ ID NO: 111 (Chothia) | | HCDR1 | GGCTACACATTCACCACTTAC |
| SEQ ID NO: 112 (Chothia) | | HCDR2 | TATCCTGGTACTGGTGGT |
| SEQ ID NO: 110 (Chothia) | | HCDR3 | TGGACTACTGGGACGGGAGCTTAT |
| BAP049-hum13 LC | | | |
| SEQ ID NO: 121 (Kabat) | | LCDR1 | AAGTCCAGTCAGAGTCTGTTAGACAGTGGAAA TCAAAAGAACTTCTTAACC |
| SEQ ID NO: 114 (Kabat) | | LCDR2 | TGGGCATCCACTAGGGAATCT |
| SEQ ID NO: 119 (Kabat) | | LCDR3 | CAGAATGATTATAGTTATCCGTACACG |
| SEQ ID NO: 116 (Chothia) | | LCDR1 | AGTCAGAGTCTGTTAGACAGTGGAAATCAAAA GAACTTC |
| SEQ ID NO: 117 (Chothia) | | LCDR2 | TGGGCATCC |
| SEQ ID NO: 120 (Chothia) | | LCDR3 | GATTATAGTTATCCGTAC |
| BAP049-hum14 HC | | | |
| SEQ ID NO: 108 (Kabat) | | HCDR1 | ACTTACTGGATGCAC |
| SEQ ID NO: 109 (Kabat) | | HCDR2 | AATATTTATCCTGGTACTGGTGGTTCTAACTTCG ATGAGAAGTTCAAGAAC |
| SEQ ID NO: 223 (Kabat) | | HCDR3 | TGGACTACTGGGACGGGAGCTTAC |
| SEQ ID NO: 111 (Chothia) | | HCDR1 | GGCTACACATTCACCACTTAC |
| SEQ ID NO: 112 (Chothia) | | HCDR2 | TATCCTGGTACTGGTGGT |
| SEQ ID NO: 223 (Chothia) | | HCDR3 | TGGACTACTGGGACGGGAGCTTAC |
| BAP049-hum14 LC | | | |
| SEQ ID NO: 113 (Kabat) | | LCDR1 | AAGTCCAGTCAGAGTCTGTTAGACAGTGGAAA TCAAAAGAACTTCTTGACC |
| SEQ ID NO: 114 (Kabat) | | LCDR2 | TGGGCATCCACTAGGGAATCT |
| SEQ ID NO: 119 (Kabat) | | LCDR3 | CAGAATGATTATAGTTATCCGTACACG |
| SEQ ID NO: 116 (Chothia) | | LCDR1 | AGTCAGAGTCTGTTAGACAGTGGAAATCAAAA GAACTTC |
| SEQ ID NO: 117 (Chothia) | | LCDR2 | TGGGCATCC |
| SEQ ID NO: 120 (Chothia) | | LCDR3 | GATTATAGTTATCCGTAC |
| BAP049-hum15 HC | | | |
| SEQ ID NO: 108 (Kabat) | | HCDR1 | ACTTACTGGATGCAC |
| SEQ ID NO: 109 (Kabat) | | HCDR2 | AATATTTATCCTGGTACTGGTGGTTCTAACTTCG ATGAGAAGTTCAAGAAC |
| SEQ ID NO: 223 (Kabat) | | HCDR3 | TGGACTACTGGGACGGGAGCTTAC |
| SEQ ID NO: 111 (Chothia) | | HCDR1 | GGCTACACATTCACCACTTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 112 (Chothia) | HCDR2 | TATCCTGGTACTGGTGGT |
| SEQ ID NO: 223 (Chothia) | HCDR3 | TGGACTACTGGGACGGGAGCTTAC |

BAP049-hum15 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum16 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTCG ATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum16 LC

| | | |
|---|---|---|
| SEQ ID NO: 113 (Kabat) | LCDR1 | AAGTCCAGTCAGAGTCTGTTAGACAGTGGAAA TCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAA GAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-Clone-A HC

| | | |
|---|---|---|
| SEQ ID NO: 122 (Kabat) | HCDR1 | ACCTACTGGATGCAC |
| SEQ ID NO: 123 (Kabat) | HCDR2 | AACATCTATCCTGGCACCGGCGGCTCCAACTTC GACGAGAAGTTCAAGAAC |
| SEQ ID NO: 124 (Kabat) | HCDR3 | TGGACAACCGGCACAGGCGCTTAT |
| SEQ ID NO: 125 (Chothia) | HCDR1 | GGCTACACCTTCACCACCTAC |
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |

BAP049-Clone-A LC

| | | |
|---|---|---|
| SEQ ID NO: 127 (Kabat) | LCDR1 | AAGTCCTCCCAGTCCCTGCTGGACTCCGGCAAC CAGAAGAACTTCCTGACC |
| SEQ ID NO: 128 (Kabat) | LCDR2 | TGGGCCTCCACCCGGGAATCT |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAGAACTTC |
| SEQ ID NO: 131 (Chothia) | LCDR2 | TGGGCCTCC |
| SEQ ID NO: 132 (Chothia) | LCDR3 | GACTACTCCTACCCCTAC |

BAP049-Clone-B HC

| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAACTTCGACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-B LC

| SEQ ID NO: 138 (Kabat) | LCDR1 | AAATCTAGTCAGTCACTGCTGGATAGCGGTAATCAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAGAAGAACTTC |
| SEQ ID NO: 142 (Chothia) | LCDR2 | TGGGCCTCT |
| SEQ ID NO: 143 (Chothia) | LCDR3 | GACTATAGCTACCCCTAC |

BAP049-Clone-C HC

| SEQ ID NO: 122 (Kabat) | HCDR1 | ACCTACTGGATGCAC |
| SEQ ID NO: 123 (Kabat) | HCDR2 | AACATCTATCCTGGCACCGGCGGCTCCAACTTCGACGAGAAGTTCAAGAAC |
| SEQ ID NO: 124 (Kabat) | HCDR3 | TGGACAACCGGCACAGGCGCTTAT |
| SEQ ID NO: 125 (Chothia) | HCDR1 | GGCTACACCTTCACCACCTAC |
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |

BAP049-Clone-C LC

| SEQ ID NO: 127 (Kabat) | LCDR1 | AAGTCCTCCCAGTCCCTGCTGGACTCCGGCAACCAGAAGAACTTCCTGACC |
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAGAACTTC |
| SEQ ID NO: 131 (Chothia) | LCDR2 | TGGGCCTCC |
| SEQ ID NO: 132 (Chothia) | LCDR3 | GACTACTCCTACCCCTAC |

TABLE B-continued

Amino acid and nucleotide sequences for murine, chimeric and humanized PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-Clone-D HC

| | | |
|---|---|---|
| SEQ ID NO: 122 (Kabat) | HCDR1 | ACCTACTGGATGCAC |
| SEQ ID NO: 144 (Kabat) | HCDR2 | AACATCTACCCTGGCACCGGCGGCTCCAACTTC GACGAGAAGTTCAAGAAC |
| SEQ ID NO: 145 (Kabat) | HCDR3 | TGGACCACCGGAACCGGCGCCTAT |
| SEQ ID NO: 125 (Chothia) | HCDR1 | GGCTACACCTTCACCACCTAC |
| SEQ ID NO: 146 (Chothia) | HCDR2 | TACCCTGGCACCGGCGGC |
| SEQ ID NO: 145 (Chothia) | HCDR3 | TGGACCACCGGAACCGGCGCCTAT |

BAP049-Clone-D LC

| | | |
|---|---|---|
| SEQ ID NO: 127 (Kabat) | LCDR1 | AAGTCCTCCCAGTCCCTGCTGGACTCCGGCAAC CAGAAGAACTTCCTGACC |
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAG AACTTC |
| SEQ ID NO: 131 (Chothia) | LCDR2 | TGGGCCTCC |
| SEQ ID NO: 132 (Chothia) | LCDR3 | GACTACTCCTACCCCTAC |

BAP049-Clone-E HC

| | | |
|---|---|---|
| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAACTTC GACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-E LC

| | | |
|---|---|---|
| SEQ ID NO: 138 (Kabat) | LCDR1 | AAATCTAGTCAGTCACTGCTGGATAGCGGTAAT CAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAGAA GAACTTC |
| SEQ ID NO: 142 (Chothia) | LCDR2 | TGGGCCTCT |
| SEQ ID NO: 143 (Chothia) | LCDR3 | GACTATAGCTACCCCTAC |

TABLE C

Amino acid and nucleotide sequences of the heavy and light chain framework regions for humanized anti-PD-1 mAbs BAP049-hum01 to BAP049-hum16 and BAP049-Clone-A to BAP049-Clone-E

| | Amino Acid Sequence | Nucleotide Sequence |
|---|---|---|
| VHFW1 (type a) | EVQLVQSGAEVKKPGESLRISCKGS (SEQ ID NO: 147) | GAAGTGCAGCTGGTGCAGTCTGGAGCAGAGGTGAAA AAGCCCGGGGAGTCTCTGAGGATCTCCTGTAAGGGTT CT (SEQ ID NO: 148) |
| | | GAAGTGCAGCTGGTGCAGTCTGGCGCCGAAGTGAAG AAGCCTGGCGAGTCCCTGCGGATCTCCTGCAAGGGCT CT (SEQ ID NO: 149) |
| | | GAGGTGCAGCTGGTGCAGTCAGGCGCCGAAGTGAAG AAGCCCGGCGAGTCACTGAGAATTAGCTGTAAAGGTT CA (SEQ ID NO: 150) |
| VHFW1 (type b) | QVQLVQSGAEVKKPGASVKVSCKAS (SEQ ID NO: 151) | CAGGTTCAGCTGGTGCAGTCTGGAGCTGAGGTGAAGA AGCCTGGGGCCTCAGTGAAGGTCTCCTGCAAGGCTTC T (SEQ ID NO: 152) |
| VHFW2 (type a) | WVRQATGQGLEWMG (SEQ ID NO: 153) | TGGGTGCGACAGGCCACTGGACAAGGGCTTGAGTGG ATGGGT (SEQ ID NO: 154) |
| | | TGGGTGCGACAGGCTACCGGCCAGGGCCTGGAATGG ATGGG (SEQ ID NO: 155) |
| | | TGGGTCCGCCAGGCTACCGGTCAAGGCCTCGAGTGGA TGGGT (SEQ ID NO: 156) |
| VHFW2 (type b) | WIRQSPSRGLEWLG (SEQ ID NO: 157) | TGGATCAGGCAGTCCCCATCGAGAGGCCTTGAGTGGC TGGGT (SEQ ID NO: 158) |
| | | TGGATCCGGCAGTCCCCCTCTAGGGGCCTGGAATGGC TGGGC (SEQ ID NO: 159) |
| VHFW2 (type c) | WVRQAPGQGLEWMG (SEQ ID NO: 160) | TGGGTGCGACAGGCCCCTGGACAAGGGCTTGAGTGG ATGGGT (SEQ ID NO: 161) |
| VHFW3 (type a) | RVTITADKSTSTAYMELSSLRSEDTAVYYC TR (SEQ ID NO: 162) | AGAGTCACGATTACCGCGGACAAATCCACGAGCACAG CCTACATGGAGCTGAGCAGCCTGAGATCCGAGGACAC GGCCGTGTATTACTGTACAAGA (SEQ ID NO: 163) |
| | | AGAGTGACCATCACCGCCGACAAGTCCACCTCCACCG CCTACATGGAACTGTCCTCCCTGAGATCCGAGGACACC GCCGTGTACTACTGCACCCGG (SEQ ID NO: 164) |
| | | AGAGTGACTATCACCGCCGATAAGTCTACTAGCACCG CCTATATGGAACTGTCTAGCCTGAGATCAGAGGACAC CGCCGTCTACTACTGCACTAGG (SEQ ID NO: 165) |
| VHFW3 (type b) | RFTISRDNSKNTLYLQMNSLRAEDTAVYY CTR (SEQ ID NO: 166) | AGATTCACCATCTCCAGAGACAATTCCAAGAACACGCT GTATCTTCAAATGAACAGCCTGAGAGCCGAGGACACG GCCGTGTATTACTGTACAAGA (SEQ ID NO: 167) |
| | | AGGTTCACCATCTCCCGGGACAACTCCAAGAACACCCT GTACCTGCAGATGAACTCCCTGCGGGCCGAGGACACC GCCGTGTACTACTGTACCAGA (SEQ ID NO: 168) |
| VHFW4 | WGQGTTVTVSS (SEQ ID NO: 169) | TGGGGCCAGGGCACCACCGTGACCGTGTCCTCC (SEQ ID NO: 170) |
| | | TGGGGCCAGGGCACCACAGTGACCGTGTCCTCT (SEQ ID NO: 171) |
| | | TGGGGTCAAGGCACTACCGTGACCGTGTCTAGC (SEQ ID NO: 172) |
| | | TGGGGCCAGGGCACAACAGTGACCGTGTCCTCC (SEQ ID NO: 173) |
| VLFW1 (type a) | EIVLTQSPDFQSVTPKEKVTITC (SEQ ID NO: 174) | GAAATTGTGCTGACTCAGTCTCCAGACTTTCAGTCTGT GACTCCAAAGGAGAAAGTCACCATCACCTGC (SEQ ID NO: 175) |
| | | GAGATCGTGCTGACCCAGTCCCCCGACTTCCAGTCCGT GACCCCCAAAGAAAAAGTGACCATCACATGC (SEQ ID NO: 176) |

TABLE C-continued

Amino acid and nucleotide sequences of the heavy and light chain framework regions for humanized anti-PD-1 mAbs BAP049-hum01 to BAP049-hum16 and BAP049-Clone-A to BAP049-Clone-E

| | Amino Acid Sequence | Nucleotide Sequence |
|---|---|---|
| VLFW1 (type b) | EIVLTQSPATLSLSPGERATLSC (SEQ ID NO: 177) | GAAATTGTGTTGACACAGTCTCCAGCCACCCTGTCTTT GTCTCCAGGGGAAAGAGCCACCCTCTCCTGC (SEQ ID NO: 178) |
| | | GAGATCGTGCTGACCCAGTCCCCTGCCACCCTGTCACT GTCTCCAGGCGAGAGAGCCACCCTGTCCTGC (SEQ ID NO: 179) |
| | | GAGATCGTCCTGACTCAGTCACCCGCTACCCTGAGCCT GAGCCCTGGCGAGCGGGCTACACTGAGCTGT (SEQ ID NO: 180) |
| VLFW1 (type c) | DIVMTQTPLSLPVTPGEPASISC (SEQ ID NO: 181) | GATATTGTGATGACCCAGACTCCACTCTCCCTGCCCGT CACCCCTGGAGAGCCGGCCTCCATCTCCTGC (SEQ ID NO: 182) |
| VLFW1 (type d) | DVVMTQSPLSLPVTLGQPASISC (SEQ ID NO: 183) | GATGTTGTGATGACTCAGTCTCCACTCTCCCTGCCCGT CACCCTTGGACAGCCGGCCTCCATCTCCTGC (SEQ ID NO: 184) |
| VLFW1 (type e) | DIQMTQSPSSLSASVGDRVTITC (SEQ ID NO: 185) | GACATCCAGATGACCCAGTCTCCATCCTCCCTGTCTGC ATCTGTAGGAGACAGAGTCACCATCACTTGC (SEQ ID NO: 186) |
| VLFW2 (type a) | WYQQKPGQAPRLLIY (SEQ ID NO: 187) | TGGTACCAGCAGAAACCTGGCCAGGCTCCCAGGCTCC TCATCTAT (SEQ ID NO: 188) |
| | | TGGTATCAGCAGAAGCCCGGCCAGGCCCCCAGACTGC TGATCTAC (SEQ ID NO: 189) |
| | | TGGTATCAGCAGAAGCCCGGTCAAGCCCCTAGACTGC TGATCTAC (SEQ ID NO: 190) |
| VLFW2 (type b) | WYQQKPGKAPKLLIY (SEQ ID NO: 191) | TGGTATCAGCAGAAACCAGGGAAAGCTCCTAAGCTCC TGATCTAT (SEQ ID NO: 192) |
| | | TGGTATCAGCAGAAGCCCGGTAAAGCCCCTAAGCTGC TGATCTAC (SEQ ID NO: 193) |
| VLFW2 (type c) | WYLQKPGQSPQLLIY (SEQ ID NO: 194) | TGGTACCTGCAGAAGCCAGGGCAGTCTCCACAGCTCC TGATCTAT (SEQ ID NO: 195) |
| VLFW3 (type a) | GVPSRFSGSGSGTDFTFTISSLEAEDAATY YC (SEQ ID NO: 196) | GGGGTCCCCTCGAGGTTCAGTGGCAGTGGATCTGGGA CAGATTTCACCTTTACCATCAGTAGCCTGGAAGCTGAA GATGCTGCAACATATTACTGT (SEQ ID NO: 197) |
| | | GGCGTGCCCTCTAGATTCTCCGGCTCCGGCTCTGGCAC CGACTTTACCTTCACCATCTCCAGCCTGGAAGCCGAGG ACGCCGCCACCTACTACTGC (SEQ ID NO: 198) |
| | | GGCGTGCCCTCTAGGTTTAGCGGTAGCGGTAGTGGCA CCGACTTCACCTTCACTATCTCTAGCCTGGAAGCCGAG GACGCCGCTACCTACTACTGT (SEQ ID NO: 199) |
| VLFW3 (type b) | GIPPRFSGSGYGTDFTLTINNIESEDAAYY FC (SEQ ID NO: 200) | GGGATCCCACCTCGATTCAGTGGCAGCGGGTATGGAA CAGATTTTACCCTCACAATTAATAACATAGAATCTGAG GATGCTGCATATTACTTCTGT (SEQ ID NO: 201) |
| VLFW3 (type c) | GVPSRFSGSGSGTEFTLTISSLQPDDFATY YC (SEQ ID NO: 202) | GGGGTCCCATCAAGGTTCAGCGGCAGTGGATCTGGGA CAGAATTCACTCTCACCATCAGCAGCCTGCAGCCTGAT GATTTTGCAACTTATTACTGT (SEQ ID NO: 203) |
| | | GGCGTGCCCTCTAGATTCTCCGGCTCCGGCTCTGGCAC CGAGTTTACCCTGACCATCTCCAGCCTGCAGCCCGACG ACTTCGCCACCTACTACTGC (SEQ ID NO: 204) |
| VLFW3 (type d) | GVPSRFSGSGSGTDFTFTISSLQPEDIATY YC (SEQ ID NO: 205) | GGGGTCCCATCAAGGTTCAGTGGAAGTGGATCTGGGA CAGATTTTACTTTCACCATCAGCAGCCTGCAGCCTGAA GATATTGCAACATATTACTGT (SEQ ID NO: 206) |
| | | GGCGTGCCCTCTAGGTTTAGCGGTAGCGGTAGTGGCA CCGACTTCACCTTCACTATCTCTAGCCTGCAGCCCGAG GATATCGCTACCTACTACTGT (SEQ ID NO: 207) |

TABLE C-continued

Amino acid and nucleotide sequences of the heavy and light chain framework regions for humanized anti-PD-1 mAbs BAP049-hum01 to BAP049-hum16 and BAP049-Clone-A to BAP049-Clone-E

| | Amino Acid Sequence | Nucleotide Sequence |
|---|---|---|
| VLFW4 | FGQGTKVEIK (SEQ ID NO: 208) | TTCGGCCAAGGGACCAAGGTGGAAATCAAA (SEQ ID NO: 209) |
| | | TTCGGCCAGGGCACCAAGGTGGAAATCAAG (SEQ ID NO: 210) |
| | | TTCGGTCAAGGCACTAAGGTCGAGATTAAG (SEQ ID NO: 211) |

TABLE D

Constant region amino acid sequences of human IgG heavy chains and human kappa light chain HC IgG4 (S228P) mutant constant region amino acid sequence (EU Numbering)
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK (SEQ ID NO: 212)

LC Human kappa constant region amino acid sequence
RTVAAPSVFI FPPSDEQLKS GTASVVCLLN NFYPREAKVQ WKVDNALQSG NSQESVTEQD
SKDSTYSLSS TLTLSKADYE KHKVYACEVT HQGLSSPVTK
SFNRGEC (SEQ ID NO: 213)

HC IgG4 (S228P) mutant constant region amino acid sequence lacing C-terminal lysine (K) (EU Numbering)
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLG (SEQ ID NO: 214)

HC IgG1 wild type
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG
PSVFLFPPKP KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 215)

HC IgG1 (N297A) mutant constant region amino acid sequence (EU Numbering)
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG
PSVFLFPPKP KDTLMISRTP EVTCVVVDVS HEDPEVKFNW YVDGVEVHNA KTKPREEQYA
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 216)

HC IgG1 (D265A, P329A) mutant constant region amino acid sequence (EU Numbering)
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG
PSVFLFPPKP KDTLMISRTP EVTCVVVAVS HEDPEVKFNW YVDGVEVHNA KTKPREEQYN
STYRVVSVLT VLHQDWLNGK EYKCKVSNKA LAAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 217)

HC IgG1 (I234A, I235A) mutant constant region amino acid sequence (EU Numbering)
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPEAAGG
PSVFLFPPKP KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 218)

Therapeutic Kits

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of Formula I and the other immunotherapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating cancer, wherein the medicament is prepared for administration with another immunotherapeutic agent. The invention also provides the use of an immunotherapeutic agent for treating cancer, wherein the medicament is administered with a compound of formula (I).

The invention also provides a compound of formula (I) for use in a method of treating cancer, wherein the compound of formula (I) is prepared for administration with another immunotherapeutic agent. The invention also provides another immunotherapeutic agent for use in a method of treating cancer, wherein the other immunotherapeutic agent is prepared for administration with a compound of formula (I). The invention also provides a compound of formula (I) for use in a method of treating cancer, wherein the compound of formula (I) is administered with another immunotherapeutic agent. The invention also provides another immunotherapeutic agent for use in a method of treating cancer, wherein the other therapeutic agent is administered with a compound of formula (I).

The invention also provides the use of a compound of formula (I) for treating cancer, wherein the patient has previously (e.g. within 24 hours) been treated with another immunotherapeutic agent. The invention also provides the use of another immunotherapeutic agent for treating cancer, wherein the patient has previously (e.g. within 24 hours) been treated with a compound of formula (I).

Pharmaceutical Composition, Combination, Dosage and Administration

In one embodiment, pharmaceutical composition comprises an effective amount of compound of formula (I) or a pharmaceutically acceptable salt or co-crystal thereof and a pharmaceutically acceptable vehicle or carrier.

In another embodiment, the invention pertains to a pharmaceutical combination, comprising a therapeutically acceptable amount of a compound of Formula (I), or a pharmaceutically acceptable salt thereof, and one or more immunotherapeutically active agent, for the manufacture of a medicament for treating cancer.

In one embodiment, the composition comprises at least two pharmaceutically acceptable carriers, such as those described herein. Preferably, pharmaceutically acceptable carriers are sterile. The pharmaceutical composition can be formulated for particular routes of administration such as oral administration, parenteral administration, and rectal administration, intravenous administration etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

In a preferred embodiment, the compound of formula (I) or pharmaceutically acceptable salt or co-crystals thereof for use in the treatment of cancer are for administration by parenteral or oral route, preferably by oral route.

The pharmaceutical composition or combination of the present invention can be in unit dosage of about 1-1000 mg of active ingredient(s) for a subject of about 50-70 kg, or about 1-650 mg or about 1-350 mg or about 1-200 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention (Compound of Formula I) can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg, or between 1-10 mg/Kg. In certain embodiment, the compound of Formula I is administered orally at a dose of about 1 to 30 mg/kg, e.g., about 1 to 25 mg/kg, about 1 to 20 mg/kg, about 1 to 6 mg/kg. The dosing schedule can vary from e.g., once a day to twice a day. In one embodiment, the compound of Formula I is administered at a dose from about 80 mg, 160 mg, 320 mg or 640 mg twice a day for a subject of about 50-70 Kg.

Dosage and Administration of the Immunotherapeutic Agent.

The immunotherapeutic agent (Such as an anti-PD-1 antibody molecule or an anti-PD-L1 molecule antibody) can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the immunotherapeutic agent (e.g. anti-PD-1 antibody molecule or anti PD-L1 antibody molecule) can be determined by a skilled artisan. In certain embodiments, the immunotherapeutic agent (e.g. anti-PD-1 antibody molecule) is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. In another embodiment, the anti-PD-1 antibody molecule is administered at a dose from about 1 to 10 mg/Kg, or from about 1 to 5 mg/Kg or about 3 mg/kg every 4 weeks.

For example, the anti-PD-1 antibody molecule is administered or used at a flat or fixed dose. In some embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

In another embodiment, the anti-PD-1 antibody molecule is administered at a flat dose of about 300 mg to 400 mg once every three weeks or once every four weeks. In a subset of this embodiment, the anti-PD-1 antibody molecule is administered at a flat dose of about 400 mg every four weeks. In yet another subset of this embodiment, the anti-PD-1 antibody molecule is administered at a flat dose of about 300 mg every three weeks.

In one embodiment of the present invention the compound of formula (I), its pharmaceutically acceptable salts or its co-crystals and the immunotherapeutic agents useful in the treatment of cancer form part of the same composition.

In another embodiment of the present invention the compound of formula (I), its pharmaceutically acceptable salts or its co-crystals and the immunotherapeutic agents useful in the treatment of cancer form part of separate compositions for administration simultaneously or sequentially.

In one embodiment, the compound of Formula I may be administered either simultaneously with, or before or after, one or more immunotherapeutic agents (e.g. anti CTLA4 antibodies, anti-PD-1 antibodies and anti-PD-L1 antibodies). The compound of Formula I may be administered separately, by the same or different route of administration, or together in the same pharmaceutical composition as the immunotherapeutic agents. A preferred immunotherapeutic agent is, for example, an antibody, which is therapeutically active or enhances the therapeutic activity when administered to a patient in combination with a compound of Formula I.

In yet another embodiment, the compound of Formula (I) and the immunotherapeutic agent can be administered simultaneously or sequentially in any order. Any combination and sequence of the compound of Formula (I) and the immunotherapeutic agent (e.g., as described herein) can be used. The compound of Formula (I) and/or immunotherapeutic agent can be administered during periods of active disorder, or during a period of remission or less active disease. The immunotherapeutic agent can be administered before the treatment with compound of Formula (I), concurrently with the treatment, post-treatment, or during remission of the disorder.

In a preferred embodiment, the compound of Formula I is administered (fasting) twice daily, prior to the administration of the immunotherapeutic agent (for example an anti-PD-1 antibody molecule as described herein).

In one embodiment, the invention provides a product comprising a compound of formula (I) and at least one other immunotherapeutic agent as a combined preparation for simultaneous, separate or sequential use in therapy. In one embodiment, the therapy is the treatment of a disease or condition mediated by the $A_2a$ receptor. Products provided as a combined preparation include a composition comprising the compound of formula (I) and the immunotherapeutic agent(s) together in the same pharmaceutical composition, or the compound of formula (I) and the other therapeutic agent(s) (e.g. anti CTLA4 antibodies, anti-PD-1 antibodies and anti-PD-L1 antibodies in separate form), e.g. in the form of a kit.

In one embodiment, the invention provides a pharmaceutical composition comprising a compound of formula (I) and the immunotherapeutic agent(s) (e.g. anti CTLA4 antibodies, anti-PD-1 antibodies and anti-PD-L1 antibodies). Optionally, the pharmaceutical composition may comprise a pharmaceutically acceptable carrier, as described above.

Enumerated Embodiments of the Invention are Described Below

1—Compound of formula (I)

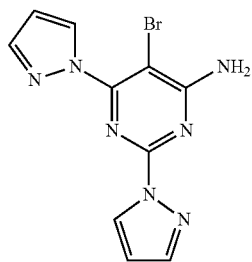

(I)

or a pharmaceutically acceptable salt or co-crystal thereof, for use in the treatment of cancer.

2—Compound for use according to embodiment 1 wherein the cancer is lung cancer.

3—Compound for use according to embodiment 2 wherein the lung cancer is non-small cell lung cancer.

4—Compound for use according to any one of embodiments 1 to 3 wherein said compound is administered by parenteral or oral route.

5—Compound for use according to embodiment 4 wherein said compound is administered by oral route.

6—A combination product comprising a therapeutically effective amount of a compound of formula (I) or a pharmaceutically acceptable salt or co-crystal thereof and one or more immunotherapeutic agents selected from the group consisting of an anti-CTLA4 antibody, an anti-PD-1 antibody and an anti-PD-L1 antibody.

7—The combination as defined in embodiment 6 for use in the treatment of cancer.

8. The combination for use according to embodiment 7 wherein cancer is lung cancer.

9—The combination for use according to embodiment 8 wherein lung cancer is non-small cell lung cancer.

10—The combination for use according to any one of embodiments 6 to 9 wherein the immunotherapeutic agent is selected from the group consisting of ipilimumab, tremelimumab, nivolumab, pembrolizumab, CT-011, AMP-224, MPDL3280A, MED14736 and MDX-1105.

11—Combination for use according to embodiment 10 wherein immunotherapeutic agent is selected from the group consisting of MPDL3280A, MED14736 and MDX-1105.

12—Combination for use according to embodiment 10 wherein immunotherapeutic agent is selected from the group consisting of nivolumab, pembrolizumab, pidilizumab and AMP-224.

13—The combination for use according to embodiment 6 wherein the immunotherapeutic agent is an anti-PD-1 antibody.

14—The combination for use according to embodiment 13 wherein the anti PD-1 antibody comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, 15—The combination for use according to embodiment 13 wherein the anti-PD-1 antibody comprises:

(a) a heavy chain variable domain comprising the amino acid sequence of SEQ ID NO: 91 and a light chain variable domain comprising the amino acid sequence of SEQ ID NO: 72.

16—A combination for use according to any one of embodiments 13 to 15 wherein the anti-PD-1 antibody molecule is administered at a dose of about 300 mg once every three weeks 17—A combination for use according to any one of embodiments 13 to 15 wherein the anti-PD-1 antibody molecule is administered at a dose of about 400 mg once every four weeks.

18—The combination for use according to embodiment 6 wherein the immunotherapeutic agent is an anti-PD-L1 antibody.

19—The combination for use according to embodiment 18 wherein the anti PD-L1 antibody molecule comprises:

(a) a heavy chain variable region (VH) comprising a VHCDR1 amino acid sequence of SEQ ID NO: 228, a VHCDR2 amino acid sequence of SEQ ID NO: 229, and a VHCDR3 amino acid sequence of SEQ ID NO: 227; and a light chain variable region (VL) comprising a VLCDR1 amino acid sequence of SEQ ID NO: 233, a VLCDR2 amino acid sequence of SEQ ID NO: 234, and a VLCDR3 amino acid sequence of SEQ ID NO: 235;

(b) a VH comprising a VHCDR1 amino acid sequence of SEQ ID NO: 225; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232;

(c) a VH comprising a VHCDR1 amino acid sequence of SEQ ID NO: 244, a VHCDR2 amino acid sequence of SEQ ID NO: 229, and a VHCDR3 amino acid sequence of SEQ ID NO: 227; and a VL comprising a VLCDR1 amino acid sequence of SEQ ID NO: 233, a VLCDR2 amino acid sequence of SEQ ID NO: 234, and a VLCDR3 amino acid sequence of SEQ ID NO: 235; or (d) a VH comprising a VHCDR1 amino acid sequence of SEQ ID NO: 244; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232.

20—The combination for use according to embodiment 18 wherein the anti-PD-L1 antibody molecule comprises a heavy chain variable domain comprising the amino acid sequence of SEQ ID NO: 236 and a light chain variable domain comprising the amino acid sequence of SEQ ID NO: 239.

21—A pharmaceutical composition comprising a compound of formula (I) or a pharmaceutically acceptable salt or co-crystal thereof and a pharmaceutically acceptable vehicle or carrier for use in the treatment of cancer.

22—Composition for use according to embodiment 21 wherein the cancer is lung cancer.

23—Composition for use according to embodiment 22 wherein lung cancer is non-small cell lung cancer.

24—Use of a compound of formula (I)

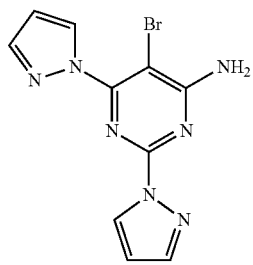

(I)

or a pharmaceutically acceptable salt or co-crystal thereof, for the manufacture of a medicament for treating cancer.

25—Use according to embodiment 24 wherein the cancer is lung cancer.

26—Use according to embodiment 25 wherein the lung cancer is non-small cell lung cancer.

27—Use according to any one of embodiments 24 to 26 wherein said compound is administered by parenteral or oral route.

28—Use according to embodiment 27 wherein said compound is administered by oral route.

29—Use of combination product comprising a therapeutically effective amount of a compound of formula (I) or a pharmaceutically acceptable salt or co-crystal thereof and one or more immunotherapeutic agents selected from the group consisting of an anti-CTLA4 antibody, an anti-PD-1 antibody and an anti-PD-L1 antibody, for the manufacture of a medicament for treating cancer.

30—Use according to embodiment 29 wherein cancer is lung cancer.

31—Use according to embodiment 30 wherein lung cancer is non-small cell lung cancer.

32—Use according to any one of embodiments 29 to 31 wherein the immunotherapeutic agent is selected from the group consisting of ipilimumab, tremelimumab, nivolumab, pembrolizumab, CT-011, AMP-224, MPDL3280A, MED14736 and MDX-1105.

33—Use according to embodiment 32 wherein immunotherapeutic agent is selected from the group consisting of MPDL3280A, MED14736 and MDX-1105.

34—Use according to embodiment 32 wherein immunotherapeutic agent is selected from the group consisting of nivolumab, pembrolizumab, pidilizumab and AMP-224.

35—Use according to embodiment 29 wherein the immunotherapeutic agent is an anti-PD-1 antibody.

36—Use according to embodiment 35 wherein the anti PD-1 antibody comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, 37—Use according to embodiment 35 wherein the anti-PD-1 antibody comprises:

(a) a heavy chain variable domain comprising the amino acid sequence of SEQ ID NO: 91 and a light chain variable domain comprising the amino acid sequence of SEQ ID NO: 72.

38—Use according to any one of embodiments 35 to 37 wherein the anti-PD-1 antibody molecule is administered at a dose of about 300 mg once every three weeks 39—Use according to any one of embodiments 35 to 37 wherein the anti-PD-1 antibody molecule is administered at a dose of about 400 mg once every four weeks 40—Use according to embodiment 29 wherein the immunotherapeutic agent is an anti-PD-L1 antibody.

41—Use according to embodiment 40 wherein the anti PD-L1 antibody molecule comprises:
  (a) a heavy chain variable region (VH) comprising a VHCDR1 amino acid sequence of SEQ ID NO: 228, a VHCDR2 amino acid sequence of SEQ ID NO: 229, and a VHCDR3 amino acid sequence of SEQ ID NO: 227; and a light chain variable region (VL) comprising a VLCDR1 amino acid sequence of SEQ ID NO: 233, a VLCDR2 amino acid sequence of SEQ ID NO: 234, and a VLCDR3 amino acid sequence of SEQ ID NO: 235;
  (b) a VH comprising a VHCDR1 amino acid sequence of SEQ ID NO: 225; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232;
  (c) a VH comprising a VHCDR1 amino acid sequence of SEQ ID NO: 244, a VHCDR2 amino acid sequence of SEQ ID NO: 229, and a VHCDR3 amino acid sequence of SEQ ID NO: 227; and a VL comprising a VLCDR1 amino acid sequence of SEQ ID NO: 233, a VLCDR2 amino acid sequence of SEQ ID NO: 234, and a VLCDR3 amino acid sequence of SEQ ID NO: 235; or
  (d) a VH comprising a VHCDR1 amino acid sequence of SEQ ID NO: 244; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232.

42—Use according to embodiment 40 wherein the anti-PD-L1 antibody molecule comprises a heavy chain variable domain comprising the amino acid sequence of SEQ ID NO: 236 and a light chain variable domain comprising the amino acid sequence of SEQ ID NO: 239.

43—Combination for use according to any one of embodiments 6-20 or use of combination according to any one of embodiments 29-42 wherein the combination of the immunotherapeutic agent is administered together in a single composition or administered separately in two or more different compositions forms.

44—Combination for use according to any one of embodiments 6-20 or use of combination according to any one of embodiments 29-42 wherein the immunotherapeutic agent is administered concurrently with, prior to, or subsequent to, the compound of Formula (I).

EXAMPLES

The compound of formula (I) of the present invention can be prepared by using the procedure disclosed in patent application WO 2011/121418 A1, which is incorporated to the present application by reference. Particular compounds used in the following assays are the following:
  Compound of formula (I) of the present invention, Example 1 of WO 2011/121418 A1: 5-bromo-2,6-di-(1H-pyrazol-1-yl)pyrimidin-4-amine.
  Compound A of the present invention, Example 46 of WO 2011/121418 A1: 5-chloro-2,6-di-(1H-pyrazol-1-yl)pyrimidin-4-amine.
  Compound B of the present invention, Example 48 of WO 2011/121418 A1: 4-amino-2,6-di-(1H-pyrazol-1-yl)pyrimidine-5-carbonitrile.

As disclosed in patent application WO 2011/121418 A1 said compounds have the following binding affinities at hA2A adenosine receptor.

| Compound | Ki(nM) |
|---|---|
| Compound of formula (I) of the present invention | 12 |
| Compound A | 17 |
| Compound B | 7 |

1—Anti-Tumor Activity of Compound of Formula (I) in Mice

Wild type C57Bl/6 female mice were purchased from Charles River and maintained at the Centre de Recherche du Centre Hospitalier de l'Université de Montréal. All experiments were carried out in accordance with guidelines set out by the Animal Experimental Ethics Committee. Syngeneic C57Bl/6 mice were injected with (i) $3 \times 10^5$ B16-CD73+ tumor cells intravenously and treated daily for 15 days with vehicle control or Compound of formula (I) at 15 mg/kg/day by oral gavage, or (ii) $2 \times 10^5$ MCA205 tumor cells intravenously and treated daily for 7 days with vehicle control or Compound of formula (I) at 30 mg/kg/day by oral gavage. Vehicle consisted of 0.1% Tween 80 and 0.5% sodium carboxymethylcellulose (NaCMC) in water. Mice were euthanized at day 15, lungs harvested and tumor nodules counted under dissecting microscope.

As shown in FIG. 1a, oral administration of Compound of formula (I) significantly reduced tumor burden (lung nodule and lung metastasis) of mice injected intravenously with B16-CD73+ or MCA205 tumor cells.

Figure 1B:
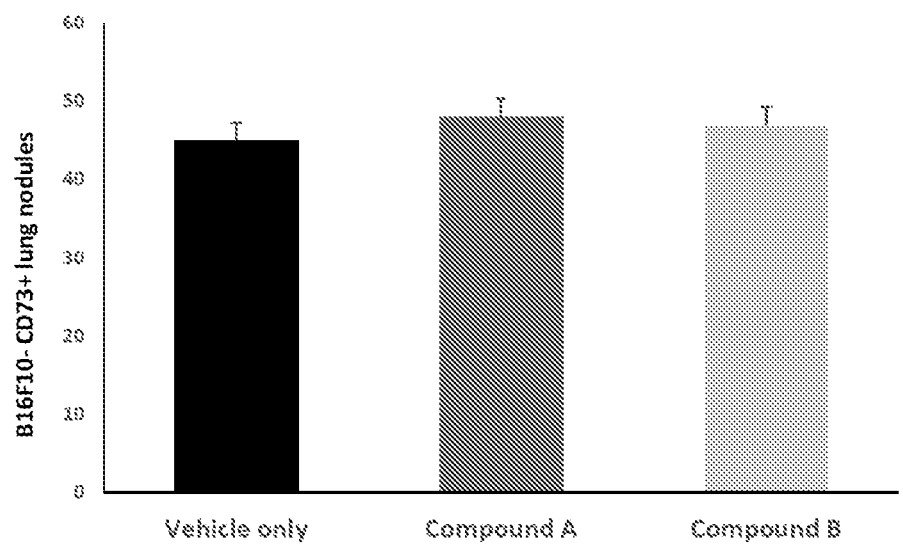
FIGS. 1b and 1c show the anti-tumoral activity of orally administered Compound A and Compound B in two syngeneic mouse models of cancer. (mean lung nodules of 9-10 mice/group±standard errors are shown; *: P<0.05 by Student T test).
Figure 1C:
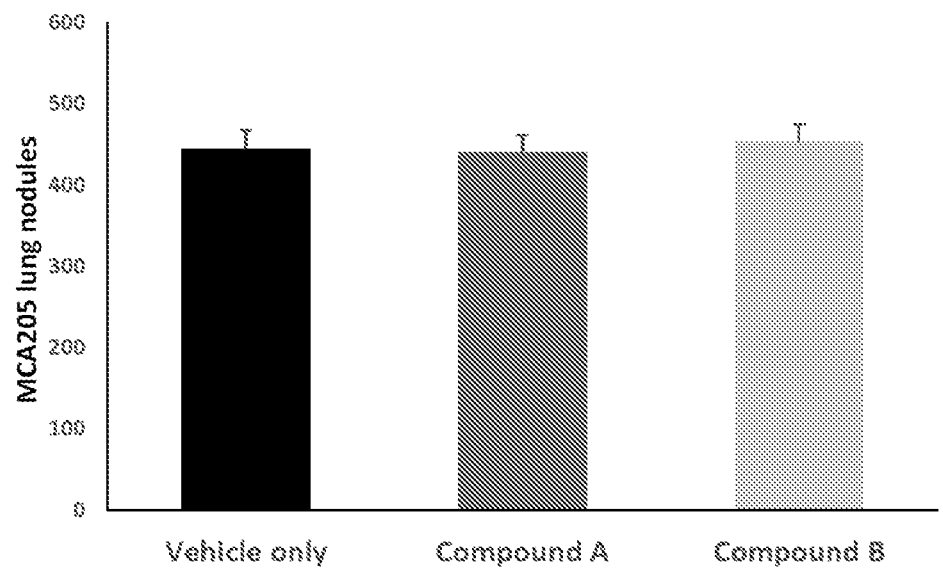
Figure 2:
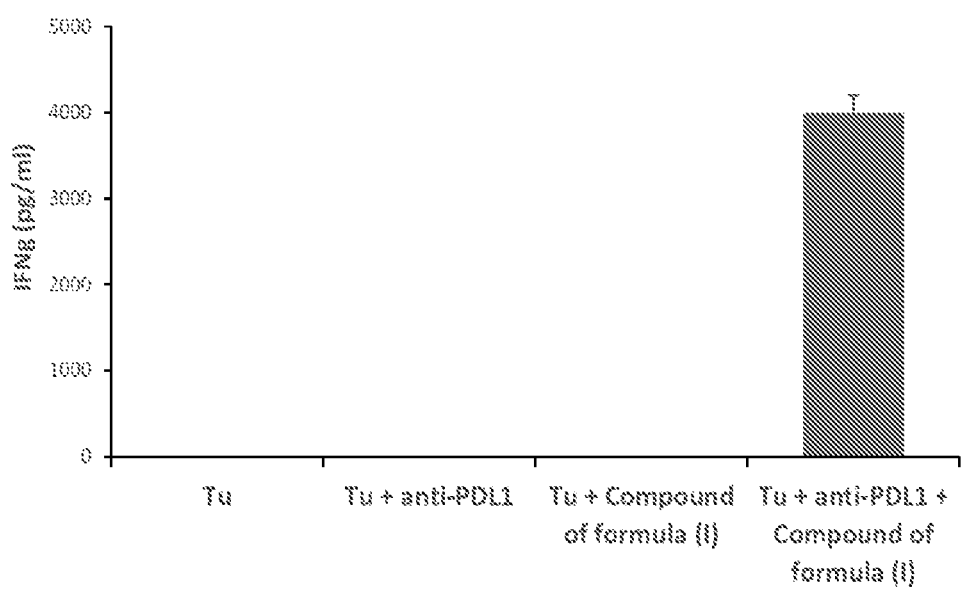
FIG. 2 shows the ability of the combination of the compound of formula (I) and the anti-PD-L1 antibody to significantly increase the interferon gamma secretion of non-stimulated lung tumor cells.
Figure 3:
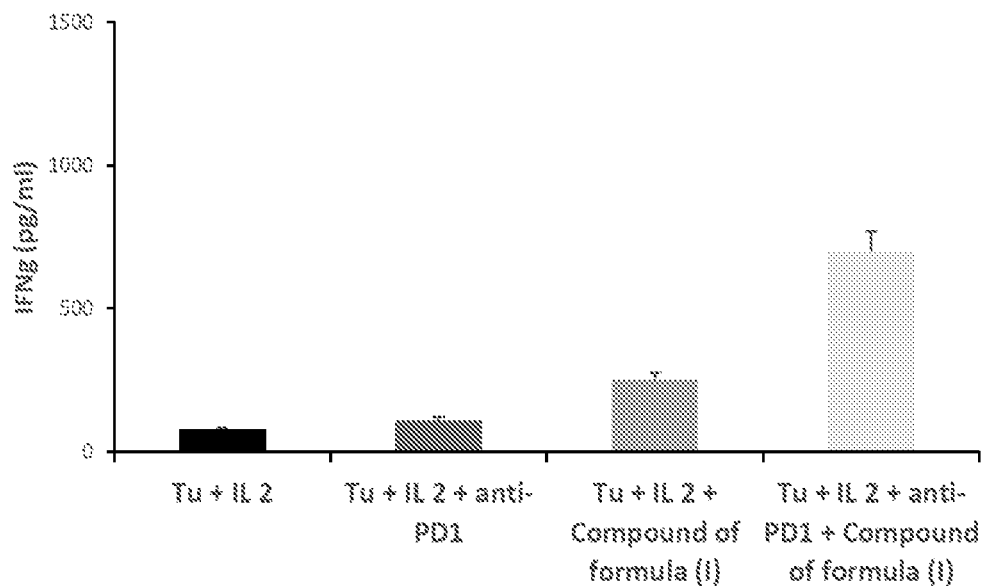
FIG. 3 shows that the interferon gamma secretion from lung tumor cells stimulated with IL-2 can be significantly increased by treatment with compound of formula (I). The effect is more pronounced when the cells are treated with the combination of compound of formula (I) and the anti-PD-1 antibody.
Figure 4:
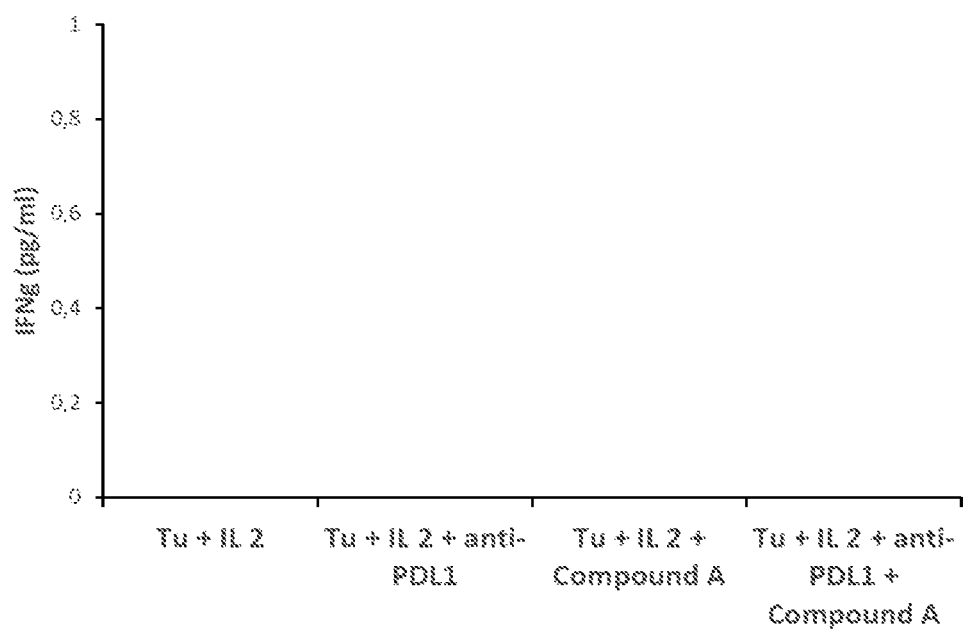
FIGS. 4-7 show that neither the treatment of tumor cells stimulated with IL-2 with compound A or compound B, or with the corresponding combination of compounds A or B with anti-PD-L1 or anti-PD-1 antibodies is able to increase the amount of produced interferon gamma.
Figure 5:
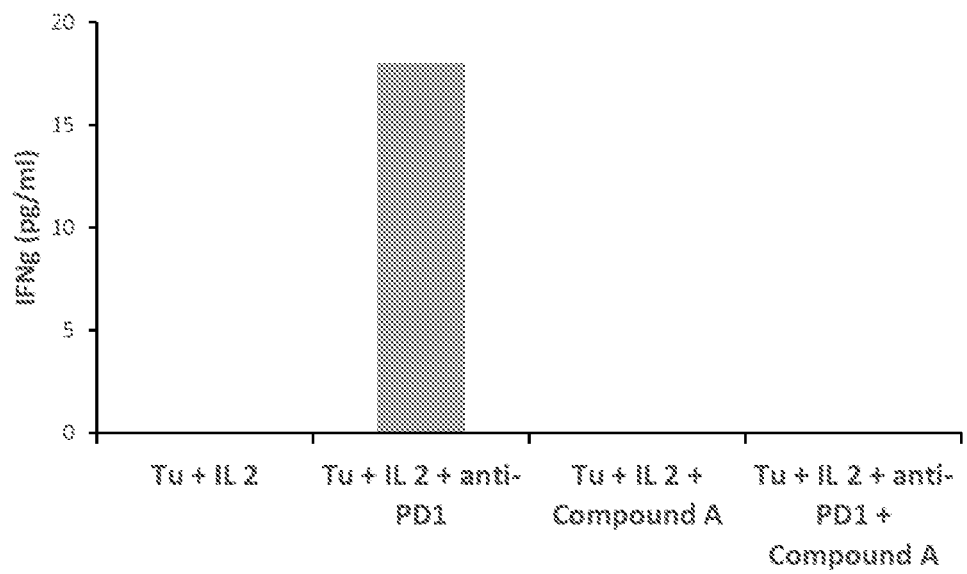
Figure 6:
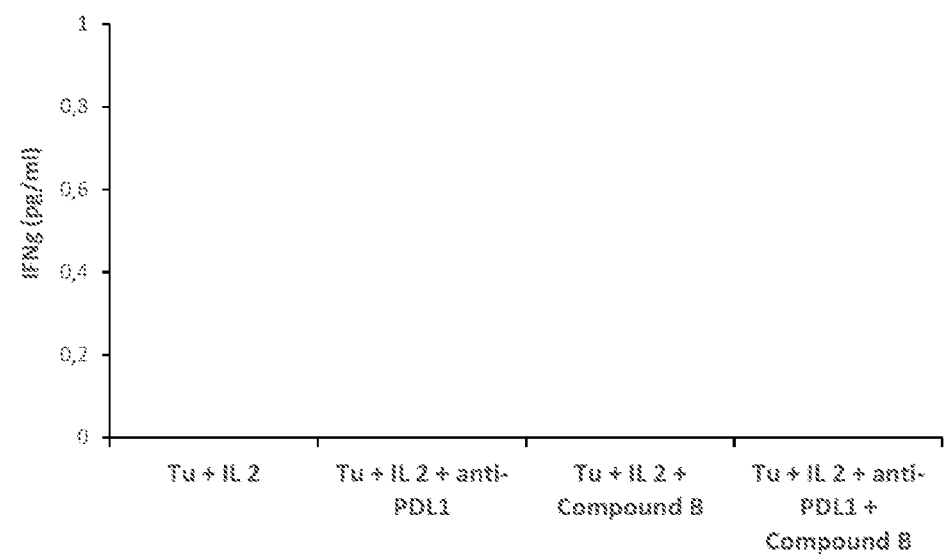
Figure 7:
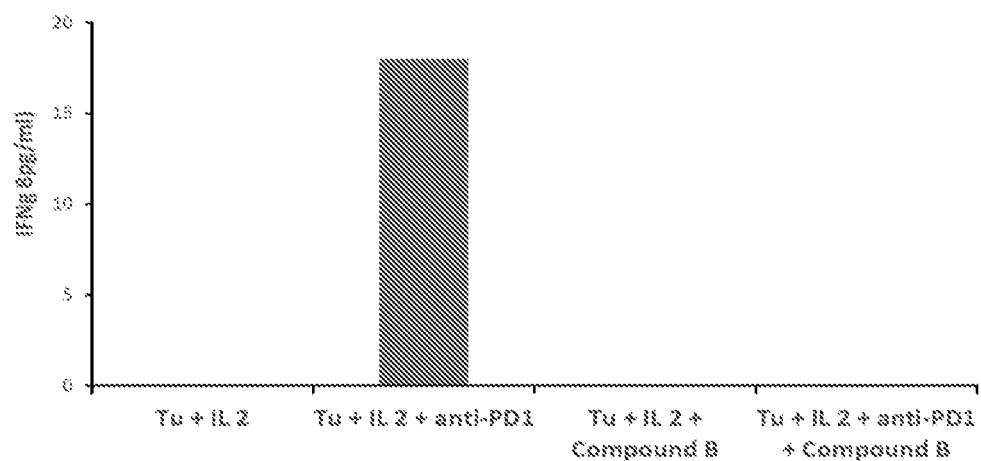
Figure 8A:
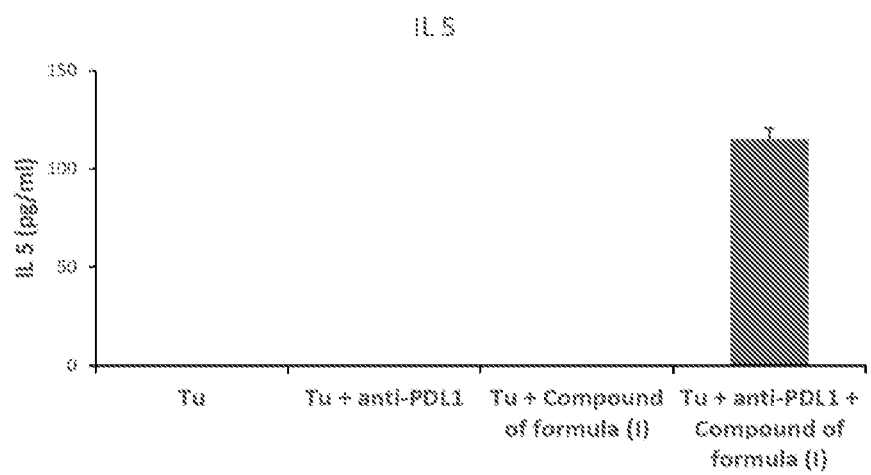
FIGS. 8a-8g show results related to secretion of different interleukins (IL-5, IL-17, IL-1b, IL-13, IL-10, TNFα and MIP 1b) to the medium, due to the stimulation with the compound of formula (I).
Figure 8B:
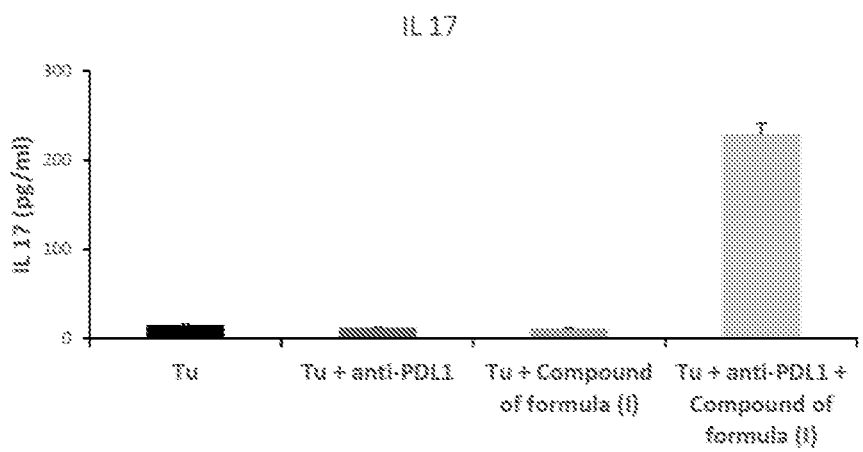
Figure 8C:
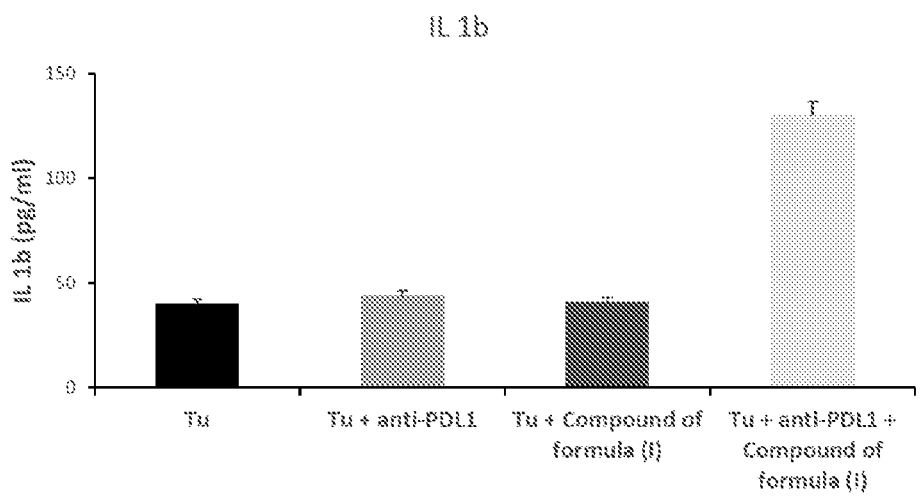
Figure 8D:
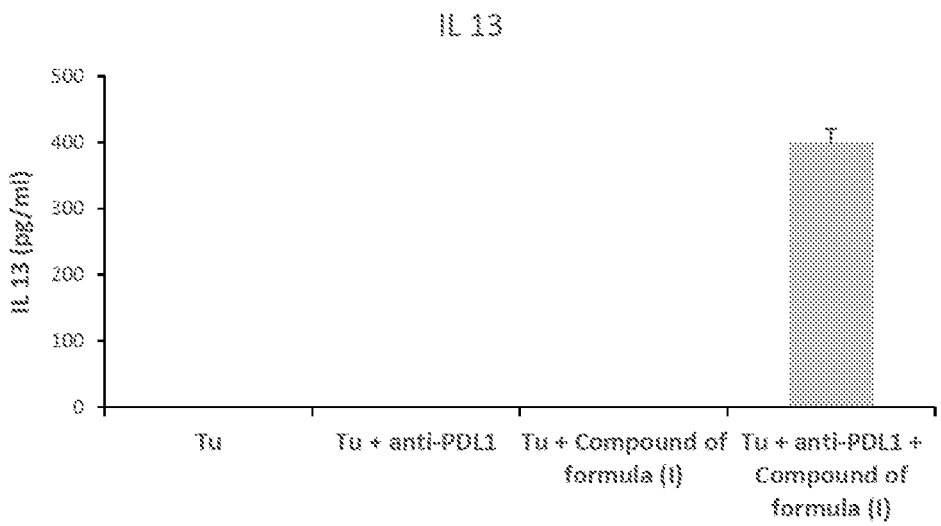
Figure 8E:
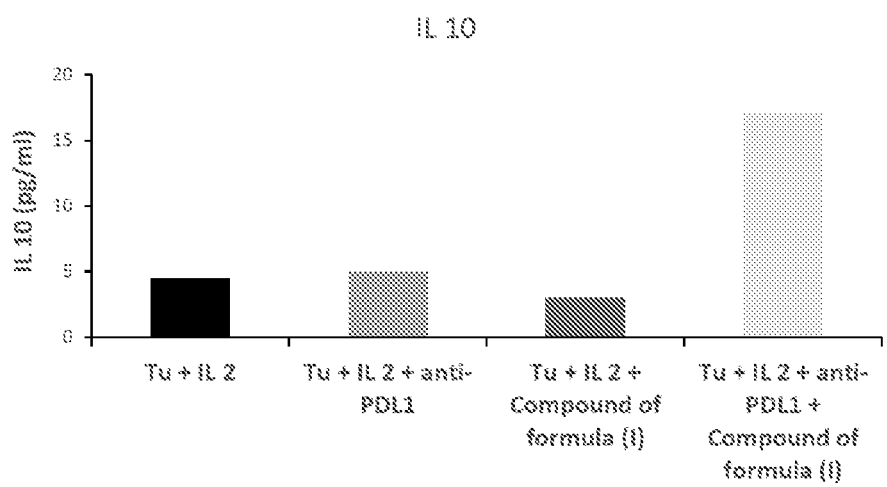
Figure 8F:
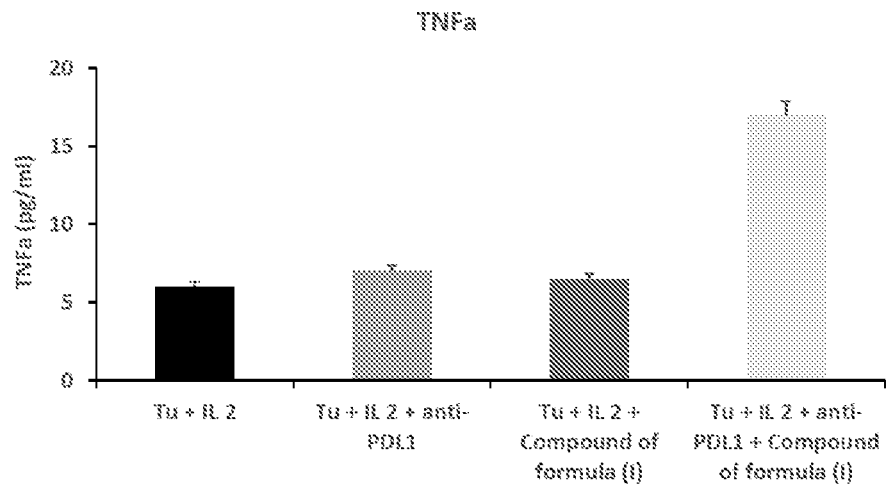
Figure 8G:
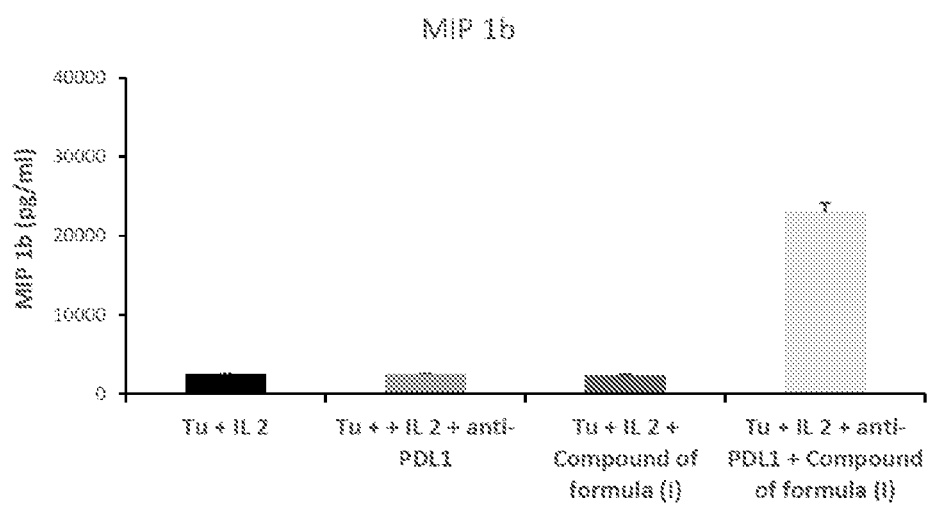

Oral administration of compounds A and B (both at 30 mg/Kg/day) under similar conditions at the Faculty of Pharmacy at the University of Barcelona produced no significant reduction of number of lung nodules as shown in FIGS. 1b and 1c.

2—Ex Vivo Study of the Efficacy of Compound of Formula (I) Alone and in Combination with Anti-PD-1 and Anti-PDL-1 Antibodies in Human Lung Tumour Explants from Patient Ex vivo experiments were done directly using human resistant lung tumours. Freshly resected NSCLC tumors were obtained through the Tissue Core at Moffitt Cancer Center. The tumor was disaggregated for 2 hours in a Collagenase/DNase solution in the presence of complete protease inhibitors (Roche). Total cells (Tu) were counted. 200,000 cells/well were incubated during 3 days and stimulated with IL-2 (6,000 units/ml), Compound of formula (I) (1 µM), Compound A (1 µM), Compound B (1 µM), anti-PD-L1 antibody (10 mg/ml), anti-PD-1 (10 mg/ml) or combination of Compound of formula (I) with anti-PD-L1 antibody (human monoclonal antibody against the PD-L1 receptor Functional Grade Purified 100 µg purchased from eBioscience, #16-5983-82) (10 mg/ml) and anti-PD-1 antibody (human monoclonal antibody against the PD-1 receptor Functional Grade Purified 100 µg purchased from eBioscience, #16-9989-82) (10 mg/ml), respectively. IL-2 has been used in some experiments in order to stimulate the IFN-γ production in these very resistant tumor cells. As was expected with no manipulation or with the addition of small amounts of IL-2, the T cells displayed little to no activity. Adding in either anti-PD-L1 or the compound of formula (I) partially restored TIL reactivity (as determined by measuring IFNg concentration) in some of the samples, and the combination improved TIL function (as determined by measuring IFNg concentration) in additive way. IFNg (IFN-γ ELISA R&D Systems) was determinated as a measure of T cell reactivity to autologous tumor cells. Results are shown in FIGS. 2 to 7.

In other tumors the addition of either anti-PD-L1 or compound of formula (I) had no effect on TIL function (as determined by measuring IFNg concentration), but the combination was synergistically capable of restoring TIL function.

The compounds A and B were tested using similar experimental conditions, with the exception that the freshly resected NSCLC tumors were obtained from the Hospital Clínico in Barcelona. Both compounds were not able to increase the secretion of IFNg of tumor cells, neither alone nor in combination with an anti-PD-L1 or an anti-PD-1 antibody.

3—Analysis of Interleukins Secretion of Resistant Human Lung Tumor Explants after Treatment with Compound of Formula (I)

Supernatants from ex vivo experiments are taken to the Bioplex assay in order to measure the concentration of different interleukins. FIG. 8 a-g show the results obtained in each case. The compound of formula (I) was able to significantly increase the secretion of different interleukins to the medium, specifically of IL5 (Interleukin 5), IL17 (Interleukin 17), ILib (Interleukin 1b), IL13 (Interleukin 13), IL10 (Interleukin 10), tumor necrosis factor α (TNFα), and MIP1b. This is considered a clear signal of immune stimulation of the infiltrating lymphocytes presents in the tumors. The combination of compound of formula (I) with either an anti PDL-1 or an anti-PD-1 antibody increased the secretion of different interleukins of these tumors synergistically.

4. Study Design, Combination of Compound of Formula (I) with an Anti-PD-1 Antibody Patients in this study will be males or females 18 years of age or older and have histologically or cytologically confirmed advanced or metastatic NSCLC with at least one measurable lesion. A compound of Formula I will be administered orally to the patient twice daily, fasting, at a dose of 80 mg, 160 mg, 320 mg or 640 mg throughout a cycle of 28 days. An anti-PD-1 antibody will be administered at a dose of about 300 mg or about 400 mg once every 3 week or once every 4 weeks. The anti-PD-1 antibody will be administered via IV infusion over a period of 30 minutes to 2 h. The compound of Formula I will be administered fasting immediately prior to the infusion with the anti-PD-1 antibody.

In order to determine efficacy, baseline evaluations will be performed as closely as possible to the beginning of treatment and never more than 4 weeks before the beginning of the treatment. In addition to a baseline scan, confirmatory scans will be obtained 4-6 weeks following initial documentation of objective response. Response and progression will be evaluated in this study using the new international criteria proposed by the revised Response Evaluation Criteria in Solid Tumors (RECIST) guideline (version 1.1; Eisenhauer E A, Therasse P, Bogaerts J, et al. New response evaluation criteria in solid tumours: revised RECIST guideline (version 1.1). *Eur J Cancer* 2009; 45:228-47). Changes in the largest diameter (unidimensional measurement) of the tumor lesions and the shortest diameter in the case of malignant lymph nodes are used (Schwartz L H, Bogaerts J, Ford R, et al. Evaluation of lymph nodes with RECIST 1.1. Eur J Cancer 2009; 45:261-7).

All The same method of assessment and the same technique will be used to characterize each identified and reported lesion at baseline and during follow-up. Imaging-based evaluation such as Chest x-ray, conventional CT and MRI will be used.

The invention claimed is:

1. A method of treating cancer comprising administering to a subject in need thereof, a therapeutically effective amount of a compound of formula (I):

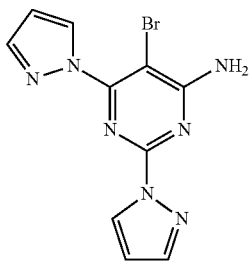

or a pharmaceutically acceptable salt or co-crystal thereof; alone or in combination with one or more immunotherapeutic agents selected from the group consisting of anti-CTLA4 antibodies, anti-PD-1 antibodies and anti-PD-L1 antibodies.

2. The method of claim 1 wherein the cancer is lung cancer.

3. The method of claim 1 wherein the cancer is non-small cell lung cancer.

4. The method according to claim 1 wherein the immunotherapeutic agent is selected from the group consisting of: ipilmumab, tremelimumab, nivolumab, pembrolizumab, CT-011, AMP-224, MPDL3280A, MEDI4736 and MDX-1105.

5. The method according to claim 1 wherein the compound of Formula I is administered in combination with one or more immunotherapeutic agents selected from the group consisting of MPDL3280A, MEDI4736 and MDX-1105.

6. The method according to claim 1 wherein the compound of Formula I is administered in combination with one or more immunotherapeutic agents selected from the group consisting of nivolumab, pembrolizumab, pidilizumab and AMP-224.

7. The method according to claim 1 wherein the compound of Formula I is administered in combination with an immunotherapeutic agent which is an anti-PD-1 antibody.

8. The method according to claim 7 wherein the anti PD-1 antibody comprises:
(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;
(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;
(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or
(d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

9. The method according to claim 7 wherein the anti PD-1 antibody comprises a heavy chain variable domain comprising the amino acid sequence of SEQ ID NO: 38 and a light chain variable domain comprising the amino acid sequence of SEQ ID NO: 70.

10. The method according to claim 7 wherein the anti-PD-1 antibody comprises: a heavy chain comprising the amino acid sequence of SEQ ID NO: 91 and a light chain comprising the amino acid sequence of SEQ ID NO: 72.

11. The method according to claim 7 wherein the anti-PD-1 antibody molecule is administered at a dose of about 300 mg once every three weeks.

12. The method according to claim 7 wherein the anti-PD-1 antibody molecule is administered at a dose of about 400 mg once every four weeks.

13. The method according to claim 1 wherein the compound of Formula I is administered in combination with an immunotherapeutic agent which is an anti-PD-L1 antibody.

14. The method according to claim 13 wherein the anti PD-L1 antibody molecule comprises:
  (a) a heavy chain variable region (VH) comprising a VHCDR1 amino acid sequence of SEQ ID NO: 228, a VHCDR2 amino acid sequence of SEQ ID NO: 229, and a VHCDR3 amino acid sequence of SEQ ID NO: 227; and a light chain variable region (VL) comprising a VLCDR1 amino acid sequence of SEQ ID NO: 233, a VLCDR2 amino acid sequence of SEQ ID NO: 234, and a VLCDR3 amino acid sequence of SEQ ID NO: 235;
  (b) a VH comprising a VHCDR1 amino acid sequence of SEQ ID NO: 225; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232;
  (c) a VH comprising a VHCDR1 amino acid sequence of SEQ ID NO: 244, a VHCDR2 amino acid sequence of SEQ ID NO: 229, and a VHCDR3 amino acid sequence of SEQ ID NO: 227; and a VL comprising a VLCDR1 amino acid sequence of SEQ ID NO: 233, a VLCDR2 amino acid sequence of SEQ ID NO: 234, and a VLCDR3 amino acid sequence of SEQ ID NO: 235; or
  (d) a VH comprising a VHCDR1 amino acid sequence of SEQ ID NO: 244; a VHCDR2 amino acid sequence of SEQ ID NO: 226; and a VHCDR3 amino acid sequence of SEQ ID NO: 227; and a VL comprising a VLCDR1 amino acid sequence of SEQ ID NO: 230, a VLCDR2 amino acid sequence of SEQ ID NO: 231, and a VLCDR3 amino acid sequence of SEQ ID NO: 232.

15. The method according to claim 13 wherein the anti-PD-L1 antibody molecule comprises a heavy chain variable domain comprising the amino acid sequence of SEQ ID NO: 236 and a light chain variable domain comprising the amino acid sequence of SEQ ID NO: 239.

16. The method according to claim 1 wherein the combination of the immunotherapeutic agent is administered together in a single composition or administered separately in two or more different compositions forms.

17. The method according to claim 1 wherein the immunotherapeutic agent is administered concurrently with, prior to, or subsequent to, the compound of Formula (I).

* * * * *